United States Patent
Schotte et al.

(10) Patent No.: US 11,851,480 B2
(45) Date of Patent: *Dec. 26, 2023

(54) METHOD FOR THE PRODUCTION OF IMMUNOGLOBULIN SINGLE VARIABLE DOMAINS

(71) Applicant: Ablynx N.V., Ghent-Zwijnaarde (BE)

(72) Inventors: Peter Schotte, De Pinte (BE); Manu De Groeve, Nieuwerkerken (BE)

(73) Assignee: Ablynx N.V., Zwijnaarde (BE)

( * ) Notice: Subject to any disclaimer, the term of this patent is extended or adjusted under 35 U.S.C. 154(b) by 71 days.

This patent is subject to a terminal disclaimer.

(21) Appl. No.: 16/943,022

(22) Filed: Jul. 30, 2020

(65) Prior Publication Data
US 2021/0047392 A1 Feb. 18, 2021

Related U.S. Application Data

(63) Continuation of application No. 16/076,314, filed as application No. PCT/EP2017/053034 on Feb. 10, 2017, now Pat. No. 10,975,141.

(60) Provisional application No. 62/294,470, filed on Feb. 12, 2016.

(51) Int. Cl.
| | |
|---|---|
| C12Q 1/68 | (2018.01) |
| C07K 16/18 | (2006.01) |
| C07K 14/39 | (2006.01) |
| C12N 15/09 | (2006.01) |
| C12P 21/02 | (2006.01) |

(52) U.S. Cl.
CPC .............. *C07K 16/18* (2013.01); *C07K 14/39* (2013.01); *C12N 15/09* (2013.01); *C12P 21/02* (2013.01); *C07K 2317/14* (2013.01); *C07K 2317/35* (2013.01); *C07K 2317/569* (2013.01); *C07K 2317/94* (2013.01)

(58) Field of Classification Search
None
See application file for complete search history.

(56) References Cited

U.S. PATENT DOCUMENTS

| 2009/0191587 A1 | 7/2009 | Chiba et al. |
| 2019/0194302 A1 | 6/2019 | Schotte et al. |

FOREIGN PATENT DOCUMENTS

| CN | 103917560 A | 7/2014 |
| EP | 2022855 A1 | 2/2009 |
| WO | WO 2007/132949 A1 | 11/2007 |
| WO | WO 2009/138519 A1 | 11/2009 |
| WO | WO 2010/125187 A2 | 11/2010 |
| WO | WO 2010/135678 A1 | 11/2010 |
| WO | WO 2011/161266 A1 | 12/2011 |
| WO | WO 2012/130874 A1 | 10/2012 |
| WO | WO 2015/173325 A2 | 11/2015 |

OTHER PUBLICATIONS

Claes et al., Modular integrated secretory system engineering in Pichia pastoris to enhance G-protein coupled receptor expression. ACS Synth Biol. May 13, 2016; 5(10): 1070-1075.
Royle et al., Modelling as a tool for increasing the specific productivity of single-chain antibody fragments from Pichia pastoris—a thesis submitted for the degree of doctor of philosophy of Imperial College London and the Diploma of Imperial College London 2013. Imperial College London. Sep. 1, 2013.
Sockolosky et al., Fusion of a short peptide that binds immunoglobulin G to a recombinant protein substantially increases its plasma half-life in mice. PLoS One. Jul. 24, 2014;9(7):e102566. doi: 10.1371/journal.pone.0102566.
Gasser et al., Engineering of Pichia pastoris for improved production of antibody fragments. Biotechnol Bioeng. Jun. 5, 2006;94(2):353-61. doi: 10.1002/bit.20851.
Guerfal et al., The HAC1 gene from Pichia pastoris: characterization and effect of its overexpression on the production of secreted, surface displayed and membrane proteins. Microb Cell Fact. Jun. 30, 2010;9:49. doi: 10.1186/1475-2859-9-49.
Holt et al., Domain antibodies: proteins for therapy. Trends Biotechnol. Nov. 2003;21(11):484-90. doi: 10.1016/j.tibtech.2003.08.007.
17704752.6, Apr. 26, 2023, Third Party Observations.
Third Party Observations for Application No. EP 17704752.9 dated Apr. 26, 2023. 10 pages.
Bibila et al., A structured model for monoclonal antibody synthesis in exponentially growing and stationary phase hybridoma cells. Biotechnol Bioeng. Feb. 5, 1991;37(3):210-26. doi: 10.1002/bit. 260370304.
Hohenblum et al., Effects of gene dosage, promoters, and substrates on unfolded protein stress of recombinant Pichia pastoris. Biotechnol Bioeng. Feb. 20, 2004;85(4):367-75. doi: 10.1002/bit.10904.
Kauffman et al., Decreased protein expression and intermittent recoveries in BiP levels result from cellular stress during heterologous protein expression in *Saccharomyces cerevisiae*. Biotechnol Prog. Sep. 2002-Oct.:18(5):942-50. doi: 10.1021/bp025518g.

*Primary Examiner* — Jennifer E Graser
(74) *Attorney, Agent, or Firm* — Wolf, Greenfield & Sacks, P.C.

(57) ABSTRACT

Methods are provided for the manufacture of polypeptides comprising at least one immunoglobulin variable domain that result in an increased yield. The methods are based on simultaneous enhancement of one or more auxiliary proteins in the host.

18 Claims, 3 Drawing Sheets
Specification includes a Sequence Listing.

SEQUENCE LISTING

<160> NUMBER OF SEQ ID NOS: 63

<210> SEQ ID NO 1
<211> LENGTH: 270
<212> TYPE: PRT
<213> ORGANISM: Escherichia coli

<400> SEQUENCE: 1

Met Lys Ser Leu Phe Lys Val Thr Leu Leu Ala Thr Thr Met Ala Val
1               5                   10                  15

```
Ala Leu His Ala Pro Ile Thr Phe Ala Glu Ala Ala Lys Pro Ala
            20                  25                  30
Thr Thr Ala Asp Ser Lys Ala Ala Phe Lys Asn Asp Asp Gln Lys Ser
        35                  40                  45
Ala Tyr Ala Leu Gly Ala Ser Leu Gly Arg Tyr Met Glu Asn Ser Leu
    50                  55                  60
Lys Glu Gln Glu Lys Leu Gly Ile Lys Leu Asp Lys Asp Gln Leu Ile
65                  70                  75                  80
Ala Gly Val Gln Asp Ala Phe Ala Asp Lys Ser Lys Leu Ser Asp Gln
                85                  90                  95
Glu Ile Glu Gln Thr Leu Gln Ala Phe Glu Ala Arg Val Lys Ser Ser
            100                 105                 110
Ala Gln Ala Lys Met Glu Lys Asp Ala Ala Asp Asn Glu Ala Lys Gly
        115                 120                 125
Lys Glu Tyr Arg Glu Lys Phe Ala Lys Glu Lys Gly Val Lys Thr Ser
    130                 135                 140
Ser Thr Gly Leu Val Tyr Gln Val Val Glu Ala Gly Lys Gly Glu Ala
145                 150                 155                 160
Pro Lys Asp Ser Asp Thr Val Val Val Asn Tyr Lys Gly Thr Leu Ile
                165                 170                 175
Asp Gly Lys Glu Phe Asp Asn Ser Tyr Thr Arg Gly Glu Pro Leu Ser
            180                 185                 190
Phe Arg Leu Asp Gly Val Ile Pro Gly Trp Thr Glu Gly Leu Lys Asn
        195                 200                 205
Ile Lys Lys Gly Gly Lys Ile Lys Leu Val Ile Pro Pro Glu Leu Ala
    210                 215                 220
Tyr Gly Lys Ala Gly Val Pro Gly Ile Pro Pro Asn Ser Thr Leu Val
225                 230                 235                 240
Phe Asp Val Glu Leu Leu Asp Val Lys Pro Ala Pro Lys Ala Asp Ala
                245                 250                 255
Lys Pro Glu Ala Asp Ala Lys Ala Ala Asp Ser Ala Lys Lys
            260                 265                 270

<210> SEQ ID NO 2
<211> LENGTH: 161
<212> TYPE: PRT
<213> ORGANISM: Escherichia coli

<400> SEQUENCE: 2

Met Lys Lys Trp Leu Leu Ala Ala Gly Leu Gly Leu Ala Leu Ala Thr
1               5                   10                  15
Ser Ala Gln Ala Ala Asp Lys Ile Ala Ile Val Asn Met Gly Ser Leu
            20                  25                  30
Phe Gln Gln Val Ala Gln Lys Thr Gly Val Ser Asn Thr Leu Glu Asn
        35                  40                  45
Glu Phe Lys Gly Arg Ala Ser Glu Leu Gln Arg Met Glu Thr Asp Leu
    50                  55                  60
Gln Ala Lys Met Lys Lys Leu Gln Ser Met Lys Ala Gly Ser Asp Arg
65                  70                  75                  80
Thr Lys Leu Glu Lys Asp Val Met Ala Gln Arg Gln Thr Phe Ala Gln
                85                  90                  95
Lys Ala Gln Ala Phe Glu Gln Asp Arg Ala Arg Arg Ser Asn Glu Glu
            100                 105                 110
Arg Gly Lys Leu Val Thr Arg Ile Gln Thr Ala Val Lys Ser Val Ala
        115                 120                 125
```

Asn Ser Gln Asp Ile Asp Leu Val Val Asp Ala Asn Ala Val Ala Tyr
            130                 135                 140

Asn Ser Ser Asp Val Lys Asp Ile Thr Ala Asp Val Leu Lys Gln Val
145                 150                 155                 160

Lys

<210> SEQ ID NO 3
<211> LENGTH: 527
<212> TYPE: PRT
<213> ORGANISM: Pichia pastoris

<400> SEQUENCE: 3

Met Arg Ile Val Arg Ser Val Ala Ile Ala Ile Ala Cys His Cys Ile
1               5                   10                  15

Thr Ala Leu Ala Asn Pro Gln Ile Pro Phe Asp Gly Asn Tyr Thr Glu
            20                  25                  30

Ile Ile Val Pro Asp Thr Glu Val Asn Ile Gly Gln Ile Val Asp Ile
            35                  40                  45

Asn His Glu Ile Lys Pro Lys Leu Val Glu Leu Val Asn Thr Asp Phe
    50                  55                  60

Phe Lys Tyr Tyr Lys Leu Asn Leu Trp Lys Pro Cys Pro Phe Trp Asn
65                  70                  75                  80

Gly Asp Glu Gly Phe Cys Lys Tyr Lys Asp Cys Ser Val Asp Phe Ile
                85                  90                  95

Thr Asp Trp Ser Gln Val Pro Asp Ile Trp Gln Pro Asp Gln Leu Gly
            100                 105                 110

Lys Leu Gly Asp Asn Thr Val His Lys Asp Lys Gly Gln Asp Glu Asn
        115                 120                 125

Glu Leu Ser Ser Asn Asp Tyr Cys Ala Leu Asp Lys Asp Asp Asp Glu
    130                 135                 140

Asp Leu Val Tyr Val Asn Leu Ile Asp Asn Pro Glu Arg Phe Thr Gly
145                 150                 155                 160

Tyr Gly Gly Gln Gln Ser Glu Ser Ile Trp Thr Ala Val Tyr Asp Glu
                165                 170                 175

Asn Cys Phe Gln Pro Asn Glu Gly Ser Gln Leu Gly Gln Val Glu Asp
            180                 185                 190

Leu Cys Leu Glu Lys Gln Ile Phe Tyr Arg Leu Val Ser Gly Leu His
        195                 200                 205

Ser Ser Ile Ser Thr His Leu Thr Asn Glu Tyr Leu Asn Leu Lys Asn
    210                 215                 220

Gly Ala Tyr Glu Pro Asn Leu Lys Gln Phe Met Ile Lys Val Gly Tyr
225                 230                 235                 240

Phe Thr Glu Arg Ile Gln Asn Leu His Leu Asn Tyr Val Leu Val Leu
                245                 250                 255

Lys Ser Leu Ile Lys Leu Gln Glu Tyr Asn Val Ile Asp Asn Leu Pro
            260                 265                 270

Leu Asp Asp Ser Leu Lys Ala Gly Leu Ser Gly Leu Ile Ser Gln Gly
        275                 280                 285

Ala Gln Gly Ile Asn Gln Ser Ser Asp Asp Tyr Leu Phe Asn Glu Lys
    290                 295                 300

Val Leu Phe Gln Asn Asp Gln Asn Asp Leu Lys Asn Glu Phe Arg
305                 310                 315                 320

Asp Lys Phe Arg Asn Val Thr Arg Leu Met Asp Cys Val His Cys Glu
                325                 330                 335

```
Arg Cys Lys Leu Trp Gly Lys Leu Gln Thr Thr Gly Tyr Gly Thr Ala
                340                 345                 350

Leu Lys Ile Leu Phe Asp Leu Lys Asn Pro Asn Asp Ser Ile Asn Leu
                355                 360                 365

Lys Arg Val Glu Leu Val Ala Leu Val Asn Thr Phe His Arg Leu Ser
            370                 375                 380

Lys Ser Val Glu Ser Ile Glu Asn Phe Glu Lys Leu Tyr Lys Ile Gln
385                 390                 395                 400

Pro Pro Thr Gln Asp Arg Ala Ser Ala Ser Ser Glu Ser Leu Gly Leu
                405                 410                 415

Phe Asp Asn Glu Asp Glu Gln Asn Leu Leu Asn Ser Phe Ser Val Asp
                420                 425                 430

Gln Ala Val Ile Ser Ser Lys Glu Ala Pro Glu Glu Ile Lys Ser Lys
            435                 440                 445

Pro Val Gly Lys Ala Ala Tyr Lys Gln Asn Ser Cys Pro Ser Leu Gly
            450                 455                 460

Ser Lys Ser Ile Lys Glu Ala Phe His Glu Glu Leu His Ala Phe Ile
465                 470                 475                 480

Asp Ala Ile Gly Phe Ile Leu Asn Ser Tyr Arg Thr Leu Pro Lys Leu
                485                 490                 495

Leu Tyr Thr Leu Phe Leu Val Lys Ser Ser Glu Leu Trp Asp Ile Phe
            500                 505                 510

Ile Gly Thr Gln Arg His Arg Asp Thr Thr Tyr Arg Val Asp Leu
            515                 520                 525

<210> SEQ ID NO 4
<211> LENGTH: 678
<212> TYPE: PRT
<213> ORGANISM: Pichia pastoris

<400> SEQUENCE: 4

Met Leu Ser Leu Lys Pro Ser Trp Leu Thr Leu Ala Ala Leu Met Tyr
1               5                   10                  15

Ala Met Leu Leu Val Val Pro Phe Ala Lys Pro Val Arg Ala Asp
            20                  25                  30

Asp Val Glu Ser Tyr Gly Thr Val Ile Gly Ile Asp Leu Gly Thr Thr
            35                  40                  45

Tyr Ser Cys Val Gly Val Met Lys Ser Gly Arg Val Glu Ile Leu Ala
        50                  55                  60

Asn Asp Gln Gly Asn Arg Ile Thr Pro Ser Tyr Val Ser Phe Thr Glu
65              70                  75                  80

Asp Glu Arg Leu Val Gly Asp Ala Ala Lys Asn Leu Ala Ala Ser Asn
                85                  90                  95

Pro Lys Asn Thr Ile Phe Asp Ile Lys Arg Leu Ile Gly Met Lys Tyr
            100                 105                 110

Asp Ala Pro Glu Val Gln Arg Asp Leu Lys Arg Leu Pro Tyr Thr Val
        115                 120                 125

Lys Ser Lys Asn Gly Gln Pro Val Val Ser Val Glu Tyr Lys Gly Glu
130                 135                 140

Glu Lys Ser Phe Thr Pro Glu Glu Ile Ser Ala Met Val Leu Gly Lys
145                 150                 155                 160

Met Lys Leu Ile Ala Glu Asp Tyr Leu Gly Lys Lys Val Thr His Ala
                165                 170                 175

Val Val Thr Val Pro Ala Tyr Phe Asn Asp Ala Gln Arg Gln Ala Thr
```

```
                180             185             190
Lys Asp Ala Gly Leu Ile Ala Gly Leu Thr Val Leu Arg Ile Val Asn
    195                 200                 205

Glu Pro Thr Ala Ala Leu Ala Tyr Gly Leu Asp Lys Thr Gly Glu
210                 215                 220

Glu Arg Gln Ile Ile Val Tyr Asp Leu Gly Gly Thr Phe Asp Val
225                 230                 235                 240

Ser Leu Leu Ser Ile Glu Gly Ala Phe Glu Val Leu Ala Thr Ala
                245                 250                 255

Gly Asp Thr His Leu Gly Gly Glu Asp Phe Asp Tyr Arg Val Val Arg
                260                 265                 270

His Phe Val Lys Ile Phe Lys Lys Lys His Asn Ile Asp Ile Ser Asn
            275                 280                 285

Asn Asp Lys Ala Leu Gly Lys Leu Lys Arg Glu Val Glu Lys Ala Lys
            290                 295                 300

Arg Thr Leu Ser Ser Gln Met Thr Thr Arg Ile Glu Ile Asp Ser Phe
305                 310                 315                 320

Val Asp Gly Ile Asp Phe Ser Glu Gln Leu Ser Arg Ala Lys Phe Glu
                325                 330                 335

Glu Ile Asn Ile Glu Leu Phe Lys Lys Thr Leu Lys Pro Val Glu Gln
                340                 345                 350

Val Leu Lys Asp Ala Gly Val Lys Lys Ser Glu Ile Asp Asp Ile Val
                355                 360                 365

Leu Val Gly Gly Ser Thr Arg Ile Pro Lys Val Gln Gln Leu Leu Glu
            370                 375                 380

Asp Tyr Phe Asp Gly Lys Lys Ala Ser Lys Gly Ile Asn Pro Asp Glu
385                 390                 395                 400

Ala Val Ala Tyr Gly Ala Ala Val Gln Ala Gly Val Leu Ser Gly Glu
                405                 410                 415

Glu Gly Val Asp Asp Ile Val Leu Leu Asp Val Asn Pro Leu Thr Leu
            420                 425                 430

Gly Ile Glu Thr Thr Gly Gly Val Met Thr Thr Leu Ile Asn Arg Asn
            435                 440                 445

Thr Ala Ile Pro Thr Lys Lys Ser Gln Ile Phe Ser Thr Ala Ala Asp
    450                 455                 460

Asn Gln Pro Thr Val Leu Ile Gln Val Tyr Glu Gly Glu Arg Ala Leu
465                 470                 475                 480

Ala Lys Asp Asn Asn Leu Leu Gly Lys Phe Glu Leu Thr Gly Ile Pro
                485                 490                 495

Pro Ala Pro Arg Gly Thr Pro Gln Val Glu Val Thr Phe Val Leu Asp
                500                 505                 510

Ala Asn Gly Ile Leu Lys Val Ser Ala Thr Asp Lys Gly Thr Gly Lys
            515                 520                 525

Ser Glu Ser Ile Thr Ile Asn Asn Asp Arg Gly Arg Leu Ser Lys Glu
            530                 535                 540

Glu Val Asp Arg Met Val Glu Ala Glu Lys Tyr Ala Ala Glu Asp
545                 550                 555                 560

Ala Ala Leu Arg Glu Lys Ile Glu Ala Arg Asn Ala Leu Glu Asn Tyr
                565                 570                 575

Ala His Ser Leu Arg Asn Gln Val Thr Asp Asp Ser Glu Thr Gly Leu
            580                 585                 590

Gly Ser Lys Leu Asp Glu Asp Asp Lys Glu Thr Leu Thr Asp Ala Ile
            595                 600                 605
```

```
Lys Asp Thr Leu Glu Phe Leu Glu Asp Asn Phe Asp Thr Ala Thr Lys
610                 615                 620
Glu Glu Leu Asp Glu Gln Arg Glu Lys Leu Ser Lys Ile Ala Tyr Pro
625                 630                 635                 640
Ile Thr Ser Lys Leu Tyr Gly Ala Pro Glu Gly Thr Pro Pro Gly
            645                 650                 655
Gly Gln Gly Phe Asp Asp Asp Gly Asp Phe Asp Tyr Asp Tyr Asp
        660                 665                 670
Tyr Asp His Asp Glu Leu
        675

<210> SEQ ID NO 5
<211> LENGTH: 517
<212> TYPE: PRT
<213> ORGANISM: Pichia pastoris

<400> SEQUENCE: 5

Met Gln Phe Asn Trp Asn Ile Lys Thr Val Ala Ser Ile Leu Ser Ala
1               5                   10                  15
Leu Thr Leu Ala Gln Ala Ser Asp Gln Glu Ala Ile Ala Pro Glu Asp
            20                  25                  30
Ser His Val Val Lys Leu Thr Glu Ala Thr Phe Glu Ser Phe Ile Thr
        35                  40                  45
Ser Asn Pro His Val Leu Ala Glu Phe Phe Ala Pro Trp Cys Gly His
    50                  55                  60
Cys Lys Lys Leu Gly Pro Glu Leu Val Ser Ala Ala Glu Ile Leu Lys
65                  70                  75                  80
Asp Asn Glu Gln Val Lys Ile Ala Gln Ile Asp Cys Thr Glu Glu Lys
                85                  90                  95
Glu Leu Cys Gln Gly Tyr Glu Ile Lys Gly Tyr Pro Thr Leu Lys Val
            100                 105                 110
Phe His Gly Glu Val Glu Val Pro Ser Asp Tyr Gln Gly Gln Arg Gln
        115                 120                 125
Ser Gln Ser Ile Val Ser Tyr Met Leu Lys Gln Ser Leu Pro Pro Val
    130                 135                 140
Ser Glu Ile Asn Ala Thr Lys Asp Leu Asp Asp Thr Ile Ala Glu Ala
145                 150                 155                 160
Lys Glu Pro Val Ile Val Gln Val Leu Pro Glu Asp Ala Ser Asn Leu
                165                 170                 175
Glu Ser Asn Thr Thr Phe Tyr Gly Val Ala Gly Thr Leu Arg Glu Lys
            180                 185                 190
Phe Thr Phe Val Ser Thr Lys Ser Thr Asp Tyr Ala Lys Lys Tyr Thr
        195                 200                 205
Ser Asp Ser Thr Pro Ala Tyr Leu Leu Val Arg Pro Gly Glu Glu Pro
    210                 215                 220
Ser Val Tyr Ser Gly Glu Glu Leu Asp Glu Thr His Leu Val His Trp
225                 230                 235                 240
Ile Asp Ile Glu Ser Lys Pro Leu Phe Gly Asp Ile Asp Gly Ser Thr
                245                 250                 255
Phe Lys Ser Tyr Ala Glu Ala Asn Ile Pro Leu Ala Tyr Tyr Phe Tyr
            260                 265                 270
Glu Asn Glu Glu Gln Arg Ala Ala Ala Asp Ile Ile Lys Pro Phe
        275                 280                 285
Ala Lys Glu Gln Arg Gly Lys Ile Asn Phe Val Gly Leu Asp Ala Val
```

```
                290                 295                 300

Lys Phe Gly Lys His Ala Lys Asn Leu Asn Met Asp Glu Glu Lys Leu
305                 310                 315                 320

Pro Leu Phe Val Ile His Asp Leu Val Ser Asn Lys Lys Phe Gly Val
                325                 330                 335

Pro Gln Asp Gln Glu Leu Thr Asn Lys Asp Val Thr Glu Leu Ile Glu
                340                 345                 350

Lys Phe Ile Ala Gly Glu Ala Glu Pro Ile Val Lys Ser Glu Pro Ile
                355                 360                 365

Pro Glu Ile Gln Glu Glu Lys Val Phe Lys Leu Val Gly Lys Ala His
                370                 375                 380

Asp Glu Val Val Phe Asp Glu Ser Lys Asp Val Leu Val Lys Tyr Tyr
385                 390                 395                 400

Ala Pro Trp Cys Gly His Cys Lys Arg Met Ala Pro Ala Tyr Glu Glu
                405                 410                 415

Leu Ala Thr Leu Tyr Ala Asn Asp Glu Asp Ala Ser Ser Lys Val Val
                420                 425                 430

Ile Ala Lys Leu Asp His Thr Leu Asn Asp Val Asp Asn Val Asp Ile
                435                 440                 445

Gln Gly Tyr Pro Thr Leu Ile Leu Tyr Pro Ala Gly Asp Lys Ser Asn
450                 455                 460

Pro Gln Leu Tyr Asp Gly Ser Arg Asp Leu Glu Ser Leu Ala Glu Phe
465                 470                 475                 480

Val Lys Glu Arg Gly Thr His Lys Val Asp Ala Leu Ala Leu Arg Pro
                485                 490                 495

Val Glu Glu Glu Lys Glu Ala Glu Glu Ala Glu Ser Glu Ala Asp
                500                 505                 510

Ala His Asp Glu Leu
                515

<210> SEQ ID NO 6
<211> LENGTH: 312
<212> TYPE: PRT
<213> ORGANISM: Pichia pastoris

<400> SEQUENCE: 6

Met Gly Gly Ile Asn Glu Lys Lys Ala Glu Tyr Phe Asn Lys Leu Arg
1               5                   10                  15

Glu Leu Leu Glu Ser Tyr Lys Ser Ile Phe Ile Val Gly Val Asp Asn
                20                  25                  30

Val Ser Ser Gln Gln Met His Glu Val Arg Gln Thr Leu Arg Gly Lys
                35                  40                  45

Ala Val Ile Leu Met Gly Lys Asn Thr Met Val Arg Lys Ala Leu Arg
                50                  55                  60

Asp Phe Val Glu Glu Leu Pro Val Phe Glu Lys Leu Leu Pro Phe Val
65                  70                  75                  80

Arg Gly Asn Ile Gly Phe Val Phe Thr Asn Glu Asp Leu Lys Thr Ile
                85                  90                  95

Arg Asp Val Ile Ile Glu Asn Arg Val Ala Ala Pro Ala Arg Pro Gly
                100                 105                 110

Ala Ile Ala Pro Leu Asp Val Phe Ile Pro Ala Gly Asn Thr Gly Met
                115                 120                 125

Glu Pro Gly Lys Thr Ser Phe Phe Gln Ala Leu Gly Val Pro Thr Lys
                130                 135                 140
```

```
Ile Ser Arg Gly Thr Ile Glu Ile Thr Ser Asp Val Lys Val Val Glu
145                 150                 155                 160

Lys Asp Ser Arg Val Gly Pro Ser Glu Ala Gln Leu Leu Asn Met Leu
            165                 170                 175

Asn Ile Ser Pro Phe Thr Tyr Gly Leu Thr Val Val Gln Val Phe Asp
        180                 185                 190

Asp Gly Gln Val Phe Pro Ala Asn Ile Leu Asp Ile Thr Asp Asp Glu
    195                 200                 205

Leu Leu Ser His Phe Thr Ser Ala Ile Ser Thr Ile Ala Gln Ile Ser
210                 215                 220

Leu Ala Ala Gly Tyr Pro Thr Leu Pro Ser Val Gly His Ser Val Val
225                 230                 235                 240

Asn His Tyr Lys Asn Val Leu Ala Val Ser Ile Ala Thr Asp Tyr Ser
            245                 250                 255

Phe Glu Gly Ser Glu Ala Ile Lys Asp Arg Leu Ala Asn Pro Glu Ala
        260                 265                 270

Tyr Ala Ala Ala Pro Ala Ala Gly Glu Ala Ser Ala Gly Ala Glu
    275                 280                 285

Glu Thr Ala Ala Ala Ala Glu Glu Asp Glu Glu Ser Glu Asp Asp
290                 295                 300

Asp Met Gly Phe Gly Leu Phe Asp
305                 310

<210> SEQ ID NO 7
<211> LENGTH: 499
<212> TYPE: PRT
<213> ORGANISM: Pichia pastoris

<400> SEQUENCE: 7

Met Ala Arg Lys Thr Leu Ala Glu Thr Leu Ala Glu Leu Ser Gln Pro
1               5                   10                  15

Ala Ser Gly Asp Phe Asp Ile Glu Asp Gln Glu Gly Gly Ala Val Leu
            20                  25                  30

Asp Tyr Gly Asp Asn Ser Ser Phe Gly Ser Glu Ser Glu Glu Asp Lys
        35                  40                  45

Ser Asn His Tyr Val Lys Val Gly Lys Ser Arg Ile Arg Glu Asn Ala
50                  55                  60

Val Lys Leu Gly Gly Gln Tyr Glu Gly Lys Lys Ser Ser Arg Ala Asp
65                  70                  75                  80

Val Phe Gly Asp Glu Asp Glu Glu Asp Asp Glu Asp Val Glu
            85                  90                  95

His Ser Glu Thr Glu Asp Ala Leu Ser Val Ser Gly Ser Glu Ser Glu
            100                 105                 110

Ser Asp Glu Lys Asn Ser Asp Gln Ser Gln Gly Asp Ser Glu Ser Glu
        115                 120                 125

Glu Glu Ser Asn Ser Gly Glu Asp Leu Asp Tyr Lys Arg Ser Lys Leu
    130                 135                 140

Gln Gln Leu Ile Ser Ser Glu Arg Lys Thr Ile Val Asn Gln Leu Ser
145                 150                 155                 160

Thr Ser Asn Lys Gln Asp Ala Leu Lys Gly Phe Ala Val Leu Asn Gln
            165                 170                 175

Gln Lys Gln Tyr Asp Gln Leu Val Asp Leu Arg Ile Lys Leu Gln Lys
        180                 185                 190

Gly Leu Val Ala Ser Asn Gly Leu Pro Ile Asn Lys Glu Tyr Tyr Glu
    195                 200                 205
```

Gln Asn Lys Ala Pro Lys Ser Ser Lys His Leu Asp Lys Leu Gln Asp
            210                 215                 220

Lys Leu Tyr Asn Leu Leu Asp Val Thr Leu Glu Leu Arg Gly Lys Leu
225                 230                 235                 240

Leu Asn Lys Ser Lys Ile Val Ser Gln Glu Phe Pro Pro Ile Pro Ser
                245                 250                 255

Lys Lys Arg Ser Leu Gln His Tyr Leu Glu Glu Ser Ser Lys Leu Asp
            260                 265                 270

Asn Ile Val Asn Glu Tyr Arg Arg Asn Val Leu Val Lys Trp Ser Gln
            275                 280                 285

Lys Val Gln Asn Ala Ser Gly Ala Thr Ala Leu Ser Ser Ser Lys Phe
            290                 295                 300

Lys Ala Ile Asn Gln Asp Ser Ser Thr Gln Val Asp Asn Tyr Leu Ala
305                 310                 315                 320

Asp Met Asp Arg Leu Ile Lys Arg Thr Arg Leu Asn Arg Arg Ser Val
            325                 330                 335

Val Pro Leu Gly Tyr Thr Glu Thr Glu Val Val Asp Asp Asp Glu
            340                 345                 350

Leu Ile Asp Asn Asp Lys Asp Asn Asn Glu Thr Lys Tyr Phe Ser Asn
            355                 360                 365

Ile Asp Arg Ser Leu Lys Glu Asn Lys Tyr Ile Tyr Asp Asp Asp
370                 375                 380

Phe Tyr Arg Val Leu Leu Asn Asp Leu Val Asp Lys Lys Val Ser Asp
385                 390                 395                 400

Thr Gln Lys Leu Thr Ser Thr Ser Thr Val Ile Thr Phe Ser Lys Ser
                405                 410                 415

Lys Leu His Lys Ser Tyr Glu Arg Lys Ala Thr Lys Gly Arg Lys Leu
            420                 425                 430

Arg Tyr Thr Val Gln Asp Pro Leu Leu Asn Phe Glu Ala Ser Asn Pro
            435                 440                 445

His Ala Tyr Lys Trp Asn Asp Tyr Gln Ile Asp Glu Phe Phe Ala Ser
450                 455                 460

Leu Phe Gly Gln Lys Val Asn Met Asn Glu Asp Glu His Asn Glu Glu
465                 470                 475                 480

Val Gln Gly Glu Ser Glu Gly Glu Asp Ile Leu Lys Asp Asp Ile Lys
                485                 490                 495

Leu Phe Gly

<210> SEQ ID NO 8
<211> LENGTH: 257
<212> TYPE: PRT
<213> ORGANISM: Pichia pastoris

<400> SEQUENCE: 8

Met Ser Arg Glu Asp Ser Val Tyr Leu Ala Lys Leu Ala Glu Gln Ala
1               5                   10                  15

Glu Arg Tyr Glu Glu Met Val Glu Asn Met Lys Thr Val Ala Ser Ser
                20                  25                  30

Gly Leu Glu Leu Ser Val Glu Glu Arg Asn Leu Leu Ser Val Ala Tyr
            35                  40                  45

Lys Asn Val Ile Gly Ala Arg Arg Ala Ser Trp Arg Ile Val Ser Ser
50                  55                  60

Ile Glu Gln Lys Glu Glu Ala Lys Gly Asn Gln Ser Gln Val Ser Leu
65                  70                  75                  80

-continued

Ile Arg Glu Tyr Arg Ser Lys Ile Glu Thr Glu Leu Ala Asn Ile Cys
                85                  90                  95

Glu Asp Ile Leu Ser Val Leu Ser Glu His Leu Ile Pro Ser Ala Arg
            100                 105                 110

Thr Gly Glu Ser Lys Val Phe Tyr Phe Lys Met Lys Gly Asp Tyr His
        115                 120                 125

Arg Tyr Leu Ala Glu Phe Ala Val Gly Asp Lys Arg Lys Glu Ala Ala
    130                 135                 140

Asn Leu Ser Leu Glu Ala Tyr Lys Ser Ala Ser Asp Val Ala Val Thr
145                 150                 155                 160

Glu Leu Pro Pro Thr His Pro Ile Arg Leu Gly Leu Ala Leu Asn Phe
                165                 170                 175

Ser Val Phe Tyr Tyr Glu Ile Leu Asn Ser Pro Asp Arg Ala Cys His
            180                 185                 190

Leu Ala Lys Gln Ala Phe Asp Asp Ala Ile Ala Glu Leu Glu Thr Leu
        195                 200                 205

Ser Glu Glu Ser Tyr Lys Asp Ser Thr Leu Ile Met Gln Leu Leu Arg
    210                 215                 220

Asp Asn Leu Thr Leu Trp Thr Ser Asp Met Ser Glu Thr Gly Gln Glu
225                 230                 235                 240

Glu Ser Ser Asn Ser Gln Asp Lys Thr Glu Ala Ala Pro Lys Asp Glu
                245                 250                 255

Glu

<210> SEQ ID NO 9
<211> LENGTH: 525
<212> TYPE: PRT
<213> ORGANISM: Pichia pastoris

<400> SEQUENCE: 9

Met Ser Val Asn Ile Leu Gly Asp Gln Val Ser Glu Glu Arg Ala Glu
1               5                   10                  15

Asn Ala Arg Leu Ser Ala Phe Val Gly Ala Ile Ala Val Gly Asp Leu
            20                  25                  30

Val Lys Thr Thr Leu Gly Pro Lys Gly Met Asp Lys Leu Leu Thr Ser
        35                  40                  45

Ala Ser Ser Gly Gln Ser Ile Val Thr Asn Asp Gly Ala Thr Ile Leu
    50                  55                  60

Lys Ser Ile Pro Leu Asp Asn Pro Ala Ala Lys Val Leu Val Asn Leu
65                  70                  75                  80

Ser Lys Val Gln Asp Asp Glu Val Gly Asp Gly Thr Thr Ser Val Thr
                85                  90                  95

Val Leu Ala Ser Glu Leu Leu Arg Glu Ala Glu Lys Leu Val Asp Arg
            100                 105                 110

Lys Ile His Pro Gln Thr Ile Ile Glu Gly Phe Arg Ile Ala Ser Lys
        115                 120                 125

Ala Ala Leu Glu Ala Leu Asp Lys Val Ala Val Asp Asn Ser His Asp
    130                 135                 140

Asp Ala Ala Phe Arg Lys Asp Leu Ile Asn Ile Ala Lys Thr Thr Leu
145                 150                 155                 160

Ser Ser Lys Ile Leu Ala Gln Asp Arg Asp Lys Phe Ala Glu Ile Ala
                165                 170                 175

Val Ser Ala Ile Leu Arg Leu Arg Gly Ser Thr Ser Leu Glu Arg Ile
            180                 185                 190

Gln Leu Ile Lys Ile Ile Gly Gly Gln Leu Ser Asp Ser Tyr Leu Asp
            195                 200                 205

Asp Gly Phe Ile Leu Asn Lys Lys Phe Gly Leu Asp Gln Pro Lys Lys
    210                 215                 220

Ile Lys Asp Ala Ser Ile Leu Ile Ala Asn Thr Ser Met Asp Thr Asp
225                 230                 235                 240

Lys Val Lys Ile Phe Gly Ala Lys Phe Lys Val Asp Ser Thr Ser Lys
                245                 250                 255

Leu Ala Gln Leu Glu Lys Ala Glu Lys Asp Lys Met Lys Ala Lys Val
            260                 265                 270

Glu Lys Ile Lys Asn Phe Asn Ile Asn Cys Phe Val Asn Arg Gln Leu
        275                 280                 285

Ile Tyr Asp Trp Pro Glu Gln Leu Leu Ala Asp Ser Asn Ile Asn Thr
    290                 295                 300

Ile Glu His Ala Asp Phe Asp Gly Val Glu Arg Leu Ala Leu Val Thr
305                 310                 315                 320

Gly Gly Glu Val Val Ser Thr Phe Asp Tyr Pro Gly Lys Val Lys Leu
                325                 330                 335

Gly Lys Cys Asp Leu Ile Glu Val Ile Ile Gly Glu Glu Val Met
            340                 345                 350

Thr Arg Phe Ser Gly Val Ser Glu Gly Ala Ala Cys Thr Ile Ile Leu
        355                 360                 365

Arg Gly Ala Thr Glu Gln Val Leu Asp Glu Ala Glu Arg Ser Leu His
    370                 375                 380

Asp Ala Leu Ser Val Leu Ser Gln Thr Thr Lys Glu Thr Arg Thr Val
385                 390                 395                 400

Leu Gly Gly Gly Cys Ser Glu Met Ile Met Ser Asn Ala Val Asp Thr
                405                 410                 415

Gln Ala Gln Asn Gln Glu Gly Lys Lys Gln Leu Ala Val Glu Ala Phe
            420                 425                 430

Ala Arg Ala Leu Arg Gln Leu Pro Thr Ile Leu Ala Asp Asn Ala Gly
        435                 440                 445

Tyr Asp Ser Ser Glu Leu Val Ala Arg Leu Arg Ser Ala Ile Tyr Ser
    450                 455                 460

Gly Leu Thr Thr Ser Gly Leu Asn Leu Ser Asn Gly Thr Val Gly Asp
465                 470                 475                 480

Met Arg Gln Leu Gly Val Met Glu Ser Tyr Lys Leu Lys Arg Ala Val
                485                 490                 495

Val Asn Ser Ala Ser Glu Ala Ala Glu Val Leu Leu Arg Val Asp Asn
            500                 505                 510

Ile Ile Arg Ala Lys Pro Arg Thr Ala Asp Arg Asn Arg
        515                 520                 525

<210> SEQ ID NO 10
<211> LENGTH: 299
<212> TYPE: PRT
<213> ORGANISM: Pichia pastoris

<400> SEQUENCE: 10

Met Lys Leu His Leu Val Ile Leu Cys Leu Ile Thr Ala Val Tyr Cys
1               5                   10                  15

Phe Ser Ala Val Asp Arg Glu Ile Phe Gln Leu Asn His Glu Leu Arg
            20                  25                  30

Gln Glu Tyr Gly Asp Asn Phe Asn Phe Tyr Glu Trp Leu Lys Leu Pro

```
            35                  40                  45
Lys Gly Pro Ser Ser Thr Phe Glu Asp Ile Asp Asn Ala Tyr Lys Lys
 50                  55                  60

Leu Ser Arg Lys Leu His Pro Asp Lys Ile Arg Gln Lys Lys Leu Ser
 65                  70                  75                  80

Gln Glu Gln Phe Glu Gln Leu Lys Lys Lys Ala Thr Glu Arg Tyr Gln
                 85                  90                  95

Gln Leu Ser Ala Val Gly Ser Ile Leu Arg Ser Glu Ser Lys Glu Arg
            100                 105                 110

Tyr Asp Tyr Phe Val Lys His Gly Phe Pro Val Tyr Lys Gly Asn Asp
        115                 120                 125

Tyr Thr Tyr Ala Lys Phe Arg Pro Ser Val Leu Leu Thr Ile Phe Ile
    130                 135                 140

Leu Phe Ala Leu Ala Thr Leu Thr His Phe Val Phe Ile Arg Leu Ser
145                 150                 155                 160

Ala Val Gln Ser Arg Lys Arg Leu Ser Ser Leu Ile Glu Glu Asn Lys
                165                 170                 175

Gln Leu Ala Trp Pro Gln Gly Val Gln Asp Val Thr Gln Val Lys Asp
            180                 185                 190

Val Lys Val Tyr Asn Glu His Leu Arg Lys Trp Phe Leu Val Cys Phe
        195                 200                 205

Asp Gly Ser Val His Tyr Val Glu Asn Asp Lys Thr Phe His Val Asp
    210                 215                 220

Pro Glu Glu Val Glu Leu Pro Ser Trp Gln Asp Thr Leu Pro Gly Lys
225                 230                 235                 240

Leu Ile Val Lys Leu Ile Pro Gln Leu Ala Arg Lys Pro Arg Ser Pro
                245                 250                 255

Lys Glu Ile Lys Lys Glu Asn Leu Asp Asp Lys Thr Arg Lys Thr Lys
            260                 265                 270

Lys Pro Thr Gly Asp Ser Lys Thr Leu Pro Asn Gly Lys Thr Ile Tyr
        275                 280                 285

Lys Ala Thr Lys Ser Gly Gly Arg Arg Lys
    290                 295

<210> SEQ ID NO 11
<211> LENGTH: 118
<212> TYPE: PRT
<213> ORGANISM: Pichia pastoris

<400> SEQUENCE: 11

Met Ser Glu Gly Lys Pro Asn Pro Asn Gln Glu Leu Phe Gln Lys Gln
  1               5                  10                  15

Tyr Asp Glu Phe Gln Glu Thr Leu Glu Ala Leu Asn Asn Lys Ile Gly
                 20                  25                  30

Gln Leu Gln Gly Asp Ile Glu Glu His Asn Ile Val Leu Lys Thr Ile
             35                  40                  45

Thr Thr Ala Pro Lys Asp Arg Lys Cys Phe His Met Ile Gly Gly Val
     50                  55                  60

Leu Ile Glu Lys Thr Ala Gly Glu Val Glu Pro Thr Leu Lys Thr Asn
 65                  70                  75                  80

Val Thr Lys Met Asn Asp Ala Val Glu Asn Leu Lys Asn Glu Ile Gln
                 85                  90                  95

Asn Thr His Lys Gln Phe Glu Asp Trp Lys Lys Thr Gly Val Lys
            100                 105                 110
```

```
Ile Val Ser Ala Asn Glu
        115
```

<210> SEQ ID NO 12
<211> LENGTH: 1106
<212> TYPE: PRT
<213> ORGANISM: Pichia pastoris

<400> SEQUENCE: 12

```
Met Asp Arg Glu Gln Gly Ile Leu Pro Gln Asp Pro Phe Ser Asn Ser
1               5                   10                  15

Val His Val Pro Lys Leu Arg Ala Ser Ser Gly Gly Gln Pro Gln Lys
            20                  25                  30

Pro Val Ile Gln Asn Ser Ala Pro Ala Thr Ala Arg Met Leu Arg Asn
        35                  40                  45

Ala Ser Ser Thr Ser Ala Ala Leu Leu Lys Glu Leu Asn Thr His
    50                  55                  60

Glu His Ser Gln Arg Gln His Thr Pro Gln Lys Gln Pro Ser Leu Asp
65                  70                  75                  80

Ala Pro Ala Ala Leu Val Pro Val Glu Ser Ala Thr Lys Gln Phe His
                85                  90                  95

Arg Thr Ser Ile Gly Asp Trp Glu Phe Ser Asn Thr Ile Gly Ala Gly
            100                 105                 110

Ser Met Gly Lys Val Lys Val Ala Lys His Arg Val Thr His Glu Val
        115                 120                 125

Cys Ala Ile Lys Ile Val Arg Ser Ala Lys Ile Trp Gln Arg Asn
    130                 135                 140

His Gln Asn Asp Pro Glu Pro Glu Thr Glu Glu Lys Arg Lys Lys Leu
145                 150                 155                 160

Arg Asp Glu Tyr Lys Lys Glu Leu Glu Arg Asp Glu Arg Thr Val Arg
                165                 170                 175

Glu Ala Ala Leu Gly Lys Ile Met Tyr His Pro Asn Ile Cys Arg Leu
            180                 185                 190

Phe Glu Cys Tyr Thr Met Ser Asn His Tyr Tyr Met Leu Phe Glu Ile
        195                 200                 205

Val Gln Gly Val Gln Leu Leu Asp Tyr Ile Val Ser His Gly Lys Leu
    210                 215                 220

Lys Glu Thr Arg Val Arg Gln Phe Ala Arg Ser Ile Ala Ser Ala Leu
225                 230                 235                 240

Asp Tyr Cys His Ser Asn Asn Ile Val His Arg Asp Leu Lys Ile Glu
                245                 250                 255

Asn Ile Met Ile Asn Asn Lys Gly Glu Ile Lys Leu Ile Asp Phe Gly
            260                 265                 270

Leu Ser Asn Met Tyr Asp Arg Arg Asn Leu Leu Lys Thr Phe Cys Gly
        275                 280                 285

Ser Leu Tyr Phe Ala Ala Pro Glu Leu Leu Ser Cys Arg Pro Tyr Ile
    290                 295                 300

Gly Pro Glu Ile Asp Val Trp Ser Phe Gly Val Val Leu Phe Val Leu
305                 310                 315                 320

Val Ser Gly Lys Val Pro Phe Asp Asp Ser Val Pro Lys Leu His
                325                 330                 335

Ala Lys Ile Lys Arg Gly Lys Val Glu Tyr Pro Glu Phe Ile Ser Pro
            340                 345                 350

Leu Cys His Ser Leu Leu Ser Gln Met Leu Val Val Asn Pro Asp His
        355                 360                 365
```

```
Arg Val Thr Leu Lys Ala Ala Met Glu His Pro Trp Met Thr Leu Gly
    370                 375                 380

Phe Ala Gly Pro Pro Ser Asn Tyr Leu Pro Gln Arg Ser Pro Ile Val
385                 390                 395                 400

Leu Pro Leu Asp Leu Ser Val Val Arg Glu Ile Ala Asn Leu Gly Leu
                405                 410                 415

Gly Asn Glu Glu Gln Ile Ala Arg Asp Ile Thr Asn Leu Ile Ser Ser
                420                 425                 430

Arg Glu Tyr Glu Ala Cys Val Glu Arg Trp Lys Leu Asp Gln Gln Lys
                435                 440                 445

Ala Asn Ile Lys Gly Tyr Ser Ala Arg Asp Ser Ala Ile Ile Ala
    450                 455                 460

Phe His Pro Leu Leu Ser Thr Tyr Tyr Leu Val Asp Glu Met Arg Lys
465                 470                 475                 480

Arg Lys Leu Ala Lys Gly Ala Leu Lys Gly Gln Thr Ser Val Leu Asp
                485                 490                 495

Thr Val Lys Val Ser Pro Asp Ile Pro Lys Thr Pro Ala Ile Pro Gln
                500                 505                 510

Lys Leu Glu Thr Thr Asp Val Glu Gln Pro Leu Leu Ala Thr Val Pro
    515                 520                 525

Pro Ala Tyr Thr Ser Pro His Gly Gln Pro Ala Glu Leu Glu Ala Met
    530                 535                 540

Ile Glu Pro Ala Gln Pro Leu Ser Ser Ala His Pro Phe Glu Met Asp
545                 550                 555                 560

Met Thr Gln Gln Gln His Ala Ser Arg Lys Thr His Ile Lys His Ala
                565                 570                 575

Pro Glu Arg Gln Asp Arg Gly Gly Tyr Asn Val His Lys Asn Asn Ser
                580                 585                 590

Gly Gly Leu Asn Ser Leu Phe Arg Arg Leu Ser Gly Lys Arg Pro His
                595                 600                 605

Lys Asn Glu Ala Glu Trp Glu Pro Ser Ser Pro Pro Gln Val His
    610                 615                 620

Pro Phe Ser Val Asn Asp Ala Asp Arg Thr Ser Val Arg Gly Val Ser
625                 630                 635                 640

Pro Ile Thr Gln Pro Ala Ala Val Lys Asn Val Thr Ser Asn Asn Ser
                645                 650                 655

Lys Asn Tyr Leu Asp Pro Val Asp Asp Ser Lys Leu Val Arg Arg Val
                660                 665                 670

Gly Ser Leu Arg Ile Thr Asn Lys Glu Lys Gln Val Thr Ser Asp
    675                 680                 685

Phe Pro Arg Leu Pro Asn Phe Thr Ile Pro Glu Gln Pro Pro Lys Asn
690                 695                 700

Ala Pro Ile Pro Ile His Ala Gln Pro Thr Thr Thr Gly Thr Thr Phe
705                 710                 715                 720

Gln Ser Asn Asp His Glu Ile Lys Lys Leu Gln Ala Ser Thr Ser
                725                 730                 735

Pro Asn Glu Gln Arg Gly Pro Pro Thr Leu Ala Pro Ser Gln Gln Arg
                740                 745                 750

Arg Leu His Pro Thr Ala Arg Ala Lys Ser Leu Gly His Ser Arg Lys
                755                 760                 765

Gln Ser Leu Asn Phe Lys Phe Gly Gly Pro Ala Asn Asn Gln Leu Pro
    770                 775                 780
```

Ala Leu Pro Thr Lys Glu Asn Tyr Asp Val Phe Glu Asp Ala Gln Ile
785                 790                 795                 800

Thr Asp Asn Asn Leu Leu Asn Pro Glu Gly Lys Tyr Ser Ala Asn Thr
            805                 810                 815

Asn Val His Ile Lys Pro Met Thr Glu Ser Gln Ile Leu Phe Glu Ala
        820                 825                 830

Glu His Ala Pro Pro Gly Thr Met Pro Ser Val Glu Tyr Pro Arg Thr
    835                 840                 845

Leu Phe Leu Lys Gly Phe Phe Ser Val Gln Thr Thr Ser Ser Lys Pro
850                 855                 860

Leu Pro Val Ile Arg Tyr Asn Ile Ile Ala Ala Leu Cys Lys Leu Asn
865                 870                 875                 880

Ile Gln Phe Thr Glu Val Asn Gly Gly Phe Val Cys Val Tyr Arg Lys
            885                 890                 895

Thr Glu Asn Leu Gln Ile Gly Asp Ile Arg Ser Pro Val Ile Glu Ser
        900                 905                 910

Arg Val Thr Asp Asp Thr Asp Ser Asp Val Ala Asn Ser Ser Lys Leu
    915                 920                 925

Ser Ser Ser Ser Thr Ala Asn Thr Arg Val Asn Val Ile Glu Asp Asp
930                 935                 940

Ser Ser Pro Ser Ser Ala Arg Leu Lys His Arg Lys Phe Ser
945                 950                 955                 960

Leu Gly Asn Gly Ile Leu Asn His Ile Arg Lys Pro Thr Leu Asp Gly
            965                 970                 975

Thr Glu Phe Asp Asp Tyr Asp Ala Thr Val Asn Thr Pro Val Thr Pro
        980                 985                 990

Ala Pro Ala Asn Val His Ser Arg  Ser Ser Ser Tyr His  Thr Glu Ser
    995                 1000                1005

Asp Asn  Glu Ser Met Glu Ser  Leu His Asp Ile Arg  Gly Gly Ser
    1010                1015                1020

Asp Met  Ile Leu Lys Asn Val  Pro Glu Arg Asn Ala  Arg Gln Ile
    1025                1030                1035

Asp Thr  Val Lys Glu Glu Glu  Thr Asp Asp Asp  Leu Gly Ser
    1040                1045                1050

Ile Asn  Glu Gly Ser Thr His  Arg Thr Pro Leu Lys  Phe Glu Ile
    1055                1060                1065

His Ile  Val Lys Val Pro Leu  Val Gly Leu Tyr Gly  Val Arg Phe
    1070                1075                1080

Lys Lys  Ile Leu Gly Asn Ala  Trp Ile Tyr Lys Arg  Leu Ala Ser
    1085                1090                1095

Lys Leu  Leu Gln Glu Leu Asn  Leu
    1100                1105

<210> SEQ ID NO 13
<211> LENGTH: 492
<212> TYPE: PRT
<213> ORGANISM: Pichia pastoris

<400> SEQUENCE: 13

Met Ser Gln Arg Phe Leu Gln Gly Met Asn Arg Arg Leu Pro His Leu
1               5                   10                  15

Val Trp Leu Arg Thr Lys Gln Pro Leu Leu Ser Cys Ala Phe Gln Arg
            20                  25                  30

His Pro Leu Ser Lys Tyr Gln Ala Arg Gly Phe His Gly Ser Ala Ala
        35                  40                  45

```
Arg Leu Ile Ser Asp Pro Tyr Lys Thr Leu Asn Val Asp Arg Asn Ala
     50                  55                  60
Ser Thr Ser Asp Ile Lys Lys Ala Tyr Tyr Lys Leu Ala Lys Gln Tyr
 65                  70                  75                  80
His Pro Asp Ile Asn Lys Glu Lys Gly Ala Glu Lys Lys Phe His Asp
                 85                  90                  95
Ile Gln Ala Ala Tyr Glu Ile Leu Ser Asp Thr Glu Lys Lys Gln Gln
            100                 105                 110
Phe Asp Gln Phe Gly Thr Val Phe Asp Ser Asp Gly Asn Pro Met Gly
        115                 120                 125
Gly Ser Gly Gly Arg Gly Gly Pro Gly Asn Pro Phe Ala Gly Gly Asn
    130                 135                 140
Pro Phe Gly Ala Gly Asn Pro Phe Gly Asn Ala Ala Gly Gly Phe Ser
145                 150                 155                 160
Phe Asn Leu Glu Asp Leu Phe Gly Asp Ala Phe Asn Gly Ala Asn Arg
                165                 170                 175
Gln Gly Gly Arg Arg Ala Gly Gly Ala Ala Tyr Met Glu Gln Tyr Gln
            180                 185                 190
Gly Asn Asp Val Glu Ile Leu Lys Thr Ile Ser Phe Lys Glu Ser Ile
    195                 200                 205
Phe Gly Thr Asn Ala Ser Val Asn Tyr Asn Val Leu Asp Gly Cys Asn
210                 215                 220
Thr Cys Glu Gly Thr Gly Leu Lys Lys Gly Arg Lys Lys Ser Thr Cys
225                 230                 235                 240
Ser Thr Cys Asn Gly Ser Gly Ala Ser Val His Tyr Leu Gln Gly Phe
                245                 250                 255
Gln Met Ser Ser Thr Cys Asn Ala Cys Gly Gly Thr Gly Val Thr Ile
            260                 265                 270
Ser Lys Asp Asp Gln Cys Gly His Cys His Gly Asn Gly Val Gly Gln
    275                 280                 285
Ser Ser Lys Thr Thr Glu Val Lys Leu Pro Cys Gly Ile Arg Asp Gly
290                 295                 300
Thr Arg Leu Arg Val Ser Gly Ala Gly Asp Ala Pro Asn Val Thr Lys
305                 310                 315                 320
Gly Pro Asn Val Arg Thr Val Lys Gly Asp Leu Ile Ile Arg Val Arg
                325                 330                 335
Val Lys Pro Asp Pro Arg Tyr Ser Arg Asp Gly Asn Asp Ile Val Tyr
            340                 345                 350
Asn Cys Glu Ile Pro Met Thr Thr Ala Ala Leu Gly Gly Gln Val Glu
    355                 360                 365
Ile Pro Thr Leu Asp Asp Thr Lys Leu Arg Leu Lys Val Pro Ile Gly
370                 375                 380
Thr Gln His Gly Arg Thr Val Ser Ile Pro Gly Gln Gly Val Pro Ile
385                 390                 395                 400
His Gly Ser Leu Ser Asn Arg Gly Ala Leu Lys Val Gln Phe Asn Val
                405                 410                 415
Lys Val Leu Arg Pro Asp Asn Ala Thr Gln Thr Ala Leu Leu Glu Ala
            420                 425                 430
Leu Ala Asp Thr Phe Asn Asp Thr Thr Ala Lys Lys Val Asn Pro Ser
        435                 440                 445
Trp Lys Pro Phe Glu Asn Ser Ala Pro Pro Ala Glu Gly Glu Asp Ser
450                 455                 460
```

Asp His Pro Ser Arg Leu Lys Lys Ile Glu Ser Phe Leu Ser Asp Ala
465                 470                 475                 480

Phe Lys Arg Ile Thr Asn Lys Lys Asp Asp Cys Lys
                485                 490

<210> SEQ ID NO 14
<211> LENGTH: 304
<212> TYPE: PRT
<213> ORGANISM: Pichia pastoris

<400> SEQUENCE: 14

Met Pro Val Asp Ser Ser His Lys Thr Ala Ser Pro Leu Pro Pro Arg
1               5                   10                  15

Lys Arg Ala Lys Thr Glu Glu Lys Glu Gln Arg Arg Val Glu Arg
            20                  25                  30

Ile Leu Arg Asn Arg Arg Ala Ala His Ala Ser Arg Glu Lys Lys Arg
        35                  40                  45

Arg His Val Glu Phe Leu Glu Asn His Val Val Asp Leu Glu Ser Ala
    50                  55                  60

Leu Gln Glu Ser Ala Lys Ala Thr Asn Lys Leu Lys Glu Ile Gln Asp
65                  70                  75                  80

Ile Ile Val Ser Arg Leu Glu Ala Leu Gly Gly Thr Val Ser Asp Leu
                85                  90                  95

Asp Leu Thr Val Pro Glu Val Asp Phe Pro Lys Ser Ser Asp Leu Glu
            100                 105                 110

Pro Met Ser Asp Leu Ser Thr Ser Ser Lys Ser Glu Lys Ala Ser Thr
        115                 120                 125

Ser Thr Arg Arg Ser Leu Thr Glu Asp Leu Asp Glu Asp Val Ala
130                 135                 140

Glu Tyr Asp Asp Glu Glu Glu Asp Glu Glu Leu Pro Arg Lys Met Lys
145                 150                 155                 160

Val Leu Asn Asp Lys Asn Lys Ser Thr Ser Ile Lys Gln Glu Lys Leu
                165                 170                 175

Asn Glu Leu Pro Ser Pro Leu Ser Ser Asp Phe Ser Asp Val Asp Glu
            180                 185                 190

Glu Lys Ser Thr Leu Thr His Leu Lys Leu Gln Gln Gln Gln Gln
        195                 200                 205

Pro Val Asp Asn Tyr Val Ser Thr Pro Leu Ser Leu Pro Glu Asp Ser
210                 215                 220

Val Asp Phe Ile Asn Pro Gly Asn Leu Lys Ile Glu Ser Asp Glu Asn
225                 230                 235                 240

Phe Leu Leu Ser Ser Asn Thr Leu Gln Ile Lys His Glu Asn Asp Thr
                245                 250                 255

Asp Tyr Ile Thr Thr Ala Pro Ser Gly Ser Ile Asn Asp Phe Phe Asn
            260                 265                 270

Ser Tyr Asp Ile Ser Glu Ser Asn Arg Leu His His Pro Ala Ala Pro
        275                 280                 285

Phe Thr Ala Asn Ala Phe Asp Leu Asn Asp Phe Val Phe Gln Glu
290                 295                 300

<210> SEQ ID NO 15
<211> LENGTH: 632
<212> TYPE: PRT
<213> ORGANISM: Pichia pastoris

<400> SEQUENCE: 15

```
Met Ser Glu Arg Ser Ser Lys Lys Gly Pro Lys Gly Gly Ala Lys Arg
1               5                   10                  15

Ser Ser Gln Gly Ser Ser Gln Gly Leu Glu Ser Thr Lys Leu Ala Thr
            20                  25                  30

Leu Thr Glu Leu Phe Pro Asp Trp Thr Ala Gln Asp Leu Glu Pro Val
        35                  40                  45

Leu Glu Glu Tyr Pro Asp Glu Asp Leu Asn Val Ile Ile Glu Asn Ile
    50                  55                  60

Ile Ser Gly Lys Ile Asn Lys Trp Thr Asp Pro Ser Ala Lys Lys Glu
65                  70                  75                  80

Lys Lys Lys Arg Glu Glu Ser Phe Asn Ala Ser Glu Glu Leu Ser Thr
                85                  90                  95

Pro Ser Tyr His Gln Thr Pro Asn Ser Ala Lys Lys Glu Tyr Pro Lys
            100                 105                 110

Lys Glu Val Lys Ala Lys Ser Lys Lys Ser Gln Pro Arg Ser Thr Thr
        115                 120                 125

Ser Thr Thr Thr Ala Ser Thr Lys Ala Gln Leu Thr Pro Ser Ser Asn
    130                 135                 140

Pro Ser Thr Lys Ser Ser Trp Ala Ala Ala Leu His Gln Lys Gln Glu
145                 150                 155                 160

Asp Lys Pro Ser Ser Thr Val Thr Pro Thr Thr Glu Thr Glu Thr Pro
            165                 170                 175

Asn Gly Glu Asn Ala Ser Gln Ser Pro Val Ala Glu Thr Lys Ser Glu
            180                 185                 190

Gln Glu Glu Ser Phe Ala Pro Ala Ala Val Glu Thr Ser Ala Lys
        195                 200                 205

Pro Lys Ser Trp Ala Ala Met Val Ala Gln Ser Ala Lys Pro Lys Lys
210                 215                 220

Lys Ile Leu Lys Arg Pro Glu Gln Ala Ala Lys Pro Ser Ser Asn Glu
225                 230                 235                 240

Glu Leu Ser Gln Gln Asn Gly Glu Ile Gln Asp Glu Gln Gln Ser Leu
            245                 250                 255

Gln Thr Gln Ala Glu Thr Gln Ala Glu Gln Pro Ile Gln Ser Ile Glu
            260                 265                 270

Leu Gln Gln Thr Asn Glu Gln Ile Ser Gln Glu Gln Lys Pro Val
            275                 280                 285

Gln Glu Pro Lys Pro Leu Glu Arg Lys Gln Gln Gln Gln Gln Gln Gln
        290                 295                 300

Gln Pro Val Val Leu Pro Ser Ala Val Asn Leu Asp Ser Ile Gly Gly
305                 310                 315                 320

Ile Ser Phe Gly Ser Leu Ser Leu Asn Glu Lys Glu Ala Ser Ser Ala
            325                 330                 335

Gln Gln Ala Gln Gln Ala Ser Gln Pro Thr Ser Gln Val Gln Ala Gln
            340                 345                 350

Thr Gln Asn Gln Gln Tyr Gln Arg Tyr Glu Asn Gln Tyr Tyr Asn Asn
            355                 360                 365

Asn Arg Gln Phe Tyr Gln Asp Gly Lys Gln Val Asn Tyr Asp Ser Phe
    370                 375                 380

Val Arg Gln Gln Gln Gln Gln Gln His Gln Gln Gln Tyr Trp
385                 390                 395                 400

Ala His Pro Gln Ala Gln Ala Gln Gly Val Ala Ser Ala Gly Gly Ser
            405                 410                 415

Asp Leu Asn Ser Ala Ser Pro Ala Ala Ser Asn Ala Leu Pro Gln Gly
```

```
                420             425             430
Gln Pro Gln Gly Thr Pro Ser Ala Ser Asn Ala Asn Pro Val Asn Ala
            435                 440                 445
Tyr Asn Asn Pro Gln Phe Tyr Thr Pro Tyr Val Tyr Tyr Pro Tyr Gly
        450                 455                 460
Gln Tyr Tyr Gln Asn Pro Gln Leu Tyr Ser Gly Tyr Met Gly Tyr Gly
465                 470                 475                 480
Ala Gly Gln Pro Gln Thr Gln Pro His Gln Pro Gln Val Pro Pro Thr
                485                 490                 495
Ala Ser Pro Ser Gln Gln Thr Gln Gln Val Gln Pro Thr Ser Gly Gln
            500                 505                 510
Val Pro Asn Gln Gln Leu Ala Gly Phe Gln Gly Tyr Gln Gln Pro Tyr
        515                 520                 525
Gln Gln Ala Tyr Leu Asn Lys Asn Gly Tyr Pro Leu Tyr Gln Gln Tyr
    530                 535                 540
Pro Gln Gln Gln Gln Gln Val Gly Gly Gly Gln Ser Gln Pro
545                 550                 555                 560
Gln Gly Lys Glu Val Glu Glu Pro Lys Pro Gln Gln Gly Gln Gln
                565                 570                 575
Ala Gly Gln His Gln Gly Gln Ala Gln Leu Pro Gln Gln Tyr Pro
            580                 585                 590
Gly His Pro Gly Gln Tyr Phe Gly Gln Gln Ala Leu Gly Ala Gln Gln
        595                 600                 605
Thr Pro Tyr Thr Glu Tyr Pro Val Tyr Pro Asn Ser Asn Asp Tyr Asn
    610                 615                 620
Asn Thr Asn Ala Lys Gly Trp Ile
625                 630

<210> SEQ ID NO 16
<211> LENGTH: 538
<212> TYPE: PRT
<213> ORGANISM: Pichia pastoris

<400> SEQUENCE: 16

Met Phe Lys Ser Leu Cys Met Leu Ile Gly Ser Cys Leu Leu Ser Ser
1               5                   10                  15
Val Leu Ala Ala Asp Phe Pro Thr Ile Glu Val Thr Gly Asn Lys Phe
            20                  25                  30
Phe Tyr Ser Asn Asn Gly Ser Gln Phe Tyr Ile Lys Gly Val Ala Tyr
        35                  40                  45
Gln Lys Asp Thr Ser Gly Leu Ser Ser Asp Ala Thr Phe Val Asp Pro
    50                  55                  60
Leu Ala Asp Lys Ser Thr Cys Glu Arg Asp Ile Pro Tyr Leu Glu Glu
65                  70                  75                  80
Leu Gly Thr Asn Val Ile Arg Val Tyr Ala Val Asp Ala Asp Ala Asp
                85                  90                  95
His Asp Asp Cys Met Gln Met Leu Gln Asp Ala Gly Ile Tyr Val Ile
            100                 105                 110
Ala Asp Leu Ser Gln Pro Asn Asn Ser Ile Ile Thr Thr Asp Pro Glu
        115                 120                 125
Trp Thr Val Asp Leu Tyr Asp Gly Tyr Thr Ala Val Leu Asp Asn Leu
    130                 135                 140
Gln Lys Tyr Asp Asn Ile Leu Gly Phe Phe Ala Gly Asn Glu Val Ile
145                 150                 155                 160
```

Thr Asn Lys Ser Asn Thr Asp Thr Ala Pro Phe Val Lys Ala Ala Ile
            165                 170                 175

Arg Asp Met Lys Thr Tyr Met Glu Asp Lys Gly Tyr Arg Ser Ile Pro
            180                 185                 190

Val Gly Tyr Ser Ala Asn Asp Asp Glu Leu Thr Arg Val Ala Ser Ala
            195                 200                 205

Asp Tyr Phe Ala Cys Gly Asp Ser Asp Val Lys Ala Asp Phe Tyr Gly
            210                 215                 220

Ile Asn Met Tyr Glu Trp Cys Gly Lys Ala Thr Phe Ser Asn Ser Gly
225                 230                 235                 240

Tyr Lys Asp Arg Thr Ala Glu Phe Lys Asn Leu Ser Ile Pro Val Phe
            245                 250                 255

Phe Ser Glu Tyr Gly Cys Asn Glu Val Gln Pro Arg Leu Phe Thr Glu
            260                 265                 270

Val Gln Ser Leu Tyr Gly Asp Asp Met Thr Asp Val Trp Ser Gly Gly
            275                 280                 285

Ile Val Tyr Met Tyr Phe Glu Glu Thr Asn Asn Tyr Gly Leu Val Thr
            290                 295                 300

Ile Lys Ser Asp Gly Asp Val Ser Thr Leu Glu Asp Phe Asn Asn Leu
305                 310                 315                 320

Lys Thr Glu Leu Ala Ser Ile Ser Pro Ser Ile Ala Thr Gln Ser Glu
            325                 330                 335

Val Ser Ala Thr Ala Thr Glu Ile Asp Cys Pro Ala Thr Gly Ser Asn
            340                 345                 350

Trp Lys Ala Ser Thr Asp Leu Pro Pro Val Pro Glu Gln Ala Ala Cys
            355                 360                 365

Gln Cys Met Ala Asp Ala Leu Ser Cys Val Val Ser Glu Asp Val Asp
            370                 375                 380

Thr Asp Asp Tyr Ser Asp Leu Phe Ser Tyr Val Cys Glu Asn Val Ser
385                 390                 395                 400

Ser Cys Asp Gly Val Ser Ala Asp Ser Glu Ser Gly Glu Tyr Gly Ser
            405                 410                 415

Tyr Ser Phe Cys Ser Ser Lys Glu Lys Leu Ser Phe Leu Leu Asn Leu
            420                 425                 430

Tyr Tyr Ser Glu Asn Gly Ala Lys Ser Ser Ala Cys Asp Phe Ser Gly
            435                 440                 445

Ser Ala Thr Leu Val Ser Gly Thr Ala Ser Glu Cys Ser Ser Ile
            450                 455                 460

Leu Ser Ala Ala Gly Thr Ala Gly Thr Gly Ser Ile Thr Gly Ile Thr
465                 470                 475                 480

Gly Ser Val Glu Ala Ala Thr Gln Ser Gly Ser Asn Ser Gly Ser Ser
            485                 490                 495

Lys Ser Ser Ser Ala Ser Gln Ser Ser Ser Asn Ala Gly Val Gly
            500                 505                 510

Gly Gly Ala Ser Gly Ser Ser Trp Ala Met Thr Gly Leu Val Ser Ile
            515                 520                 525

Ser Val Ala Leu Gly Met Ile Met Ser Phe
            530                 535

<210> SEQ ID NO 17
<211> LENGTH: 894
<212> TYPE: PRT
<213> ORGANISM: Pichia pastoris

<400> SEQUENCE: 17

```
Met Arg Thr Gln Lys Ile Val Thr Val Leu Cys Leu Leu Asn Thr
1               5                   10                  15

Val Leu Gly Ala Leu Leu Gly Ile Asp Tyr Gly Gln Glu Phe Thr Lys
        20                  25                  30

Ala Val Leu Val Ala Pro Gly Val Pro Phe Glu Val Ile Leu Thr Pro
            35                  40                  45

Asp Ser Lys Arg Lys Asp Asn Ser Met Met Ala Ile Lys Glu Asn Ser
    50                  55                  60

Lys Gly Glu Ile Glu Arg Tyr Tyr Gly Ser Ser Ala Ser Ser Val Cys
65                  70                  75                  80

Ile Arg Asn Pro Glu Thr Cys Leu Asn His Leu Lys Ser Leu Ile Gly
                85                  90                  95

Val Ser Ile Asp Asp Val Ser Thr Ile Asp Tyr Lys Lys Tyr His Ser
                100                 105                 110

Gly Ala Glu Met Val Pro Ser Lys Asn Asn Arg Asn Thr Val Ala Phe
            115                 120                 125

Lys Leu Gly Ser Ser Val Tyr Pro Val Glu Glu Ile Leu Ala Met Ser
    130                 135                 140

Leu Asp Asp Ile Lys Ser Arg Ala Glu Asp His Leu Lys His Ala Val
145                 150                 155                 160

Pro Gly Ser Tyr Ser Val Ile Ser Asp Ala Val Ile Thr Val Pro Thr
                165                 170                 175

Phe Phe Thr Gln Ser Gln Arg Leu Ala Leu Lys Asp Ala Ala Glu Ile
            180                 185                 190

Ser Gly Leu Lys Val Val Gly Leu Val Asp Asp Gly Ile Ser Val Ala
    195                 200                 205

Val Asn Tyr Ala Ser Ser Arg Gln Phe Asn Gly Asp Lys Gln Tyr His
    210                 215                 220

Met Ile Tyr Asp Met Gly Ala Gly Ser Leu Gln Ala Thr Leu Val Ser
225                 230                 235                 240

Ile Ser Ser Ser Asp Asp Gly Gly Ile Val Ile Asp Val Glu Ala Ile
                245                 250                 255

Ala Tyr Asp Lys Ser Leu Gly Gly Gln Leu Phe Thr Gln Ser Val Tyr
            260                 265                 270

Asp Ile Leu Leu Gln Lys Phe Leu Ser Glu His Pro Ser Phe Ser Glu
        275                 280                 285

Ser Asp Phe Asn Lys Asn Ser Lys Ser Met Ser Lys Leu Trp Gln Ala
    290                 295                 300

Ala Glu Lys Ala Lys Thr Ile Leu Ser Ala Asn Thr Asp Thr Arg Val
305                 310                 315                 320

Ser Val Glu Ser Leu Tyr Asn Asp Ile Asp Phe Arg Ala Thr Ile Ala
            325                 330                 335

Arg Asp Glu Phe Glu Asp Tyr Asn Ala Glu His Val His Arg Ile Thr
            340                 345                 350

Ala Pro Ile Ile Glu Ala Leu Ser His Pro Leu Asn Gly Asn Leu Thr
        355                 360                 365

Ser Pro Phe Pro Leu Thr Ser Leu Ser Ser Val Ile Leu Thr Gly Gly
    370                 375                 380

Ser Thr Arg Val Pro Met Val Lys Lys His Leu Glu Ser Leu Leu Gly
385                 390                 395                 400

Ser Glu Leu Ile Ala Lys Asn Val Asn Ala Asp Glu Ser Ala Val Phe
                405                 410                 415
```

```
Gly Ser Thr Leu Arg Gly Val Thr Leu Ser Gln Met Phe Lys Ala Lys
            420                 425                 430

Gln Met Thr Val Asn Glu Arg Ser Val Tyr Asp Tyr Cys Leu Lys Val
        435                 440                 445

Gly Ser Ser Glu Ile Asn Val Phe Pro Val Gly Thr Pro Leu Ala Thr
    450                 455                 460

Lys Lys Val Val Glu Leu Glu Asn Val Asp Ser Glu Asn Gln Leu Thr
465                 470                 475                 480

Ile Gly Leu Tyr Glu Asn Gly Gln Leu Phe Ala Ser His Glu Val Thr
                485                 490                 495

Asp Leu Lys Lys Ser Ile Lys Ser Leu Thr Gln Glu Gly Lys Glu Cys
            500                 505                 510

Ser Asn Ile Asn Tyr Glu Ala Thr Val Glu Leu Ser Glu Ser Arg Leu
        515                 520                 525

Leu Ser Leu Thr Arg Leu Gln Ala Lys Cys Ala Asp Glu Ala Glu Tyr
    530                 535                 540

Leu Pro Pro Val Asp Thr Glu Ser Glu Asp Thr Lys Ser Glu Asn Ser
545                 550                 555                 560

Thr Thr Ser Glu Thr Ile Glu Lys Pro Asn Lys Lys Leu Phe Tyr Pro
                565                 570                 575

Val Thr Ile Pro Thr Gln Leu Lys Ser Val His Val Lys Pro Met Gly
            580                 585                 590

Ser Ser Thr Lys Val Ser Ser Ser Leu Lys Ile Lys Glu Leu Asn Lys
        595                 600                 605

Lys Asp Ala Val Lys Arg Ser Ile Glu Glu Leu Lys Asn Gln Leu Glu
    610                 615                 620

Ser Lys Leu Tyr Arg Val Arg Ser Tyr Leu Glu Asp Glu Glu Val Val
625                 630                 635                 640

Glu Lys Gly Pro Ala Ser Gln Val Glu Ala Leu Ser Thr Leu Val Ala
                645                 650                 655

Glu Asn Leu Glu Trp Leu Asp Tyr Asp Ser Asp Ala Ser Ala Lys
            660                 665                 670

Asp Ile Arg Glu Lys Leu Asn Ser Val Ser Asp Ser Val Ala Phe Ile
        675                 680                 685

Lys Ser Tyr Ile Asp Leu Asn Asp Val Thr Phe Asp Asn Asn Leu Phe
    690                 695                 700

Thr Thr Ile Tyr Asn Thr Thr Leu Asn Ser Met Gln Asn Val Gln Glu
705                 710                 715                 720

Leu Met Leu Asn Met Ser Glu Asp Ala Leu Ser Leu Met Gln Gln Tyr
                725                 730                 735

Glu Lys Glu Gly Leu Asp Phe Ala Lys Glu Ser Gln Lys Ile Lys Ile
            740                 745                 750

Lys Ser Pro Pro Leu Ser Asp Lys Glu Leu Asp Asn Leu Phe Asn Thr
        755                 760                 765

Val Thr Glu Lys Leu Glu His Val Arg Met Leu Thr Glu Lys Asp Thr
    770                 775                 780

Ile Ser Asp Leu Pro Arg Glu Glu Leu Phe Lys Leu Tyr Gln Glu Leu
785                 790                 795                 800

Gln Asn Tyr Ser Ser Arg Phe Glu Ala Ile Met Ala Ser Leu Glu Asp
                805                 810                 815

Val His Ser Gln Arg Ile Asn Arg Leu Thr Asp Lys Leu Arg Lys His
            820                 825                 830

Ile Glu Arg Val Ser Asn Glu Ala Leu Lys Ala Ala Leu Lys Glu Ala
```

```
                835                 840                 845
Lys Arg Gln Gln Glu Glu Lys Ser His Glu Gln Asn Glu Gly Glu
    850                 855                 860
Glu Gln Ser Ser Ala Ser Thr Ser His Thr Asn Glu Asp Ile Glu Glu
865                 870                 875                 880
Pro Ser Glu Ser Pro Lys Val Gln Thr Ser His Asp Glu Leu
                885                 890

<210> SEQ ID NO 18
<211> LENGTH: 896
<212> TYPE: PRT
<213> ORGANISM: Pichia pastoris

<400> SEQUENCE: 18

Met Ser Ala Glu Glu Pro Thr Lys Glu Lys Ile Pro Ile Asn His Ser
1               5                   10                  15

Asp Asp Glu Asp Glu Asp Ile Asp Gln Leu Ile Glu Asp Leu Gln Ser
                20                  25                  30

Val His Gly Phe Asp Asp Glu Glu Glu Glu His His Glu Gly Ala
            35                  40                  45

Thr Ala Lys Pro Val Pro Glu Glu Leu Leu Gln Thr Asp Pro Ala Tyr
    50                  55                  60

Gly Leu Thr Thr Asp Glu Val His Lys Arg Arg Lys Arg Phe Gly Glu
65                  70                  75                  80

Asn Lys Met Ala Glu Glu Lys Glu Asn Leu Leu Val Lys Phe Cys Met
                85                  90                  95

Phe Phe Val Gly Pro Ile Gln Phe Val Met Glu Ala Ala Ile Leu
            100                 105                 110

Ala Ala Gly Leu Glu Asp Trp Val Asp Phe Gly Val Ile Leu Ala Leu
        115                 120                 125

Leu Phe Leu Asn Ala Ser Val Gly Phe Ile Gln Glu Tyr Gln Ala Gly
130                 135                 140

Ser Ile Val Asp Glu Leu Lys Lys Thr Leu Ala Asn Ser Ala Thr Val
145                 150                 155                 160

Ile Arg Asp Gly Gln Val Val Asp Ile Leu Ala Asp Glu Val Val Pro
                165                 170                 175

Gly Asp Ile Leu Lys Leu Glu Asp Gly Val Val Ile Pro Ala Asp Gly
            180                 185                 190

Arg Leu Val Ser Glu Glu Cys Phe Leu Gln Val Asp Gln Ser Ala Ile
        195                 200                 205

Thr Gly Glu Ser Leu Ala Val Asp Lys Lys Thr Gly Asp Ser Thr Tyr
    210                 215                 220

Ser Ser Ser Thr Val Lys Arg Gly Glu Ala Tyr Met Val Val Thr Ala
225                 230                 235                 240

Thr Gly Asp Ser Thr Phe Val Gly Arg Ala Ala Ala Leu Val Asn Lys
                245                 250                 255

Ala Ser Ala Gly Gln Gly His Phe Thr Glu Val Leu Asn Gly Ile Gly
            260                 265                 270

Thr Ile Leu Leu Val Leu Val Ile Ala Thr Leu Leu Val Val Trp Val
        275                 280                 285

Ala Cys Phe Tyr Arg Thr Ser Pro Ile Val Arg Ile Leu Arg Phe Thr
    290                 295                 300

Leu Ala Ile Thr Ile Val Gly Val Pro Val Gly Leu Pro Ala Val Val
305                 310                 315                 320
```

-continued

```
Thr Thr Thr Met Ala Val Gly Ala Ser Tyr Leu Ala Lys Lys Gln Ala
             325                 330                 335

Ile Val Gln Lys Leu Ser Ala Ile Glu Ser Leu Ala Gly Val Glu Ile
             340                 345                 350

Leu Cys Ser Asp Lys Thr Gly Thr Leu Thr Lys Asn Lys Leu Ser Leu
             355                 360                 365

His Glu Pro Tyr Thr Val Glu Val Glu Ala Asp Asp Leu Met Leu
             370                 375                 380

Thr Ala Cys Leu Ala Ala Ser Arg Lys Lys Lys Gly Leu Asp Ala Ile
385                  390                 395                 400

Asp Lys Ala Phe Leu Lys Ser Leu Ile Ser Tyr Pro Arg Ala Lys Ala
                 405                 410                 415

Ala Leu Thr Lys Tyr Lys Val Ile Glu Phe Gln Pro Phe Asp Pro Val
             420                 425                 430

Ser Lys Lys Val Thr Ala Tyr Val Glu Ser Pro Glu Gly Glu Arg Ile
             435                 440                 445

Ile Cys Val Lys Gly Ala Pro Leu Phe Val Leu Lys Thr Val Glu Glu
450                  455                 460

Asp His Pro Ile Pro Glu Asp Val His Asp Asn Tyr Glu Asn Lys Val
465                  470                 475                 480

Ala Glu Phe Ala Ser Arg Gly Phe Arg Ser Leu Gly Val Ala Arg Lys
                 485                 490                 495

Arg Gly Gln Gly His Trp Glu Ile Leu Gly Ile Met Pro Cys Met Asp
             500                 505                 510

Pro Pro Arg Asp Asp Thr Ala Gln Thr Val Asn Glu Ala Thr His Leu
             515                 520                 525

Gly Leu Arg Val Lys Met Leu Thr Gly Asp Ala Val Gly Ile Ala Lys
530                  535                 540

Glu Thr Cys Arg Gln Leu Gly Leu Gly Thr Asn Ile Tyr Asn Ala Glu
545                  550                 555                 560

Arg Leu Gly Leu Gly Gly Ala Gly Asp Met Pro Gly Ser Glu Ile Ala
                 565                 570                 575

Asp Phe Val Glu Asn Ala Asp Gly Phe Ala Glu Val Phe Pro Gln His
             580                 585                 590

Lys Tyr Asn Val Val Glu Ile Leu Gln Gln Arg Gly Tyr Leu Val Ala
             595                 600                 605

Met Thr Gly Asp Gly Val Asn Asp Ala Pro Ser Leu Lys Lys Ala Asp
             610                 615                 620

Thr Gly Ile Ala Val Glu Gly Ala Ser Asp Ala Ala Arg Ser Ala Ala
625                  630                 635                 640

Asp Ile Val Phe Leu Ala Pro Gly Leu Ser Ala Ile Ile Asp Ala Leu
                 645                 650                 655

Lys Thr Ser Arg Gln Ile Phe His Arg Met Tyr Ser Tyr Val Val Tyr
                 660                 665                 670

Arg Ile Ala Leu Ser Leu His Leu Glu Leu Phe Leu Gly Leu Trp Ile
             675                 680                 685

Ala Ile Met Asn Arg Ser Leu Asn Ile Asp Leu Val Val Phe Ile Ala
             690                 695                 700

Ile Phe Ala Asp Val Ala Thr Leu Ala Ile Ala Tyr Asp Asn Ala Pro
705                  710                 715                 720

Tyr Ser Pro Lys Pro Thr Lys Trp Asn Leu Pro Arg Leu Trp Gly Met
                 725                 730                 735

Ser Ile Ile Leu Gly Ile Ile Leu Ala Ile Gly Thr Trp Ile Thr Leu
```

```
            740                 745                 750
Thr Thr Met Leu Leu Pro Arg Gly Gly Ile Ile Gln Asn Phe Gly Ser
        755                 760                 765

Val Asp Gly Val Leu Phe Leu Glu Ile Ser Leu Thr Glu Asn Trp Leu
770                 775                 780

Ile Phe Ile Thr Arg Ala Ala Gly Pro Phe Trp Ser Ser Cys Pro Ser
785                 790                 795                 800

Trp Glu Leu Ala Gly Ala Val Ile Ile Val Asp Ile Ile Ala Thr Met
                    805                 810                 815

Phe Thr Leu Phe Gly Trp Trp Ser Gln Asn Trp Thr Asp Ile Val Thr
                820                 825                 830

Val Val Arg Val Trp Ile Phe Ser Phe Gly Val Phe Cys Val Met Gly
            835                 840                 845

Gly Ala Tyr Tyr Leu Met Ser Glu Ser Glu Gly Phe Asp Arg Leu Met
        850                 855                 860

Asn Gly Lys Pro Arg Lys Glu Pro Pro Gln Arg Ser Met Glu Asp
865                 870                 875                 880

Phe Ile Val Ala Met Gln Arg Val Ser Thr Gln His Glu Lys Ser Gly
                885                 890                 895
```

<210> SEQ ID NO 19
<211> LENGTH: 706
<212> TYPE: PRT
<213> ORGANISM: Pichia pastoris

<400> SEQUENCE: 19

```
Met Ser Val Pro Phe Gly Val Asp Leu Gly Asn Asn Asn Thr Val Ile
1               5                   10                  15

Gly Val Ala Arg Asn Arg Gly Ile Asp Ile Leu Val Asn Glu Val Ser
            20                  25                  30

Asn Arg Gln Thr Pro Ser Ile Val Gly Phe Gly Ala Lys Ser Arg Ala
        35                  40                  45

Ile Gly Glu Ser Gly Lys Thr Gln Gln Asn Ser Asn Leu Lys Asn Thr
    50                  55                  60

Val Glu His Leu Val Arg Ile Leu Gly Leu Pro Ala Asp Ser Pro Asp
65                  70                  75                  80

Tyr Glu Ile Glu Lys Lys Phe Phe Thr Ser Pro Leu Ile Glu Lys Asp
                85                  90                  95

Asn Glu Ile Leu Ser Glu Val Asn Phe Gln Gly Lys Lys Thr Thr Phe
            100                 105                 110

Thr Pro Ile Gln Leu Val Ala Met Tyr Leu Asn Lys Ile Lys Asn Thr
        115                 120                 125

Ala Ile Lys Glu Thr Lys Gly Lys Phe Thr Asp Ile Cys Leu Ala Val
    130                 135                 140

Pro Val Trp Phe Thr Glu Lys Gln Arg Ser Ala Ala Ser Asp Ala Cys
145                 150                 155                 160

Lys Val Ala Gly Leu Asn Pro Val Arg Ile Val Asn Asp Ile Thr Ala
                165                 170                 175

Ala Ala Val Gly Tyr Gly Val Phe Lys Thr Asp Leu Pro Glu Asp Glu
            180                 185                 190

Pro Lys Lys Val Ala Ile Val Asp Ile Gly His Ser Thr Tyr Ser Val
        195                 200                 205

Leu Ile Ala Ala Phe Lys Lys Gly Glu Leu Lys Val Leu Gly Ser Ala
    210                 215                 220
```

```
Ser Asp Lys His Phe Gly Gly Arg Asp Phe Asp Tyr Ala Ile Thr Lys
225                 230                 235                 240

His Phe Ala Glu Glu Phe Lys Ser Lys Tyr Lys Ile Asp Ile Thr Gln
            245                 250                 255

Asn Pro Lys Ala Trp Ser Arg Val Tyr Thr Ala Ala Glu Arg Leu Lys
        260                 265                 270

Lys Val Leu Ser Ala Asn Thr Thr Ala Pro Phe Asn Val Glu Ser Val
    275                 280                 285

Met Asn Asp Val Asp Val Ser Ser Leu Thr Arg Glu Glu Leu Glu
290                 295                 300

Lys Leu Val Gln Pro Leu Leu Asp Arg Ala His Ile Pro Val Glu Arg
305                 310                 315                 320

Ala Leu Ala Met Ala Gly Leu Lys Ala Glu Asp Val Asp Thr Val Glu
            325                 330                 335

Val Val Gly Gly Cys Thr Arg Val Pro Thr Leu Lys Ala Thr Leu Ser
            340                 345                 350

Glu Val Phe Gly Lys Pro Leu Ser Phe Thr Leu Asn Gln Asp Glu Ala
            355                 360                 365

Ile Ala Arg Gly Ala Ala Phe Ile Cys Ala Met His Ser Pro Thr Leu
370                 375                 380

Arg Val Arg Pro Phe Lys Phe Glu Asp Val Asn Pro Tyr Ser Val Ser
385                 390                 395                 400

Tyr Tyr Trp Asp Lys Asp Pro Ala Ala Glu Asp Asp His Leu Glu
            405                 410                 415

Val Phe Pro Val Gly Gly Ser Phe Pro Ser Thr Lys Val Ile Thr Leu
            420                 425                 430

Tyr Arg Ser Gln Asp Phe Asn Ile Glu Ala Arg Tyr Thr Asp Lys Asn
            435                 440                 445

Ala Leu Pro Ala Gly Thr Gln Glu Phe Ile Gly Arg Trp Ser Ile Lys
            450                 455                 460

Gly Val Val Val Asn Glu Gly Glu Asp Thr Ile Gln Thr Lys Ile Lys
465                 470                 475                 480

Leu Arg Asn Asp Pro Ser Gly Phe His Ile Val Glu Ser Ala Tyr Thr
                485                 490                 495

Val Glu Lys Lys Thr Ile Gln Glu Pro Ile Glu Asp Pro Glu Ala Asp
            500                 505                 510

Glu Asp Ala Glu Pro Gln Tyr Arg Thr Val Glu Lys Leu Val Lys Lys
        515                 520                 525

Asn Asp Leu Glu Ile Thr Gly Gln Thr Leu His Leu Pro Asp Glu Leu
530                 535                 540

Leu Asn Ser Tyr Leu Glu Thr Glu Ala Ala Leu Glu Val Gln Asp Lys
545                 550                 555                 560

Leu Val Ala Asp Thr Glu Glu Arg Lys Asn Ala Leu Glu Glu Tyr Ile
            565                 570                 575

Tyr Glu Leu Arg Gly Lys Leu Glu Asp Gln Tyr Lys Glu Phe Ala Ser
            580                 585                 590

Glu Gln Glu Lys Thr Lys Leu Thr Ala Lys Leu Glu Lys Ala Glu Glu
        595                 600                 605

Trp Leu Tyr Asp Glu Gly Tyr Asp Ser Thr Lys Ala Lys Tyr Ile Ala
            610                 615                 620

Lys Tyr Glu Glu Leu Ala Ser Ile Gly Asn Val Ile Arg Gly Arg Tyr
625                 630                 635                 640

Leu Ala Lys Glu Glu Glu Lys Lys Gln Ala Ile Arg Glu Lys Glu Glu
```

```
                    645                 650                 655
Ser Lys Lys Ala Ser Ala Ile Ala Glu Lys Met Ala Ala Glu Arg Ala
            660                 665                 670

Ser Arg Glu Ala Ala Gly Ser Thr Asn Glu Gln Ala Gln Lys Asn Glu
        675                 680                 685

Glu Asn Thr Lys Asp Ala Asp Gly Asp Val Ser Met Asn Gln Asp Glu
    690                 695                 700

Leu Asp
705

<210> SEQ ID NO 20
<211> LENGTH: 572
<212> TYPE: PRT
<213> ORGANISM: Pichia pastoris

<400> SEQUENCE: 20

Met Ser Ser Glu Glu Phe Lys Ala Gln Gly Asn Gln Ala Phe Gln Ala
1               5                   10                  15

Lys Asp Tyr Glu Lys Ala Val Ser Phe Phe Thr Gln Ala Ile Glu Ala
            20                  25                  30

Ser Pro Thr Pro Asn His Ile Leu Phe Ser Asn Arg Ser Ala Ala Tyr
        35                  40                  45

Ala Ser Leu Gly Gln Tyr Gln Asp Ala Leu Asp Ala Asn Lys Cys
    50                  55                  60

Val Glu Ile Asn Gly Ser Trp Ala Lys Gly Tyr Asn Arg Val Gly Ala
65                  70                  75                  80

Ala His Tyr Gly Arg Gly Glu Trp Asp Glu Ala His Lys Ala Tyr Ser
                85                  90                  95

Lys Ala Leu Glu Leu Asp Pro Ala Asn Lys Met Ala Lys Glu Gly Leu
            100                 105                 110

Asn Glu Thr Glu Ile Ala Arg Asp Ala Gly Asn Asp Val Lys Asn Ile
        115                 120                 125

Phe Ser Asp Ala Gly Met Val Glu Lys Leu Lys Lys Asn Pro Lys Thr
    130                 135                 140

Ala Glu Leu Met Lys Asp Pro Glu Leu Val Ala Lys Val Gln Lys Leu
145                 150                 155                 160

Gln Thr Asp Pro Lys Ser Met Ser Gln Glu Leu Phe Ser Asp Pro Arg
                165                 170                 175

Leu Met Thr Val Met Gly Ala Met Leu Gly Val Asp Leu Gly Val Gln
            180                 185                 190

Pro Ser Gln Gln Ser Ala Pro Gln Glu Asp Thr Pro Val Pro Asp Ala
        195                 200                 205

Tyr Pro Glu Pro Ser Ser Lys Pro Glu Thr Asn Thr Thr Ser Ala Lys
    210                 215                 220

Asn Ala Ala Pro Glu Pro Glu Lys Glu Ala Thr Pro Glu Pro Val
225                 230                 235                 240

Asp Asn Ser Lys Glu Glu Ala Asp Asn Leu Lys Gln Gln Ala Asn Gln
                245                 250                 255

Leu Tyr Lys Lys Arg Gln Phe Asp Glu Ala Ile Glu Leu Tyr Asn Lys
            260                 265                 270

Ala Trp Glu Thr Phe Gln Asp Ile Thr Tyr Leu Asn Asn Arg Ala Ala
        275                 280                 285

Ala Glu Phe Glu Lys Gly Asp Tyr Asp Ala Thr Ile Glu Thr Cys Glu
    290                 295                 300
```

```
Asn Ala Val Glu Lys Gly Arg Glu Leu Arg Ala Asp Tyr Lys Leu Val
305                 310                 315                 320

Ala Lys Ser Phe Ala Arg Leu Gly Ser Ala Tyr Leu Lys Lys Asp Asp
            325                 330                 335

Leu Pro Asn Ala Ile Lys Phe Phe Glu Lys Ser Leu Thr Glu His Arg
            340                 345                 350

Ser Pro Asp Val Leu Ser Lys Leu Arg Ala Ala Glu Ala Asp Leu Lys
        355                 360                 365

Lys Lys Glu Ala Glu Glu Tyr Ile Asp Pro Lys Ala Glu Glu Ala
    370                 375                 380

Arg Leu Gln Gly Lys Asp Phe Phe Thr Lys Gly Asp Trp Pro Ala Ala
385                 390                 395                 400

Val Lys Ala Tyr Thr Glu Met Ile Asn Arg Ala Pro Lys Asp Ala Arg
            405                 410                 415

Gly Tyr Ser Asn Arg Ala Ala Ala Leu Ala Lys Leu Met Ser Phe Pro
            420                 425                 430

Asp Ala Val Lys Asp Cys Asp Lys Ala Ile Glu Leu Asp Pro Ser Phe
        435                 440                 445

Val Arg Ala Tyr Ile Arg Lys Ala Thr Ala Leu Ile Ala Met Lys Asp
    450                 455                 460

Phe Asn Lys Ala Met Thr Thr Leu Glu Glu Ala Arg Thr Val Asp Ala
465                 470                 475                 480

Asp Thr Asn Glu Gly Lys Ala Ala Asn Glu Ile Asn Gly Leu Tyr Tyr
            485                 490                 495

Lys Ala Ser Ser Gln Arg Phe Ala Ala Ile Asp Gly Glu Thr Pro Glu
        500                 505                 510

Gln Thr Phe Glu Arg Ala Ser Lys Asp Pro Glu Val Ser Ala Ile Leu
    515                 520                 525

Gln Asp Pro Val Met Asn Ser Ile Leu Gln Gln Ala Arg Glu Asn Pro
530                 535                 540

Ala Ala Leu Gln Glu His Met Lys Asn Pro Glu Val Ala Lys Lys Ile
545                 550                 555                 560

Asn Ile Leu Ile Ala Ala Gly Val Ile Arg Thr Arg
            565                 570

<210> SEQ ID NO 21
<211> LENGTH: 845
<212> TYPE: PRT
<213> ORGANISM: Pichia pastoris

<400> SEQUENCE: 21

Met Thr Thr Pro Ile Ala Gln Ile Gln Leu Glu Gln Glu Ala Ser Lys
1               5                   10                  15

Asn Pro Pro Lys Gln His Thr Arg Leu Ser Asp Leu Val Glu Lys Thr
            20                  25                  30

Lys Gly Thr Lys Ser Trp Val Ser Pro Phe Arg Thr Asp Ala Lys Ala
        35                  40                  45

Ala Ser Pro Lys Arg Glu Ser Tyr Pro Pro Gln Ile Val Ala Asp Val
    50                  55                  60

Lys Pro Glu Asp Val Asp Asn Ala Glu Glu Thr Ile Leu Asp His
65                  70                  75                  80

Asp Asp Ala Asn Ala Thr Val Asp Pro Ile Glu Ser Glu Ser Val Leu
            85                  90                  95

Asp Ala Ser Asp Ile Ser Ile Lys Gly Ser Thr Ala Glu Asp Asn Gln
        100                 105                 110
```

```
Glu Glu Gln Pro Glu Pro Ala Thr Asp Val Leu Pro Gln Asp Ala Glu
        115                 120                 125
Glu Glu Val Ala Asp Lys Asp Thr Gln Ser Gly Asp Ile Pro Gln Asp
130                 135                 140
Glu Gly Ser Gln Ala Glu Gln Glu Glu Gln Ala Pro Glu Ala Gln
145                 150                 155                 160
Glu Glu Gln Val Ser Glu Ser Gln Glu Ala Lys Glu Asp Asp Lys Val
                165                 170                 175
Asp Asn Val Glu Ala Lys Lys Asp Val Ala Asp Lys Lys Val Thr Lys
                180                 185                 190
Gln Thr Gln Gln Ala Ile Lys Asp Thr Glu Gly Ala Lys Ala Val
        195                 200                 205
Lys Glu Ala Gln Ala Lys Leu Lys Glu Ala Glu Leu Lys Leu Leu Lys
210                 215                 220
Glu Pro Val Val Ile Thr Pro Asp Leu Leu Gln Pro Pro Ala Glu Asp
225                 230                 235                 240
Asp Ala Glu Lys Thr Leu Lys Asp Lys Pro Leu Leu Asn Arg Tyr
                245                 250                 255
Lys Gln Asn Lys Glu Ile Ala Glu Ser Ser Leu Gln Lys Lys Asp Val
                260                 265                 270
Glu Asn Pro Asp Gln Val Val Asp Leu Gly Gly Gly Leu Leu Leu Thr
                275                 280                 285
Gln Ala Gln Ile Tyr Ser Ile Ala Gln Ala Arg Val Lys Pro Leu Leu
        290                 295                 300
Gly Lys Ile Asp Lys Gln Val Asp Leu Asn Lys Ala Asp Glu Leu
305                 310                 315                 320
Lys Lys Arg Gln Thr Glu Gln Gln Tyr His Glu Gln Lys Asp Leu Gln
                325                 330                 335
Gln Ser Lys Asn Leu Glu Lys Tyr Gln Thr Gln Leu Thr Arg Glu Asn
                340                 345                 350
Asn Ile Ile Val Ala Arg Phe Asp Thr Asp Ile Ala Ala Leu Ser Ser
        355                 360                 365
Thr Ile Leu Ser Asn Ala Thr Leu Leu Glu Glu Phe Ala Thr Gln Thr
370                 375                 380
Arg Lys Glu Ile Asp Asp Leu Gly Thr Lys Ala Leu Ala Glu Glu Glu
385                 390                 395                 400
Lys Leu Ala Glu Glu His Glu Thr Asn Lys Thr Lys Leu Glu Glu Asn
                405                 410                 415
Ala Lys Gln Tyr Lys Glu Asp Leu Glu Thr Lys Leu Leu Asn Ala Thr
                420                 425                 430
Thr Gly Gln Glu Asp Glu Lys Thr Lys Ile Glu Glu Leu Lys Val Lys
        435                 440                 445
Val Glu Glu Glu Lys Ala Ile Ala Asp Asp Leu Glu Glu Lys Ala Phe
450                 455                 460
Asp Lys Asn Glu Ala Leu Asn Ala Lys Arg Ala Glu Leu Glu Glu Leu
465                 470                 475                 480
Val Ala Glu Glu Ala Lys Leu Gln Ala Thr Val Asp Glu Ser Glu Gln
                485                 490                 495
Phe Gln Lys Glu Cys Asp Ala Lys Ala Ala Leu Ser Val Asp His
                500                 505                 510
Thr Lys Ser Thr Lys Lys Leu Glu Lys Leu Gln Ser His Val Ser Ala
        515                 520                 525
```

```
Leu Gly Ser Ala Ile Glu Lys His Ala Ser Lys Ile Gly Phe Leu Thr
            530                 535                 540

Gly Ala Ala Val Ala Ser Arg Glu Val Lys Arg Lys His Asn Glu Ser
545                 550                 555                 560

Leu Lys Ser Glu Trp Leu Ala Glu Lys Ala Arg Ile Arg Ser Glu Val
                565                 570                 575

Ala Lys Ala Asn Glu Arg Lys Thr Leu Glu Ala Glu Leu Glu Arg Glu
            580                 585                 590

Arg Leu Ala Lys Glu Lys Glu Ile Glu Arg Gln Gln Lys Glu Glu Gln
                595                 600                 605

Tyr Ala Gln Glu Lys Leu Asp Arg Ala Glu Glu Lys Arg Leu Lys
            610                 615                 620

Glu Asp Val Ala Glu Leu Gln Arg Val Lys Gln Leu Lys Lys Glu Lys
625                 630                 635                 640

Ser Lys Leu Ser Lys Lys Leu Ala Ser Thr Gly Ser Phe Phe Ala Gly
                645                 650                 655

Gly Val Ala Thr Gly Ala Ala Ile Gly Ala Ala Thr Gly Ala Ala Ala
            660                 665                 670

Gly Ser Ala Ala Gly Ala Ala Ser Gly Ala Gly Ala Ala Ser
                675                 680                 685

Gly Ala Ser Lys Val Val Ser Ser Thr Asn Thr Ala Ser Lys Gly
            690                 695                 700

Ala Ser Asp Ala Ala Gln Val Gly Asn Gly Ala Lys Lys Thr Ala Asp
705                 710                 715                 720

Ile Lys Arg Asn Glu Ser Phe Ala Ser Asn Ser Pro Glu Ile Lys Ile
                725                 730                 735

Asp Asp Glu Thr Leu Asn Lys Asp Ala Lys Pro Leu Phe Thr Glu Val
            740                 745                 750

Val Glu Asp Val Pro Thr Thr Thr Ser Lys Ala Asp Glu Asp Ile Lys
                755                 760                 765

Lys Lys Asn Arg Leu Ser Phe Leu Gly Ser Ile Lys Arg Lys Ala Ser
                770                 775                 780

Leu Gly Ser Lys Lys Glu Pro Glu Lys Lys Glu Pro Ala Thr Gly Val
785                 790                 795                 800

Val Pro Ala Ser Ser Ser Ile Ala Lys Asp Asn Asp Gly Glu Tyr
                805                 810                 815

Glu Glu Val Ser Thr Leu Glu Thr Ile Ser Asp Ala Glu Tyr Glu Ala
                820                 825                 830

His Lys Asp Asp Pro Asn Tyr Phe Ile Val Asp Pro Lys
                835                 840                 845

<210> SEQ ID NO 22
<211> LENGTH: 402
<212> TYPE: PRT
<213> ORGANISM: Pichia pastoris

<400> SEQUENCE: 22

Met Val Arg Glu Thr Lys Leu Tyr Asp Ile Leu Gly Val Ser Pro Asp
1               5                   10                  15

Ala Thr Asp Ala Gln Leu Lys Lys Ala Tyr Arg Val Gly Ala Leu Lys
            20                  25                  30

Asn His Pro Asp Lys Asn Pro Ser Pro Glu Ala Ala Glu Thr Phe Lys
        35                  40                  45

Gly Met Ser His Ala Tyr Glu Val Leu Ser Asp Pro Gln Lys Arg Glu
    50                  55                  60
```

-continued

```
Ile Tyr Asp Gln Tyr Gly Glu Glu Gly Leu Asn Gly Gly Ala Gly
 65                  70                  75                  80

Pro Gly Gly Met Gly Glu Asp Ile Phe Ser Gln Phe Phe Gly Met
                 85                  90                  95

Phe Pro Gly Gly Gly Gln Pro Thr Gly Pro Gln Arg Gly Lys Asp Ile
                100                 105                 110

Lys His Ser Ile Ser Cys Thr Leu Glu Glu Leu Tyr Lys Gly Arg Thr
                115                 120                 125

Ala Lys Leu Ala Leu Asn Lys Thr Val Leu Cys Lys Glu Cys Asp Gly
130                 135                 140

Lys Gly Gly Lys Asn Val Lys Lys Cys Ser Ala Cys Asn Gly Gln Gly
145                 150                 155                 160

Leu Arg Phe Val Thr Arg Gln Ile Gly Pro Met Ile Gln Arg Ala Gln
                165                 170                 175

Val Arg Cys Asp Val Cys Asn Gly Glu Gly Asp Ile Ile Ser Gly Ala
                180                 185                 190

Asp Arg Cys Lys Ala Cys Ser Gly Lys Lys Ile Thr Asn Glu Arg Lys
                195                 200                 205

Ile Leu Glu Val Asn Ile Glu Arg Gly Met Arg His Gly Gln Lys Val
210                 215                 220

Val Phe Ser Gly Glu Ser Asp Gln Ala Pro Asp Val Ile Pro Gly Asp
225                 230                 235                 240

Val Ile Phe Val Val Asp Glu Lys Pro His Lys Asp Phe Ser Arg Lys
                245                 250                 255

Gly Asp Asp Leu Tyr Tyr Glu Ala Lys Ile Asp Leu Leu Thr Ala Leu
                260                 265                 270

Ala Gly Gly Glu Leu Ala Ile Lys His Ile Ser Gly Glu Tyr Leu Lys
                275                 280                 285

Ile Thr Ile Ile Pro Gly Glu Val Ile Ser Pro Gly Ser Val Lys Val
290                 295                 300

Ile Val Gly Lys Gly Met Pro Val Arg Lys Ser Ser Ser Tyr Gly Asn
305                 310                 315                 320

Leu Tyr Val Lys Phe Glu Ile Asp Phe Pro Lys Asn Phe Thr Thr
                325                 330                 335

Ala Glu Asn Leu Gln Leu Leu Glu Gln Val Leu Pro Ala Arg Thr Pro
                340                 345                 350

Val Ser Ile Pro Ala Asp Ala Glu Val Asp Glu Val Val Leu Ala Asp
                355                 360                 365

Val Asp Pro Thr Gln Gln Arg Gln Gly Gly Arg Gly Gly Gln Ser
                370                 375                 380

Tyr Asp Ser Asp Asp Glu Glu Gln Gly Gly Gln Gly Val Gln Cys Ala
385                 390                 395                 400

Ser Gln
```

<210> SEQ ID NO 23
<211> LENGTH: 21
<212> TYPE: DNA
<213> ORGANISM: Artificial Sequence
<220> FEATURE:
<223> OTHER INFORMATION: FW-AOX promoter primer

<400> SEQUENCE: 23
gactggttcc aattgacaag c                                        21

```
<210> SEQ ID NO 24
<211> LENGTH: 35
<212> TYPE: DNA
<213> ORGANISM: Artificial Sequence
<220> FEATURE:
<223> OTHER INFORMATION: RV-FkpA primer

<400> SEQUENCE: 24
gtcgtgggcg cgccttttttt tggcgctatc tgcgg                       35

<210> SEQ ID NO 25
<211> LENGTH: 35
<212> TYPE: DNA
<213> ORGANISM: Artificial Sequence
<220> FEATURE:
<223> OTHER INFORMATION: RV-SKP primer

<400> SEQUENCE: 25
gtcgtgggcg cgcctttga cttgcttcag cacgt                         35

<210> SEQ ID NO 26
<211> LENGTH: 38
<212> TYPE: DNA
<213> ORGANISM: Artificial Sequence
<220> FEATURE:
<223> OTHER INFORMATION: RV-Ero primer

<400> SEQUENCE: 26
agctggcggc cgcttacaag tctactctat atgtggta                     38

<210> SEQ ID NO 27
<211> LENGTH: 38
<212> TYPE: DNA
<213> ORGANISM: Artificial Sequence
<220> FEATURE:
<223> OTHER INFORMATION: RV-Kar2p primer

<400> SEQUENCE: 27
agctggcggc cgcctacaac tcatcatgat catagtca                     38

<210> SEQ ID NO 28
<211> LENGTH: 38
<212> TYPE: DNA
<213> ORGANISM: Artificial Sequence
<220> FEATURE:
<223> OTHER INFORMATION: RV-PDI1 primer

<400> SEQUENCE: 28
agctggcggc cgcttaaagc tcgtcgtgag cgtctgcc                     38

<210> SEQ ID NO 29
<211> LENGTH: 38
<212> TYPE: DNA
<213> ORGANISM: Artificial Sequence
<220> FEATURE:
<223> OTHER INFORMATION: RV-RPP0 primer

<400> SEQUENCE: 29
agctggcggc cgcttaatca aacaaaccga atcccatg                     38

<210> SEQ ID NO 30
<211> LENGTH: 38
<212> TYPE: DNA
<213> ORGANISM: Artificial Sequence
<220> FEATURE:
<223> OTHER INFORMATION: RV-BFR2 primer
```

```
<400> SEQUENCE: 30
agctggcggc cgcttatcca aacagtttga tatcatcc                                38

<210> SEQ ID NO 31
<211> LENGTH: 38
<212> TYPE: DNA
<213> ORGANISM: Artificial Sequence
<220> FEATURE:
<223> OTHER INFORMATION: RV-BMH2 primer

<400> SEQUENCE: 31
agctggcggc cgctcactct tcatctttgg gagcagct                                38

<210> SEQ ID NO 32
<211> LENGTH: 38
<212> TYPE: DNA
<213> ORGANISM: Artificial Sequence
<220> FEATURE:
<223> OTHER INFORMATION: RV-Cct2 primer

<400> SEQUENCE: 32
agctggcggc cgctcaacga ttacggtcgg cagtgcgt                                38

<210> SEQ ID NO 33
<211> LENGTH: 38
<212> TYPE: DNA
<213> ORGANISM: Artificial Sequence
<220> FEATURE:
<223> OTHER INFORMATION: RV-Erj5 primer

<400> SEQUENCE: 33
agctggcggc cgcttatttc cttctacgtc caccggat                                38

<210> SEQ ID NO 34
<211> LENGTH: 38
<212> TYPE: DNA
<213> ORGANISM: Artificial Sequence
<220> FEATURE:
<223> OTHER INFORMATION: RV-Gim4 primer

<400> SEQUENCE: 34
agctggcggc cgcctactca ttagcactca caatcttg                                38

<210> SEQ ID NO 35
<211> LENGTH: 38
<212> TYPE: DNA
<213> ORGANISM: Artificial Sequence
<220> FEATURE:
<223> OTHER INFORMATION: RV-KIN2 primer

<400> SEQUENCE: 35
agctggcggc cgcctataaa ttcaattctt gtagcagc                                38

<210> SEQ ID NO 36
<211> LENGTH: 38
<212> TYPE: DNA
<213> ORGANISM: Artificial Sequence
<220> FEATURE:
<223> OTHER INFORMATION: RV-Mdj1 primer

<400> SEQUENCE: 36
agctggcggc cgcctattta cagtcgtcct tcttattg                                38

<210> SEQ ID NO 37
<211> LENGTH: 45
```

<210> SEQ ID NO 37
<211> LENGTH: (not shown)
<212> TYPE: DNA
<213> ORGANISM: Artificial Sequence
<220> FEATURE:
<223> OTHER INFORMATION: RV-HAC1spliced primer

<400> SEQUENCE: 37
atgcattagc ggtaaatggt gctgctggat gatgcaaccg attcg            45

<210> SEQ ID NO 38
<211> LENGTH: 35
<212> TYPE: DNA
<213> ORGANISM: Artificial Sequence
<220> FEATURE:
<223> OTHER INFORMATION: RV-Def1 primer

<400> SEQUENCE: 38
agctggcggc cgcttaaatc caccctttag cattg                       35

<210> SEQ ID NO 39
<211> LENGTH: 35
<212> TYPE: DNA
<213> ORGANISM: Artificial Sequence
<220> FEATURE:
<223> OTHER INFORMATION: RV-Gas1 primer

<400> SEQUENCE: 39
agctggcggc cgcttagaat gacataatca ttcca                       35

<210> SEQ ID NO 40
<211> LENGTH: 34
<212> TYPE: DNA
<213> ORGANISM: Artificial Sequence
<220> FEATURE:
<223> OTHER INFORMATION: RV-LHS1 primer

<400> SEQUENCE: 40
agctggcggc cgcctacaac tcatcatggg atgt                        34

<210> SEQ ID NO 41
<211> LENGTH: 35
<212> TYPE: DNA
<213> ORGANISM: Artificial Sequence
<220> FEATURE:
<223> OTHER INFORMATION: RV-Pma1 primer

<400> SEQUENCE: 41
agctggcggc cgcttaacca gacttctcgt gctga                       35

<210> SEQ ID NO 42
<211> LENGTH: 35
<212> TYPE: DNA
<213> ORGANISM: Artificial Sequence
<220> FEATURE:
<223> OTHER INFORMATION: RV-SSE1 primer

<400> SEQUENCE: 42
agctggcggc cgcttaatct agctcatctt ggttc                       35

<210> SEQ ID NO 43
<211> LENGTH: 34
<212> TYPE: DNA
<213> ORGANISM: Artificial Sequence
<220> FEATURE:
<223> OTHER INFORMATION: RV-Sti1 primer

<400> SEQUENCE: 43

```
agctggcggc cgcttaacga gtacgaatga cacc                                    34
```

<210> SEQ ID NO 44
<211> LENGTH: 35
<212> TYPE: DNA
<213> ORGANISM: Artificial Sequence
<220> FEATURE:
<223> OTHER INFORMATION: RV-Uso1 primer

<400> SEQUENCE: 44

```
agctggcggc cgcttatttg ggatcgacga tgaaa                                   35
```

<210> SEQ ID NO 45
<211> LENGTH: 36
<212> TYPE: DNA
<213> ORGANISM: Artificial Sequence
<220> FEATURE:
<223> OTHER INFORMATION: RV-Ydj1 primer

<400> SEQUENCE: 45

```
agctggcggc cgcttactga gaagcacatt ggacac                                  36
```

<210> SEQ ID NO 46
<211> LENGTH: 98
<212> TYPE: PRT
<213> ORGANISM: Artificial Sequence
<220> FEATURE:
<223> OTHER INFORMATION: Nanobody Sequence

<400> SEQUENCE: 46

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala

<210> SEQ ID NO 47
<211> LENGTH: 97
<212> TYPE: PRT
<213> ORGANISM: Artificial Sequence
<220> FEATURE:
<223> OTHER INFORMATION: Nanobody Sequence

<400> SEQUENCE: 47

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu

```
65                  70                  75                  80
Gln Met Asn Ser Leu Lys Pro Glu Asp Thr Ala Val Tyr Tyr Cys Asn
                85                  90                  95

Ala

<210> SEQ ID NO 48
<211> LENGTH: 98
<212> TYPE: PRT
<213> ORGANISM: Artificial Sequence
<220> FEATURE:
<223> OTHER INFORMATION: Nanobody Sequence

<400> SEQUENCE: 48

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
            35                  40                  45

Ala Ala Ile Ser Trp Ser Gly Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala

<210> SEQ ID NO 49
<211> LENGTH: 249
<212> TYPE: PRT
<213> ORGANISM: Artificial Sequence
<220> FEATURE:
<223> OTHER INFORMATION: Nanobody Sequence

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
                20                  25                  30

Ala Ile Gly Trp Phe Arg Gln Ala Pro Gly Lys Glu Arg Glu Gly Val
            35                  40                  45

Leu Cys Ile Asp Ala Ser Asp Asp Ile Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175
```

```
Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser
                245

<210> SEQ ID NO 50
<211> LENGTH: 284
<212> TYPE: PRT
<213> ORGANISM: Artificial Sequence
<220> FEATURE:
<223> OTHER INFORMATION: Nanobody Sequence

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Leu Asn Tyr Phe
            20                  25                  30

Glu Ile Val Trp Phe Arg Gln Ala Pro Gly Lys Glu Arg Glu Gly Ile
            35                  40                  45

Ile Cys Ile Ser Asn Ser Asp Asp Lys Thr Tyr Tyr Val Asp Ser Val
50                  55                  60

Lys Gly Arg Phe Thr Phe Ser Arg Asp Val Ala Lys Asn Thr Val Tyr
65                  70                  75                  80

Leu Gln Met Asn Ser Leu Lys Arg Glu Asp Thr Ala Asp Tyr Tyr Cys
                85                  90                  95

Ala Thr Asn Leu Tyr Gly Thr Cys His Thr Thr Leu Lys Ala Asp Asp
            100                 105                 110

Met Ala Tyr Trp Gly Lys Gly Thr Leu Val Thr Val Ser Ser Gly Gly
            115                 120                 125

Gly Gly Ser Gly Gly Gly Ser Glu Val Gln Leu Val Glu Ser Gly Gly
        130                 135                 140

Gly Leu Val Gln Pro Gly Asn Ser Leu Arg Leu Ser Cys Ala Ala Ser
145                 150                 155                 160

Gly Phe Thr Phe Ser Ser Phe Gly Met Ser Trp Val Arg Gln Ala Pro
            165                 170                 175

Gly Lys Gly Leu Glu Trp Val Ser Ser Ile Ser Gly Ser Gly Ser Asp
            180                 185                 190

Thr Leu Tyr Ala Asp Ser Val Lys Gly Arg Phe Thr Ile Ser Arg Asp
            195                 200                 205

Asn Ala Lys Thr Thr Leu Tyr Leu Gln Met Asn Ser Leu Arg Pro Glu
        210                 215                 220

Asp Thr Ala Val Tyr Tyr Cys Thr Ile Gly Gly Ser Leu Ser Arg Ser
225                 230                 235                 240

Ser Gln Gly Thr Leu Val Thr Val Ser Ser Gly Ala Ala Asp Tyr Lys
                245                 250                 255

Asp His Asp Gly Asp Tyr Lys Asp His Asp Ile Asp Tyr Lys Asp Asp
            260                 265                 270

Asp Asp Lys Gly Ala Ala His His His His His His
            275                 280
```

<210> SEQ ID NO 51
<211> LENGTH: 390
<212> TYPE: PRT
<213> ORGANISM: Artificial Sequence
<220> FEATURE:
<223> OTHER INFORMATION: Nanobody Sequence

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Asp Asp Tyr
            20                  25                  30

Ala Ile Ala Trp Phe Arg Gln Ala Pro Gly Lys Gly Arg Glu Gly Val
        35                  40                  45

Ser Gly Ile Asp Ser Gly Asp Gly Ser Ala Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Arg Val Arg Thr Gly Trp Gly Leu Asn Ala Pro Asp Tyr Ala Met
            100                 105                 110

Asp Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Glu Val Gln Leu
    130                 135                 140

Val Glu Ser Gly Gly Gly Leu Val Gln Pro Gly Asn Ser Leu Arg Leu
145                 150                 155                 160

Ser Cys Ala Ala Ser Gly Phe Thr Phe Ser Ser Phe Gly Met Ser Trp
                165                 170                 175

Val Arg Gln Ala Pro Gly Lys Gly Leu Glu Trp Val Ser Ser Ile Ser
            180                 185                 190

Gly Ser Gly Ser Asp Thr Leu Tyr Ala Asp Ser Val Lys Gly Arg Phe
        195                 200                 205

Thr Ile Ser Arg Asp Asn Ala Lys Thr Thr Leu Tyr Leu Gln Met Asn
    210                 215                 220

Ser Leu Arg Pro Glu Asp Thr Ala Val Tyr Tyr Cys Thr Ile Gly Gly
225                 230                 235                 240

Ser Leu Ser Arg Ser Ser Gln Gly Thr Leu Val Thr Val Ser Ser Gly
                245                 250                 255

Gly Gly Gly Ser Gly Gly Gly Ser Glu Val Gln Leu Leu Glu Ser Gly
            260                 265                 270

Gly Gly Leu Val Gln Pro Gly Gly Ser Leu Arg Leu Ser Cys Ala Ala
        275                 280                 285

Ser Gly Phe Thr Leu Asp Tyr Leu Ala Ile Gly Trp Phe Arg Gln Ala
    290                 295                 300

Pro Gly Lys Gly Arg Glu Gly Val Ser Cys Val Ser Ser Ser Gly Gln
305                 310                 315                 320

Tyr Thr Tyr Tyr Ala Asp Ser Val Lys Gly Arg Phe Thr Ile Ser Arg
                325                 330                 335

Asp Asn Ser Glu Ser Thr Val Tyr Leu Gln Met Asn Ser Leu Arg Pro
            340                 345                 350

Glu Asp Thr Ala Val Tyr Tyr Cys Ala Thr Asp Pro Glu Cys Tyr Arg
        355                 360                 365

-continued

```
Val Arg Gly Tyr Tyr Asn Ala Glu Tyr Asp Tyr Trp Gly Gln Gly Thr
        370                 375                 380

Leu Val Thr Val Ser Ser
385                 390

<210> SEQ ID NO 52
<211> LENGTH: 467
<212> TYPE: PRT
<213> ORGANISM: Artificial Sequence
<220> FEATURE:
<223> OTHER INFORMATION: Nanobody Sequence

<400> SEQUENCE: 52

Glu Val Gln Leu Val Glu Ser Gly Gly Gly Leu Val Gly Thr Gly Gly
1               5                   10                  15

Ser Leu Arg Leu Ser Cys Ala Ala Ser Gly Asn Ile Ala Asp Leu Gly
            20                  25                  30

Val Met Gly Trp Tyr Arg Gln Ala Pro Ala Lys Lys Gly Glu Leu Val
        35                  40                  45

Ala Thr Met Pro Arg Thr Gly Ser Lys Trp Tyr Gln Asp Ser Val Lys
    50                  55                  60

Gly Arg Phe Thr Ile His Arg Asp Asn Ser Lys Ser Thr Val Asp Leu
65                  70                  75                  80

Glu Met Gly Ser Leu Lys Pro Glu Asp Thr Ala Val Tyr Tyr Cys Val
                85                  90                  95

Ala Ser Arg Met Phe Gln Thr Ile Leu Lys Pro Asn Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gly Gly Gly Ser Gly Gly Gly Gly
    130                 135                 140

Ser Gly Gly Gly Ser Gly Gly Gly Ser Glu Val Gln Leu Val
145                 150                 155                 160

Glu Ser Gly Gly Gly Leu Val Gln Pro Gly Glu Ser Leu Arg Leu Ser
                165                 170                 175

Cys Val Ala Ser Gly Phe Thr Phe Ser Ser Thr Asp Met Ser Trp Leu
            180                 185                 190

Arg Gln Ala Thr Gly Lys Gly Pro Glu Trp Leu Ser Ser Ile Asn Ser
        195                 200                 205

Gly Gly Ser Ser Thr Arg Tyr Ala Glu Ser Val Lys Gly Arg Phe Thr
    210                 215                 220

Val Ser Arg Asp Asn Thr Lys Asn Thr Leu Tyr Leu Gln Met Asp Ser
225                 230                 235                 240

Leu Gln Pro Glu Asp Thr Ala Lys Tyr Tyr Cys Ala Arg Gly Trp Thr
                245                 250                 255

Pro Thr Gly Arg Ala Gly Pro Gly Thr Leu Val Thr Val Ser Ser Gly
            260                 265                 270

Gly Gly Ser Gly Gly Gly Gly Ser Gly Gly Gly Ser Gly Gly
        275                 280                 285

Gly Gly Ser Gly Gly Gly Ser Gly Gly Gly Ser Gly Gly Gly
    290                 295                 300

Gly Ser Glu Val Gln Leu Val Glu Ser Gly Gly Leu Val Gln Ala
305                 310                 315                 320

Gly Gly Ser Leu Arg Leu Ser Cys Ala Ala Ser Gly Phe Thr Leu Asp
                325                 330                 335
```

```
Asp Tyr Asp Met Ser Trp Phe Arg Gln Ala Pro Gly Lys Glu Arg Glu
                340                 345                 350

Met Ile Ser Cys Ile Ser Ser Asp Gly Arg Pro Tyr Tyr Glu Asp
        355                 360                 365

Ser Val Lys Gly Arg Phe Thr Val Thr Ser Asp Asn Ala Lys Asn Thr
    370                 375                 380

Val Tyr Leu Gln Met Asn Ser Leu Lys Pro Glu Asp Thr Ala Val Tyr
385                 390                 395                 400

Tyr Cys Ala Ala Gly Ala Lys Ile Phe Ala Val Pro Gly Ser Leu Cys
                405                 410                 415

Ser Val Arg Asn Ala His Trp Gly Gln Gly Thr Leu Val Thr Val Ser
                420                 425                 430

Ser Gly Ala Ala Asp Tyr Lys Asp His Asp Gly Asp Tyr Lys Asp His
                435                 440                 445

Asp Ile Asp Tyr Lys Asp Asp Asp Lys Gly Ala Ala His His His
                450                 455                 460

His His His
465

<210> SEQ ID NO 53
<211> LENGTH: 575
<212> TYPE: PRT
<213> ORGANISM: Artificial Sequence
<220> FEATURE:
<223> OTHER INFORMATION: Nanobody Sequence

<400> SEQUENCE: 53

Asp Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Thr Asn
            20                  25                  30

Pro Met Tyr Trp Tyr Arg Gln Ala Pro Gly Lys Gln Arg Glu Leu Val
        35                  40                  45

Ala Ser Ile Ser Ser Arg Gly Ile Thr Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Arg
                85                  90                  95

Leu Ala Ser Leu Ser Ser Gly Thr Val Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Ser Thr Arg Ser Val Asn Pro Met Ala Trp Phe Arg Gln Ala
            180                 185                 190

Pro Gly Lys Gln Arg Glu Trp Val Ala Thr Ile Ser Arg Ser Gly Tyr
        195                 200                 205

Ala Thr Tyr Ala Asp Ser Val Lys Gly Arg Phe Thr Ile Ser Arg Asp
    210                 215                 220
```

-continued

Asn Ser Lys Asn Thr Val Tyr Leu Gln Met Asn Ser Leu Arg Pro Glu
225                 230                 235                 240

Asp Thr Ala Val Tyr Tyr Cys Val Thr Gly Thr Tyr Trp Gly Gln Gly
            245                 250                 255

Thr Leu Val Thr Val Ser Ser Gly Gly Gly Ser Gly Gly Gly Gly
        260                 265                 270

Ser Gly Gly Gly Gly Ser Gly Gly Gly Ser Gly Gly Gly Ser
        275                 280                 285

Gly Gly Gly Gly Ser Gly Gly Gly Ser Glu Val Gln Leu Val Glu
    290                 295                 300

Ser Gly Gly Gly Leu Val Gln Pro Gly Gly Ser Leu Arg Leu Ser Cys
305                 310                 315                 320

Ala Ala Ser Gly Phe Thr Phe Arg Ser Phe Gly Met Ser Trp Val Arg
            325                 330                 335

Gln Ala Pro Gly Lys Gly Pro Glu Trp Val Ser Ser Ile Ser Gly Ser
            340                 345                 350

Gly Ser Asp Thr Leu Tyr Ala Asp Ser Val Lys Gly Arg Phe Thr Ile
            355                 360                 365

Ser Arg Asp Asn Ser Lys Asn Thr Leu Tyr Leu Gln Met Asn Ser Leu
370                 375                 380

Arg Pro Glu Asp Thr Ala Val Tyr Tyr Cys Thr Ile Gly Gly Ser Leu
385                 390                 395                 400

Ser Arg Ser Ser Gln Gly Thr Leu Val Thr Val Ser Ser Gly Gly Gly
            405                 410                 415

Gly Ser Gly Gly Gly Gly Ser Gly Gly Gly Gly Ser Gly Gly Gly Gly
            420                 425                 430

Ser Gly Gly Gly Gly Ser Gly Gly Gly Ser Gly Gly Gly Gly Ser
            435                 440                 445

Glu Val Gln Leu Val Glu Ser Gly Gly Leu Val Gln Pro Gly Gly
    450                 455                 460

Ser Leu Arg Leu Ser Cys Ala Ala Ser Gly Ser Thr Leu Asp Tyr Tyr
465                 470                 475                 480

Ala Ile Gly Trp Phe Arg Gln Ala Pro Gly Lys Glu Arg Glu Gly Val
            485                 490                 495

Ser Cys Thr Ser Asn Ser Gly Ser Thr Tyr Tyr Ala Asp Ser Val Lys
            500                 505                 510

Gly Arg Phe Thr Ala Ser Arg Asp Asn Ser Lys Asn Thr Val Tyr Leu
            515                 520                 525

Gln Met Asn Ser Leu Arg Pro Glu Asp Thr Ala Val Tyr Tyr Cys Val
            530                 535                 540

Ala Thr Ile Gly Cys Ala Thr Leu Gly Gly Thr Leu Asp Val Gln Arg
545                 550                 555                 560

Tyr Tyr Tyr Arg Gly Gln Gly Thr Leu Val Thr Val Ser Ser Ala
            565                 570                 575

<210> SEQ ID NO 54
<211> LENGTH: 585
<212> TYPE: PRT
<213> ORGANISM: Artificial Sequence
<220> FEATURE:
<223> OTHER INFORMATION: Nanobody Sequence

<400> SEQUENCE: 54

Asp Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Thr Asn
            20                  25                  30

Pro Met Tyr Trp Tyr Arg Gln Ala Pro Gly Lys Gln Arg Glu Leu Val
        35                  40                  45

Ala Ser Ile Ser Ser Arg Gly Ile Thr Asn Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Arg
            85                  90                  95

Leu Ala Ser Leu Ser Ser Gly Thr Val Tyr Trp Gly Gln Gly Thr Leu
            100                 105                 110

Val Thr Val Ser Ser Gly Gly Gly Gly Ser Gly Gly Gly Gly Ser Gly
            115                 120                 125

Gly Gly Gly Ser Gly Gly Gly Gly Ser Gly Gly Gly Gly Ser Gly Gly
 130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Ala Ala
            165                 170                 175

Ser Gly Arg Ile Phe Ser Ile Asn Arg Met Gly Trp Tyr Arg Gln Ala
            180                 185                 190

Pro Gly Lys Gln Arg Glu Leu Val Ala Gly Val Thr Ile Asn Ala Ile
            195                 200                 205

Thr Asn Tyr Ala Asp Ser Val Lys Gly Arg Phe Thr Ile Ser Arg Asp
 210                 215                 220

Asn Ser Lys Asn Thr Val Tyr Leu Gln Met Asn Ser Leu Arg Pro Glu
225                 230                 235                 240

Asp Thr Ala Val Tyr Tyr Cys His Ala Trp Ala Arg Ser Ser Gly Ser
            245                 250                 255

Ala Pro Tyr Ser Gln Asn Trp Gly Gln Gly Thr Leu Val Thr Val Ser
            260                 265                 270

Ser Gly Gly Gly Gly Ser Gly Gly Gly Gly Ser Gly Gly Gly Gly Ser
            275                 280                 285

Gly Gly Gly Gly Ser Gly Gly Gly Gly Ser Gly Gly Gly Gly Ser Gly
            290                 295                 300

Gly Gly Gly Ser Glu Val Gln Leu Val Glu Ser Gly Gly Gly Leu Val
305                 310                 315                 320

Gln Pro Gly Gly Ser Leu Arg Leu Ser Cys Ala Ala Ser Gly Phe Thr
            325                 330                 335

Phe Arg Ser Phe Gly Met Ser Trp Val Arg Gln Ala Pro Gly Lys Gly
            340                 345                 350

Pro Glu Trp Val Ser Ser Ile Ser Gly Ser Gly Ser Asp Thr Leu Tyr
            355                 360                 365

Ala Asp Ser Val Lys Gly Arg Phe Thr Ile Ser Arg Asp Asn Ser Lys
            370                 375                 380

Asn Thr Leu Tyr Leu Gln Met Asn Ser Leu Arg Pro Glu Asp Thr Ala
385                 390                 395                 400

Val Tyr Tyr Cys Thr Ile Gly Gly Ser Leu Ser Arg Ser Ser Gln Gly
            405                 410                 415

Thr Leu Val Thr Val Ser Ser Gly Gly Gly Gly Ser Gly Gly Gly Gly
            420                 425                 430

```
Ser Gly Gly Gly Ser Gly Gly Gly Ser Gly Gly Ser
        435             440             445

Gly Gly Gly Gly Ser Gly Gly Gly Ser Glu Val Gln Leu Val Glu
450                 455                 460

Ser Gly Gly Gly Leu Val Gln Pro Gly Ser Leu Arg Leu Ser Cys
465                 470                 475                 480

Ala Ala Ser Gly Ser Thr Leu Asp Tyr Tyr Ala Ile Gly Trp Phe Arg
                485                 490                 495

Gln Ala Pro Gly Lys Glu Arg Glu Val Ser Cys Thr Ser Asn Ser
                500                 505                 510

Gly Ser Thr Tyr Tyr Ala Asp Ser Val Lys Gly Arg Phe Thr Ala Ser
        515                 520                 525

Arg Asp Asn Ser Lys Asn Thr Val Tyr Leu Gln Met Asn Ser Leu Arg
    530                 535                 540

Pro Glu Asp Thr Ala Val Tyr Tyr Cys Val Ala Thr Ile Gly Cys Ala
545                 550                 555                 560

Thr Leu Gly Gly Thr Leu Asp Val Gln Arg Tyr Tyr Arg Gly Gln
                565                 570                 575

Gly Thr Leu Val Thr Val Ser Ser Ala
        580                 585

<210> SEQ ID NO 55
<211> LENGTH: 122
<212> TYPE: PRT
<213> ORGANISM: Artificial Sequence
<220> FEATURE:
<223> OTHER INFORMATION: Nanobody Sequence

<400> SEQUENCE: 55

Asp Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ala Arg Ile Ser Gly Ile Asp Gly Thr Thr Tyr Tyr Asp Glu Pro Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser Ala
        115                 120

<210> SEQ ID NO 56
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 56

Asp Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30
```

```
Asp Met Gly Trp Phe Arg Gln Ala Pro Gly Lys Gly Arg Glu Phe Val
         35                  40                  45

Ala Arg Ile Ser Gly Ile Asp Gly Thr Thr Tyr Tyr Asp Glu Pro Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser
        115                 120

<210> SEQ ID NO 57
<211> LENGTH: 25
<212> TYPE: PRT
<213> ORGANISM: Artificial Sequence
<220> FEATURE:
<223> OTHER INFORMATION: FR1

<400> SEQUENCE: 57

Asp Val Gln Leu Val Glu Ser Gly Gly Gly Val Val Gln Pro Gly Gly
1               5                   10                  15

Ser Leu Arg Leu Ser Cys Thr Ala Ser
            20                  25

<210> SEQ ID NO 58
<211> LENGTH: 10
<212> TYPE: PRT
<213> ORGANISM: Artificial Sequence
<220> FEATURE:
<223> OTHER INFORMATION: CDR1

<400> SEQUENCE: 58

Gly Phe Thr Phe Ser Thr Ala Asp Met Gly
1               5                   10

<210> SEQ ID NO 59
<211> LENGTH: 14
<212> TYPE: PRT
<213> ORGANISM: Artificial Sequence
<220> FEATURE:
<223> OTHER INFORMATION: FR2

<400> SEQUENCE: 59

Trp Phe Arg Gln Ala Pro Gly Lys Gly Arg Glu Phe Val Ala
1               5                   10

<210> SEQ ID NO 60
<211> LENGTH: 10
<212> TYPE: PRT
<213> ORGANISM: Artificial Sequence
<220> FEATURE:
<223> OTHER INFORMATION: CDR2

<400> SEQUENCE: 60

Arg Ile Ser Gly Ile Asp Gly Thr Thr Tyr
1               5                   10

<210> SEQ ID NO 61
<211> LENGTH: 39
<212> TYPE: PRT
<213> ORGANISM: Artificial Sequence
```

-continued

```
<220> FEATURE:
<223> OTHER INFORMATION: FR3

<400> SEQUENCE: 61

Tyr Asp Glu Pro Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Leu Tyr Tyr Cys Arg Ser
        35

<210> SEQ ID NO 62
<211> LENGTH: 12
<212> TYPE: PRT
<213> ORGANISM: Artificial Sequence
<220> FEATURE:
<223> OTHER INFORMATION: CDR3

<400> SEQUENCE: 62

Pro Arg Tyr Ala Asp Gln Trp Ser Ala Tyr Asp Tyr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: FR4

<400> SEQUENCE: 63

Trp Gly Gln Gly Thr Leu Val Thr Val Ser Ser
1               5                   10
```

METHOD FOR THE PRODUCTION OF IMMUNOGLOBULIN SINGLE VARIABLE DOMAINS

RELATED APPLICATIONS

This application is a continuation of U.S. patent application Ser. No. 16/076,314, filed Aug. 7, 2018, which is a national stage filing under 35 U.S.C. § 371 of International Patent Application Serial No. PCT/EP2017/053034, filed Feb. 10, 2017, which claims the benefit under 35 U.S.C. § 119(e) of U.S. Provisional Application Ser. No. 62/294,470, filed Feb. 12, 2016, the content of each of which is incorporated herein by reference in its entirety.

FIELD OF THE INVENTION

The present invention relates to a method for the manufacture of immunoglobulin single variable domains. More specifically, the present invention provides an improved method of producing immunoglobulin single variable domains wherein increased yields are obtained. The invention further provides nucleic acids, genetic constructs and host cells for use in the method of the invention as well as immunoglobulin single variable domains obtainable by the method of the invention.

BACKGROUND ART

For therapeutic applications, antibodies or antibody fragments must be of very high product quality. This puts high demands on the production processes for biological therapeutics. The production costs of these therapeutic compounds are strongly influenced by difficulties encountered during the production process. Low yields or lack of homogeneity will impact the economics of the production process, and hence, the costs for the therapeutic, overall.

The limitation of obtaining adequate yields of functional product has been reported for conventional immunoglobulins and their fragments across a broad range of expression systems, including in vitro translation, *E. coli*, yeasts such as e.g. *Saccharomyces cerevisiae* and *Pichia pastoris*, mammalian cells such as e.g. Chinese hamster ovary cells and baculovirus systems in insect cells. Amongst others, a bottleneck for antibody expression appears to be insufficient supply of light chains, inappropriate processing and folding in the endoplasmic reticulum (ER) and intracellular accumulation of heavy chain fragments. (Lange et al. 2001, J. Immunol. Methods 255: 103; Gasser et al. 2006, Biotechnol Bioeng. 94: 353; Gach et al. 2007, J. Biotechnol. 128: 735; Jenkins et al. 2009, Biotechnol. Appl. Biochem. 53: 73).

Intervention in the protein folding and secretory pathways has been described as one of the different strategies for improving the expression and quality of recombinant proteins, such as monoclonal antibodies (MAbs). However, overexpression of one or more components of the ER secretion machinery has yielded mixed results as regards improving productivity. Many challenges still exist to achieve consistently high yields in biopharmaceutical production. (Jenkins et al. 2009, Biotechnol. Appl. Biochem. 53: 73).

*Pichia pastoris* has been developed as a host for heterologous protein production. Although this host is known as a highly efficient expression system, especially for the production of complex proteins has turned out to have a rather low success rate. In *P. pastoris*, co-overexpression of Immunoglobulin binding protein (BiP) resulted in increased secretion levels of a scFv (A33scFv) by approximately threefold. In contrast, co-overexpression of protein disulfide isomerase (PDI1) had no apparent effect on secretion of A33scFv. Co-overexpressing BiP and PDI1 in *P. pastoris* did not increase A33scFv secretion and protein levels remained the same as the control strain (Damasceno et al. 2007, Appl. Microbiol. Biotechnol. 74: 381). Compared to that of a control strain, 2F5 Fab fragment productivity in *P. pastoris* could be improved ranging from 1.2 fold in the case of co-overexpression with BFR2 to 2.3 fold when SSE1 or KIN2 was overexpressed (Gasser et al. 2007, Appl. Environ. Microbiol. 73: 6499). Overexpression of basic leucine zipper (bZIP) transcription factor HAC1 had a slight effect (1.3 fold) on Mab 2F5 Fab fragment secretion in *P. pastoris*, while overexpression of PDI1 enabled an increase of the Fab level by 1.9 fold (Gasser et al. 2006, Biotechnol Bioeng. 94: 353). The authors conclude that sufficient supply of light chain and the formation of interchain disulfide bonds can be seen as a major rate limiting factors to Fab assembly and subsequent secretion.

In contrast to these difficulties observed with conventional four-chain antibodies or their fragments, including Fabs and scFvs, immunoglobulin single variable domain are known to be readily expressed and secreted from hosts like *E. coli* or *P. pastoris* at a sufficient rate and level. Immunoglobulin single variable domains do not possess interchain disulfide bridges and are characterized by formation of the antigen binding site by a single immunoglobulin variable domain, which does not require interaction with a further domain (e.g. in the form of VH/VL interaction) for antigen recognition. For example, production of Nanobodies, as one specific example of an immunoglobulin single variable domain, in prokaryotic hosts such as *E. coli* has been extensively described (see e.g. Ghahroudi et al. 1997, FEBS Letters 414: 521-526; Muyldermans 2001, J. Biotechnol. 74: 277-302; Vranken et al. 2002, Biochemistry 41: 8570-8579).

Production of Nanobodies in lower eukaryotic hosts such as *P. pastoris* has been described by Frenken et al. 2000 (J. Biotechnol. 78: 11-21), WO 94/25591, WO 2010/125187, WO 2012/056000 and WO 2012/152823.

Without any optimization of conditions, recombinant camelid single variable domains are routinely obtained at levels of 5-10 mg/l when expressed in *E. coli* grown in shaking culture flasks (Ghahroudi et al. 1997). With other expression systems it is even possible to obtain higher yields of VHH expression. Production levels of 9.3 mg/l/OD660 or ~250 mg secreted protein per litre of *Saccharomyces* yeast culture in shake flasks have been described by Frenken et al. 2000. More recently, Nanobody yields of more than 1 g per litre have been described (WO 2010/139808, WO 2012/152823) upon expression in *P. pastoris*.

WO 2010/125187 describes methods for producing a single variable domain in yeast (such as *P. pastoris*). The methods of WO 2010/125187 apply conditions that promote the formation of disulfide bridges in the single variable domain. One of the conditions proposed is enhancing the expression of a thiol isomerase (such as e.g. PDI1).

The fact that fully functional immunoglobulin single variable domains are readily produced in e.g. *E. coli* or yeast at a sufficient rate and level represents an important advantage of this immunoglobulin-format over conventional immunoglobulins.

SUMMARY OF THE INVENTION

Although VHH's and Nanobodies can be expressed using the expression systems described in the art for the expression of the same (WO 1994/25591; Ghahroudi et al. 1997, FEBS Letters 414: 521-526; Frenken et al. 2000, J. Biotechnol. 78: 11-21; Muyldermans 2001, J. Biotechnol. 74: 277-302; Vranken et al. 2002, Biochemistry 41: 8570-8579; WO 2010/125187; WO 2012/056000; WO 2012/152823 and other patent applications by Ablynx N.V.), the present inventors have found that in some cases (e.g. multivalent VHHs and Nanobodies and/or VHH's and Nanobodies with more than one disulfide bridge), the expression of VHH's and Nanobodies is more difficult leading to expression levels and/or yields much lower than expected. For example, the inventors have unexpectedly observed problems with the production of some therapeutic VHH1 type immunoglobulin single variable domains. Upon expression of these immunoglobulin single variable domains in *P. pastoris*, the present inventors obtained much lower yields of these immunoglobulin single variable domains compared to the yields normally obtained for VHH2 type and VHH3 type immunoglobulin single variable domains. Contrary to what was established for immunoglobulin single variable domains, expression of certain immunoglobulin single variable domains, such as e.g. VHH1 type immunoglobulin single variable domains, in *P. pastoris* did not result in high amounts of functional product.

The inventors have provided a solution to this problem which is as set out further herein. In addition, they observed that the proposed solution to improve the yield of immunoglobulin single variable domains is generally applicable, i.e. not only to improve the yield of immunoglobulin single variable domains of the VHH1 type, but also to other immunoglobulin single variable domains, such as e.g. immunoglobulin single variable domains of the VHH2 and VHH3 type.

Hence, in one aspect the present invention relates to the observation of the low yields upon expression in *P. pastoris* of certain immunoglobulin single variable domains.

In a further aspect of the present invention, methods are provided for the production of immunoglobulin single variable domains, wherein the yield of the obtained product is increased. These methods are also referred to herein as "method(s) of the invention". The present invention thus also provides methods of producing immunoglobulin single variable domains which overcome this unexpected problem. More in particular, the present inventors have found (by screening a library of auxiliary proteins) that enhancing the expression, in a *Pichia* host, of certain auxiliary proteins (PDI1 (SEQ ID NO: 5), Kar2p (SEQ ID NO: 4), RPP0 (SEQ ID NO: 6) and, in particular, HAC1spliced (SEQ ID NO: 14)) resulted in an increased yield of the immunoglobulin single variable domain when expressed in said *Pichia* host. Yield increases of more than 2 fold to more than 10 fold (or even more) were obtained.

In one aspect therefore, the present invention relates to a method for increasing the expression and/or production yield of immunoglobulin single variable domains in *Pichia* (such as *P. pastoris*). In the method of the invention, the immunoglobulin single variable domain is expressed while simultaneously the expression of HAC1spliced is enhanced.

The immunoglobulin single variable domains used in the method of the present invention may form part of a polypeptide (also referred to as "polypeptide of the invention"), which may comprise or essentially consist of one or more (i.e. at least one) immunoglobulin single variable domains and which may optionally further comprise one or more further amino acid sequences (all optionally linked via one or more suitable linkers).

Thus, the present invention provides methods for producing, in a *Pichia* host (such as *P. pastoris*), a polypeptide comprising or essentially consisting of at least one immunoglobulin single variable domain (referred to herein as "polypeptide of the invention"), said method comprising the step of expressing, in the *Pichia* host, the polypeptide of the invention and enhancing, in said *Pichia* host, the expression of HAC1spliced protein. The method of the invention may further comprise the step of isolating and/or purifying the polypeptide of the invention.

The method of the present invention is especially suited for immunoglobulin single variable domains and polypeptides of the invention that are not easily expressible in *Pichia*, such as *P. pastoris*, or that are expressed with very low yields, when expressed under standard conditions (as further defined herein); and for which thus, upon expression of these immunoglobulin single variable domains or polypeptides of the invention in *Pichia*, such as *P. pastoris*, sufficient amounts of immunoglobulin single variable domain and/or polypeptide cannot be obtained. Accordingly, in one aspect, the immunoglobulin single variable domain and/or polypeptide of the invention is selected from the immunoglobulin single variable domains and/or polypeptides for which, upon expression in a *Pichia* host (such as *P. pastoris*) under standard *Pichia* expression conditions (as further defined herein), a yield is obtained of 0.5 g/l or lower, such as 0.4 g/L, 0.3 g/L, 0.2 g/L, 0.1 g/L, 0.05 g/L, 0.01 g/L, or even less. In another aspect, the immunoglobulin single variable domain and/or polypeptide of the invention is selected from the immunoglobulin single variable domains and/or polypeptides for which, upon expression in a *Pichia* host (such as *P. pastoris*) under *Pichia* expression conditions (as further defined herein), the yield obtained shows an inverse correlation (as further defined herein) with the copy number of the nucleic acid encoding said immunoglobulin single variable domain and/or polypeptide.

In a specific aspect of the invention, the method of the present invention is especially suited for immunoglobulin single variable domains and polypeptides of the invention that are easily expressible in *Pichia*, such as *P. pastoris*. Accordingly, in one aspect, the immunoglobulin single variable domain and/or polypeptide of the invention is selected from the immunoglobulin single variable domains and/or polypeptides for which, upon expression in a *Pichia* host (such as *P. pastoris*) under standard *Pichia* expression conditions (as further defined herein), a yield is obtained of 0.5 g/l or higher, such as 1 g/L, 2 g/L, 3 g/L, 4 g/L, 5 g/L, 6 g/L, or even higher.

In the above method, the polypeptide of the invention may comprise or essentially consist of two or more immunoglobulin single variable domains. Such polypeptides are also referred to as multivalent polypeptides. Accordingly, in a specific aspect, the polypeptide of the invention to be expressed by the method of the invention, is a multivalent polypeptide.

Alternatively, the polypeptide expressed by the method of the invention may comprise or essentially consist of one immunoglobulin single variable domain. Such polypeptide will also be referred to herein as a monovalent polypeptide. Accordingly, in another specific aspect, the polypeptide of the invention to be expressed by the method of the invention, is a monovalent polypeptide.

In the above method, the immunoglobulin single variable domain (potentially present in the polypeptide of the invention) can be (without being limited) an immunoglobulin single variable domain that is a light chain variable domain or a heavy chain variable domain, more specifically an immunoglobulin single variable domain which is a heavy chain variable domain that is derived from a conventional four-chain antibody or a heavy chain variable domain that is derived from a heavy chain antibody, in particular a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody (including but not limited to a VHH sequence), preferably a Nanobody.

In a preferred aspect, the Nanobody expressed in the method of the invention is a VHH sequence (VHH), a (partially) humanized VHH sequence (humanized VHH), a camelized heavy chain variable domain (camelized VH) or a Nanobody, that has been obtained by techniques such as affinity maturation.

In another specific aspect of the invention, the immunoglobulin single variable domain (potentially present in the polypeptide of the invention), expressed in the method of the invention, comprises at least two disulfide bridges. In another specific aspect, the immunoglobulin single variable domain belongs to the group of VHH1 type immunoglobulin single variable domains.

In another aspect, the immunoglobulin single variable domain (potentially present in the polypeptide of the invention), does not belong to the group of VHH1 type immunoglobulin single variable domains, but belongs to another group of immunoglobulin single variable domains, such as the VHH2, VHH3 or any other type immunoglobulin single variable domains.

In yet another specific aspect, the immunoglobulin single variable domain (potentially present in the polypeptide of the invention), expressed in the method of the invention, specifically binds c-Met, such as e.g. the immunoglobulin single variable domains described in WO 2012/042026 and WO 2013/045707. Thus, polypeptides of the invention that comprise at least one immunoglobulin single variable domain that specifically binds c-Met, wherein said immunoglobulin single variable domain comprises two disulfide bridges, form a specific but non-limiting aspect of the invention. A particular Nanobody for use in the method of the invention is SEQ ID NO: 49.

In a preferred aspect, the one or more immunoglobulin single variable domain(s) (potentially present in the polypeptide of the invention), expressed in the method of the invention, specifically bind TNF, such as e.g. the immunoglobulin single variable domains described in US provisional application U.S. 62/254,375 of Ablynx NV (see also PCT/EP2016/077595).

Thus, polypeptides of the invention that comprise one or more (at least one) immunoglobulin single variable domain that specifically bind(s) TNF form a specific and non-limiting aspect of the invention.

In a specific aspect, the polypeptide of the invention, expressed in the method of the invention, comprises or essentially consists of one immunoglobulin single variable domain. Such polypeptide will also be referred to herein as a monovalent polypeptide. Therefore, in a preferred aspect, in the method of the invention, the polypeptide is a monovalent polypeptide.

Such a monovalent polypeptide, comprising or essentially consisting of one immunoglobulin single variable domain, may comprise at least two disulfide bridges. Accordingly, the immunoglobulin single variable domain that specifically binds TNF belongs to the VHH1 type immunoglobulin single variable domains.

Alternatively, the immunoglobulin single variable domain comprises one disulfide bridge. Accordingly, in a preferred aspect, the immunoglobulin single variable domain that specifically binds TNF does not belong to the group of VHH1 type immunoglobulin single variable domains, but belongs to another group of immunoglobulin single variable domains, such as the VHH2, VHH3 or any other type immunoglobulin single variable domains.

In a preferred aspect, in the method of the present invention, the immunoglobulin single variable domain essentially consists of 4 framework regions (FR1 to FR4, respectively) and 3 complementarity determining regions (CDR1 to CDR3, respectively), in which CDR1 is SEQ ID NO: 58, CDR2 is SEQ ID NO: 60 and CDR3 is SEQ ID NO: 62.

Particular Nanobodies for use in the method of the invention are chosen from the group consisting of SEQ ID NO's: 55 and 56.

The polypeptide of the invention comprising or essentially consisting of one or more immunoglobulin single variable domains may further comprise one or more other residues or binding units, optionally linked via one or more peptidic linkers.

In one aspect, said one or more other residues may be effective in preventing or reducing binding of antibodies pre-existing in the serum (so-called "pre-existing antibodies") to the polypeptides of the invention (as is further described herein).

In another aspect, said one or more other residues or binding units may also be chosen from the group consisting of immunoglobulin single variable domains, domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies. Polypeptides comprising or essentially consisting of two or more binding units are also referred to as multivalent constructs.

In a specific aspect of the invention, the polypeptide comprising or essentially consisting of one or more immunoglobulin single variable domains expressed in the method of the invention is a multivalent construct.

In another specific aspect, the polypeptide of the invention is a bivalent, trivalent or tetravalent polypeptide.

In a particular aspect of the invention, said one or more other binding units may provide the polypeptide of the invention with increased half-life, compared to the polypeptide without said one or more binding units. Without being limiting, said one or more other binding units that provides the polypeptide with increased half-life may be chosen from the group consisting of binding units that can bind to serum albumin (such as human serum albumin) or a serum immunoglobulin (such as IgG).

In the method of the invention, the expression of HAC1spliced may be enhanced by introduction, into the *Pichia* host, of one or more nucleic acid(s) encoding HAC1spliced protein. In another aspect, the expression of HAC1spliced protein may be enhanced by introduction, into the *Pichia* host, of one or more strong promoter(s) controlling the expression of a nucleic acid encoding HAC1spliced protein.

The polypeptide comprising or essentially consisting of the at least one immunoglobulin single variable domain and the HAC1spliced protein may be expressed from the same genetic construct. In this particular aspect of the invention, transcription of the nucleic acid encoding the polypeptide comprising or essentially consisting of the at least one immunoglobulin single variable domain and transcription of the nucleic acid encoding the HAC1spliced protein may be controlled by the same promoter or by a different promoter. The nucleic acid encoding the HAC1spliced protein may be located on the genetic construct downstream of the nucleic acid encoding the polypeptide comprising or essentially consisting of the at least one immunoglobulin single variable domain. In the alternative, the nucleic acid encoding the polypeptide comprising or essentially consisting of the at least one immunoglobulin single variable domain may be located on the genetic construct downstream of the nucleic acid encoding HAC1spliced protein.

In another aspect of the invention, the polypeptide comprising or essentially consisting of the at least one immunoglobulin single variable domain and the HAC1spliced protein may be expressed from different genetic constructs. In this particular aspect of the invention, transcription of the nucleic acid encoding the polypeptide comprising or essentially consisting of the at least one immunoglobulin single variable domain and transcription of the nucleic acid encoding the HAC1spliced protein from the different genetic constructs may be controlled by two separate promoters which may be the same or different.

The polypeptide comprising or essentially consisting of the at least one immunoglobulin single variable domain and/or the HAC1spliced protein can also be expressed from the chromosome. In this particular aspect, the expression of HAC1spliced protein may be enhanced by introduction of a strong promoter into the chromosome of the *Pichia* host. In the alternative, one or more nucleic acid(s) encoding HAC1spliced protein controlled by a strong promoter may be introduced into the chromosome of the *Pichia* host. Also one or more nucleic acids encoding the polypeptide comprising or essentially consisting of the at least one immunoglobulin single variable domain may be introduced into the chromosome of the *Pichia* host.

In one aspect of the invention, the number of the nucleic acid(s) encoding the polypeptide comprising or essentially consisting of an immunoglobulin single variable domain is one. In another aspect of the invention the number of the nucleic acid(s) encoding the polypeptide comprising or essentially consisting of an immunoglobulin single variable domain is two or more.

In another aspect, the invention also relates to a nucleic acid that encodes a polypeptide of the invention (or a suitable fragment thereof) and that encodes HAC1spliced protein. Such a nucleic acid will also be referred to herein as a "nucleic acid of the invention" and may for example be in the form of a genetic construct, as further described herein.

Accordingly, the present invention also relates to a nucleic acid of the invention that is in the form of a genetic construct. Such a genetic construct will also be referred to herein as a "genetic construct of the invention" and thus comprises a nucleic acid encoding a polypeptide of the invention and a nucleic acid encoding the HAC1spliced protein. In a specific aspect, in such a genetic construct of the invention, the nucleic acid encoding the HAC1spliced protein is located downstream of the nucleic acid encoding the polypeptide of the invention. In another specific aspect, in such a genetic construct of the invention, the nucleic acid encoding the polypeptide of the invention is located downstream of the nucleic acid encoding the HAC1spliced protein. In the genetic construct of the invention, expression of the nucleic acid encoding the polypeptide of the invention and expression of the nucleic acid encoding the HAC1spliced protein may be controlled by the same promoter or by a different promoter. The promoter may be a constitutive or an inducible promoter.

In one aspect of the invention, the copy number of the nucleic acid encoding the polypeptide of the invention is one. In another aspect of the invention the copy number of the nucleic acid encoding the polypeptide of the invention is two or more.

In one aspect of the invention, the number of auxiliary proteins is one, wherein the auxiliary protein is HAC1spliced. In another aspect of the invention, the expression of one or more additional auxiliary proteins is enhanced. In yet another aspect of the invention, the additional auxiliary protein(s) is(are) selected from PDI1, Kar2p and RPP0. In yet another aspect of the invention the number of auxiliary proteins is two. In yet another aspect of the invention, the number of auxiliary proteins is more than two, such as three or more. In yet another aspect, the two or more auxiliary proteins are selected from the following combination of auxiliary proteins:

PDI1 and HAC1spliced;
Kar2p and HAC1spliced;
RPP0 and HAC1spliced;
PDI1, Kar2p and HAC1spliced;
PDI1, RPP0 and HAC1spliced;
Kar2p, RPP0 and HAC1spliced; and
PDI1, Kar2p, RPP0 and HAC1spliced.

In a preferred aspect, expression of following auxiliary proteins is enhanced:

PDI1, Kar2p and Hac1spliced; or
Kar2p, RPP0 and Hac1spliced.

In a preferred aspect of the invention, the auxiliary protein is HAC1spliced (SEQ ID NO: 14).

In another preferred aspect, an additional auxiliary protein is selected from PDI1 (SEQ ID NO: 5), Kar2p (SEQ ID NO: 4), RPP0 (SEQ ID NO: 6) and Hac1spliced (SEQ ID NO: 14).

In another preferred aspect, the two or more auxiliary proteins are selected from the following combination of auxiliary proteins:

PDI1 (SEQ ID NO: 5) and Hac1spliced (SEQ ID NO: 14);
Kar2p (SEQ ID NO: 4) and Hac1spliced (SEQ ID NO: 14);
RPP0 (SEQ ID NO: 6) and Hac1spliced (SEQ ID NO: 14);
PDI1 (SEQ ID NO: 5), Kar2p (SEQ ID NO: 4) and Hac1spliced (SEQ ID NO: 14);
PDI1 (SEQ ID NO: 5), RPP0 (SEQ ID NO: 6) and Hac1spliced (SEQ ID NO: 14);
Kar2p (SEQ ID NO: 4), RPP0 (SEQ ID NO: 6) and Hac1spliced (SEQ ID NO: 14); and
PDI1 (SEQ ID NO: 5), Kar2p (SEQ ID NO: 4), RPP0 (SEQ ID NO: 6) and Hac1spliced (SEQ ID NO: 14).

In another aspect, the present invention relates to the introduction of the nucleic acid and genetic construct of the invention in a *Pichia* host, also referred to herein as "*Pichia* host of the invention". In addition to plasmid or vector transformation of the *Pichia* host, chromosomal transformation of the *Pichia* host is also encompassed by the present invention. A strong (inducible) promoter (instead of the native promoter of a native auxiliary protein) may be introduced on the chromosome of the *Pichia* host; or another copy of an auxiliary protein gene sequence under control of another (strong) promoter may be introduced into the chromosome.

In another aspect, the invention relates to a *Pichia* host that expresses (or that under suitable circumstances is capable of expressing) a polypeptide of the invention and wherein the expression of HAC1spliced is enhanced; and/or that contains a nucleic acid of the invention and/or a genetic construct of the invention.

In a preferred aspect, the *Pichia* host is *Pichia pastoris*.

In another preferred aspect, the *Pichia pastoris* strain is selected from *Pichia pastoris* X33 and *Pichia pastoris* NRRL Y-11430.

The invention further relates to methods for the preparation of the nucleic acids of the invention, the genetic constructs of the invention and the *Pichia* hosts of the invention; and to the uses of said nucleic acids of the invention, genetic constructs of the invention and *Pichia* hosts of the invention for the production of immunoglobulin single variable domains and polypeptides comprising the same.

The invention further relates to a polypeptide and/or immunoglobulin single variable domain obtainable by any of the methods as set forth herein, pharmaceutical compositions and other compositions comprising such polypeptides and/or an immunoglobulin single variable domains, and therapeutic uses of the polypeptides and/or an immunoglobulin single variable domains or methods of treatment comprising the use of the polypeptides and/or an immunoglobulin single variable domains.

4 clones (6H1, 4C2, 5A6, 9C4) were found to secrete significantly higher levels of Nanobody A in shake flask compared to their corresponding reference clones without auxiliary protein (Ref CN=1 and Ref CN>1). Ref: reference clone with indicated copy number of the Nanobody A expression cassette inserted in the genome.

Figure 3:
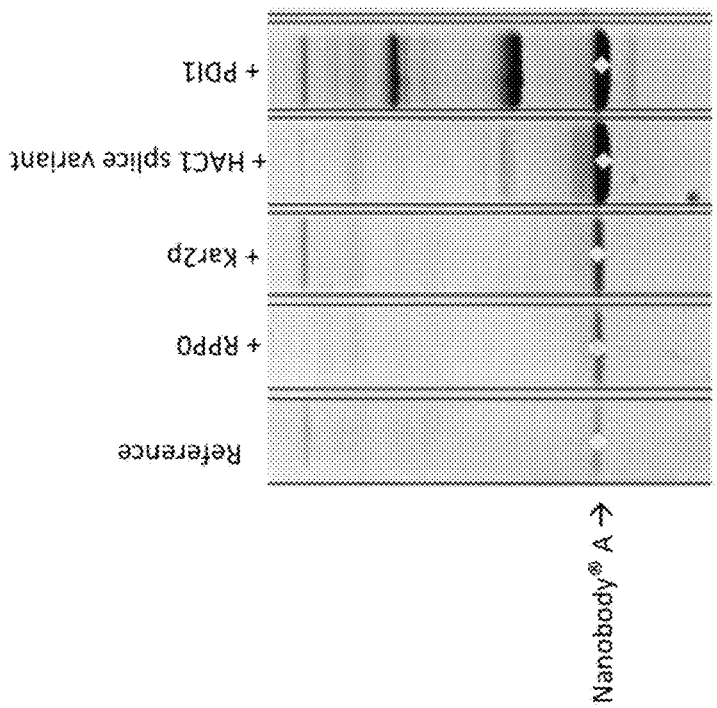

FIG. 3: Shake flask expression of the reference clone with more than 1 copy of the Nanobody A expression cassette transformed with one of the auxiliary proteins Kar2p, RPP0, Hac1 splice variant or PDI1. Nanobody yields were analysed on SDS-PAGE and compared to the Nanobody yield by the reference clone (without auxiliary protein). Densitometry analysis for relative quantification of the bands corresponding to intact Nanobody product was performed. Quantification of band volumes was done using Imagequant software (GE Healthcare).

DETAILED DESCRIPTION OF THE INVENTION

Definitions

Unless indicated or defined otherwise, all terms used have their usual meaning in the art, which will be clear to the skilled person. Reference is for example made to the standard handbooks, such as Sambrook et al. 1989 (Molecular Cloning: A Laboratory Manual, $2^{nd}$ Ed., Vols. 1-3, Cold Spring Harbor Laboratory Press), Ausubel et al. 1987 (Current protocols in molecular biology, Green Publishing and Wiley Interscience, New York), Lewin 1985 (Genes II, John Wiley & Sons, New York, N.Y.), Old et al. 1981 (Principles of Gene Manipulation: An Introduction to Genetic Engineering, $2^{nd}$ Ed., University of California Press, Berkeley, Calif.), Roitt et al. 2001 (Immunology, $6^{th}$ Ed., Mosby/Elsevier, Edinburgh), Roitt et al. 2001 (Roitt's Essential Immunology, 10th Ed., Blackwell Publishing, UK), and Janeway et al. 2005 (Immunobiology, $6^{th}$ Ed., Garland Science Publishing/Churchill Livingstone, N.Y.), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta 2006 (Adv. Drug Deliv. Rev. 58: 640), Levin and Weiss 2006 (Mol. Biosyst. 2: 49), Irving et al. 2001 (J. Immunol. Methods 248: 31), Schmitz et al. 2000 (Placenta 21 Suppl. A: S106), Gonzales et al. 2005 (Tumour Biol. 26: 31), which describe techniques for protein engineering, such as affinity maturation and other techniques for improving the specificity and other desired properties of proteins such as immunoglobulins.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain, this may mean that the immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist of" is meant that the immunoglobulin single variable domain used in the method of the invention either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

A nucleic acid or amino acid is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined using a suitable technique, such as a suitable chromatographical technique, such as polyacrylamide-gel electrophoresis.

The terms "expression (of)" or "expressing" a polypeptide such as an immunoglobulin single variable domain and/or polypeptide of the invention or an auxiliary protein is the process by which information from a gene is used in the synthesis of a functional gene product (i.e. the immunoglobulin single variable domain and/or polypeptide of the invention or the auxiliary protein). When an auxiliary protein or a polypeptide such as an immunoglobulin single variable domain and/or polypeptide of the invention is said to be "expressed from" a nucleic acid, genetic construct or chromosome, it is synthesized through a process by which information from a nucleic acid, genetic construct or chromosome is used for the synthesis of the functional gene product (i.e. the immunoglobulin single variable domain and/or polypeptide of the invention or the auxiliary protein). When proteins are said to be "co-expressed", said proteins are expressed simultaneously. "Enhancing the expression" of a gene means that the production of the gene product (e.g. the auxiliary protein) is increased compared to the production of the gene product without enhancing the expression of the gene. As is further explained, expression of a particular gene can be enhanced by various means including the use of suitable control sequences, e.g. a strong promoter, and/or increasing the gene dose, e.g. by increasing the copy number of the respective gene.

The term "yield" as used in the present invention, relates to the amount of immunoglobulin single variable domain and/or polypeptide of the invention being produced in functional form upon expression in the *Pichia* host. The yield is expressed as g (gram) immunoglobulin single variable domain and/or polypeptide of the invention per L (litre) medium.

Immunoglobulin Single Variable Domain

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). In addition, the term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments (such as Fabs, scFvs, etc.), wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of an immunoglobulin single variable domain is formed by a single VH or VL domain. Hence, the antigen binding site of an immunoglobulin single variable domain is formed by no more than three CDRs.

The term "immunoglobulin single variable domain" and "single variable domain" hence does not comprise conventional immunoglobulins or their fragments which require interaction of at least two variable domains for the formation of an antigen binding site. However, these terms do comprise fragments of conventional immunoglobulins wherein the antigen binding site is formed by a single variable domain.

Generally, single variable domains will be amino acids that essentially consist of 4 framework regions (FR1 to FR4 respectively) and 3 complementarity determining regions (CDR1 to CDR3 respectively); or any suitable fragment of such an amino acid (which will then usually contain at least some of the amino acid residues that form at least one of the CDR's). Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a VL-sequence) or a suitable fragment thereof; or a heavy chain variable domain sequence (e.g. a VH-sequence or VHH sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a VH/VL interaction—to form a functional antigen binding domain).

In one embodiment of the invention, the immunoglobulin single variable domains are light chain variable domain sequences (e.g. a VL-sequence), or heavy chain variable domain sequences (e.g. a VH-sequence); more specifically, the immunoglobulin single variable domains can be heavy chain variable domain sequences that are derived from a conventional four-chain antibody or heavy chain variable domain sequences that are derived from a heavy chain antibody.

For example, the single variable domain or immunoglobulin single variable domain (or an amino acid that is suitable for use as an immunoglobulin single variable domain) may be a (single) domain antibody (or an amino acid that is suitable for use as a (single) domain antibody), a "dAb" or dAb (or an amino acid that is suitable for use as a dAb) or a Nanobody (as defined herein, and including but not limited to a VHH); other single variable domains, or any suitable fragment of any one thereof. For a general description of (single) domain antibodies, reference is also made to the prior art cited herein, as well as to EP 0368684. For the term "dAb's", reference is for example made to Ward et al. 1989 (Nature 341: 544), to Holt et al. 2003 (Trends Biotechnol. 21: 484); as well as to for example WO 04/068820, WO 06/030220, WO 06/003388 and other published patent applications of Domantis Ltd. It should also be noted that, although less preferred in the context of the present invention because they are not of mammalian origin, single variable domains can be derived from certain species of shark (for example, the so-called "IgNAR domains", see for example WO 05/18629).

In particular, the immunoglobulin single variable domain may be a Nanobody (as defined herein) or a suitable fragment thereof. [Note: Nanobody, Nanobodies and Nanoclone are registered trademarks of Ablynx N.V.] For a general description of Nanobodies, reference is made to the prior art cited herein, such as e.g. described in WO 08/020079 (page 16).

The amino acid sequence and structure of an immunoglobulin sequence, in particular a Nanobody can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

The total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein.

For a further description of VHH's and Nanobodies, reference is made to the review article by Muyldermans 2001 (Rev. Mol. Biotechnol. 74: 277), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHHs and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164.

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g. described in Davies and Riechmann 1994 (FEBS 339: 285), 1995 (Biotechonol. 13: 475) and 1996 (Prot. Eng. 9: 531) and Riechmann and Muyldermans 1999 (J. Immunol. Methods 231: 25).

The term "immunoglobulin single variable domain" encompasses immunoglobulin sequences of different origin, comprising mouse, rat, rabbit, donkey, human and camelid immunoglobulin sequences. It also includes fully human, humanized or chimeric immunoglobulin sequences. For example, it comprises camelid immunoglobulin sequences and humanized camelid immunoglobulin sequences, or camelized immunoglobulin single variable domains, e.g. camelized dAbs as described by Ward et al (see for example WO 94/04678 and Davies and Riechmann 1994, 1995 and 1996).

The invention may be used for the expression or production of any of the immunoglobulin single variable domains described herein. The invention may also be used for the expression or production of polypeptides of the invention (i.e. polypeptides that comprise or essentially consist of such an immunoglobulin single variable domain). In a particular aspect, the invention may be used for the expression or production of immunoglobulin single variable domains that comprise two disulfide bridges. The invention may also be used for the expression or production of polypeptides of the invention (i.e. polypeptides that comprise or essentially consist of such an immunoglobulin single variable domain) with two disulfide bridges. The invention may also be used for the expression or production of polypeptides of the invention (i.e. polypeptides that comprise or essentially consist of such an immunoglobulin single variable domain with two disulfide bridges).

It is known that all VHH's contain at least one disulfide bridge, between the cysteine residue at position 22 and the cysteine residue at position 92 (numbering according to Kabat, see the patent applications of Ablynx N.V. and Muyldermans and Lauwereys 1999, J. Mol. Recognit. 12: 131). Although most VHH's contain only this single disulfide bridge, it is also known that some VHH's contain a total of two (or in exceptional cases three) disulfide bridges. For example, a class of VHH's (and Nanobodies) referred to as "VHH-1 type", "VHH-1 class", or the like (as further defined herein) commonly has a second disulfide bridge between the cysteine residue in CDR2 at position 50 and a cysteine residue present in CDR3 (or in exceptional cases in CDR1 or CDR2). Also, some VHH's derived from camels or dromedaries often have a disulfide bridges between a cysteine residue present in CDR1 (or at position 45 in FR2) and a cysteine residue present in CDR3 (Vu et al. 1997, Mol. Immunol. 34: 1121; Muyldermans and Lauwereys 1999). Some VHH's derived from llamas sometimes have a disulfide bridge between cysteine residues present in CDR1 (such as at position 33) and a cysteine residue present in CDR3 (Vu et al., 1997).

In one specific but non-limiting aspect, the immunoglobulin single variable domain comprises a disulfide bridge between the cysteine residue at position 22 and the cysteine residue at position 92, and further comprises a disulfide bridge that is formed between a cysteine residue in one of the framework regions and a cysteine residue in one of the CDR regions.

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue in one of the framework regions and a cysteine residue in CDR3.

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue in framework two (FR2) and a cysteine residue in CDR3.

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue at position 45 in framework two (FR2) and a cysteine residue in CDR3 (as in some VHH's derived from camels and dromedaries).

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue in one CDR and a cysteine residue in another CDR.

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue in CDR3 and a cysteine residue in another CDR (in particular in CDR1, as in some VHH's derived from camels, dromedaries and llamas).

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue in CDR1 and a cysteine residue in another CDR.

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue in CDR1 and a cysteine residue in CDR1.

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue in CDR1 and a cysteine residue in CDR3 (as in some VHH's derived from camels, dromedaries and llamas).

In another specific but non-limiting aspect, the immunoglobulin single variable domain comprises a disulfide bridge between the cysteine residue at position 22 and the cysteine residue at position 92, and further comprises a disulfide bridge that is formed between a cysteine at position 33 and a cysteine residue in CDR3 (as in some VHH's derived from camels, dromedaries and llamas).

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue in CDR2 and a cysteine residue in another CDR.

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue in CDR2 and a cysteine residue in CDR2.

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue in CDR2 and a cysteine residue in CDR3 (as in some VHH's derived from llamas).

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue at position 50 and a cysteine residue in another CDR, such as CDR1, CDR2 or CDR3 (as in VHH's and Nanobodies of the VHH1 type).

In another specific but non-limiting aspect, the immunoglobulin single variable domain comprises a disulfide bridge between the cysteine residue at position 22 and the cysteine residue at position 92, and further comprises a disulfide bridge that is formed between a cysteine residue at position 50 and a cysteine residue in CDR3 (as in VHH's and Nanobodies of the VHH1 type).

In a preferred but non-limiting embodiment, the immunoglobulin single variable domain may be a "VHH1 type immunoglobulin single variable domain". An amino acid such as e.g. an immunoglobulin single variable domain or polypeptide of the invention is said to be a "VHH1 type immunoglobulin single variable domain" or "VHH type 1 sequence", if said VHH1 type immunoglobulin single variable domain or VHH type 1 sequence has 85% identity (using the blastp algorithm with standard setting, i.e. blosom62 scoring matrix) to the VHH1 consensus sequence (SEQ ID NO: 46):

```
QVQLVESGGGLVQPGGSLRLSCAASGFTLDYYAIGWFRQAPGKEREGVSC
ISSSDGSTYYADSVKGRFTISRDNAKNTVYLQMNSLKPEDTAVYYCAA)
``` and mandatorily has a cysteine in position 50, i.e. Cys50 (using Kabat numbering). These VHH1 type immunoglobulin single variable domains generally have (or are capable of forming) a disulfide bridge between Cys50 and a cysteine residue in CDR3 (or in exceptional cases CDR1 or CDR2).

An amino acid sequence such as e.g. an immunoglobulin single variable domain or polypeptide of the invention is said to be a "VHH2 type immunoglobulin single variable domain" or "VHH type 2 sequence", if said VHH2 type immunoglobulin single variable domain or VHH type 2 sequence has 85% identity (using the blastp algorithm with standard setting, i.e. blosom62 scoring matrix) to the VHH2 consensus sequence (SEQ ID NO: 47):

QVQLVESGGGLVQAGGSLRLSCAASGSIFSINAMGWYRQAPGKQRELVAA
ITSGGSTNYADSVKGRFTISRDNAKNTVYLQMNSLKPEDTAVYYCNA.

An amino acid sequence such as e.g. an immunoglobulin single variable domain or polypeptide according to the invention is said to be a "VHH3 type immunoglobulin single variable domain" or "VHH type 3 sequence", if said VHH3 type immunoglobulin single variable domain or VHH type 3 sequence has 85% identity (using the blastp algorithm with standard setting, i.e. blosom62 scoring matrix) to the VHH3 consensus sequence (SEQ ID NO: 48):

QVQLVESGGGLVQAGGSLRLSCAASGRTFSSYAMGWFRQAPGKEREFVAA
ISWSGGSTYYADSVKGRFTISRDNAKNTVYLQMNSLKPEDTAVYYCAA.

Although the invention is particularly suited for expression of VHH1 (where the presence of two disulfide bridges is very common), it should be noted that it can also be applied to the expression of VHH2 or VHH3 (which may or may not also comprise two disulfide bridges, although this is less common).

For a general description and for some non-limiting examples of Nanobodies (and of polypeptides comprising the same) that are directed against c-Met and that can be expressed/produced using the methods described herein, reference is made to WO 2012/042026 and WO 2013/045707.

For a general description and for some non-limiting examples of Nanobodies (and of polypeptides comprising the same) that are directed against TNF and that can be expressed/produced using the methods described herein, reference is made to US provisional application U.S. 62/254,375 of Ablynx NV (see also PCT/EP2016/077595).

The inventors also expect that this teaching is not only particularly applicable to VHH's and Nanobodies with two or more disulfide bridges such as VHH-1's, but also to other immunoglobulin single variable domains that comprise two or more disulfide bridges (such as (single) domain antibodies, dAb's, IgNAR domains from sharks, etc.).

Polypeptide of the Invention

The immunoglobulin single variable domains prepared in the method of the invention may form part of a protein or polypeptide (referred to herein as "polypeptide of the invention"), which may comprise or essentially consist of one or more (at least one) immunoglobulin single variable domains and which may optionally further comprise one or more further amino acid sequences (all optionally linked via one or more suitable linkers). The term "immunoglobulin single variable domain" may also encompass such polypeptides of the invention. The one or more immunoglobulin single variable domains may be used as a binding unit in such a protein or polypeptide, which may optionally contain one or more further amino acids that can serve as a binding unit, so as to provide a monovalent, multivalent or multispecific polypeptide of the invention, respectively (for multivalent and multispecific polypeptides containing one or more VHH domains and their preparation, reference is also made to Conrath et al. 2001 (J. Biol. Chem. 276: 7346), as well as to for example WO 96/34103, WO 99/23221 and WO 2010/115998).

The polypeptides of the invention may comprise or essentially consist of one immunoglobulin single variable domain, as outlined above. Such polypeptides are also referred to herein as monovalent polypeptides.

The polypeptides of the invention may also encompass constructs comprising two or more antigen binding units in the form of single variable domains, as outlined above. For example, two (or more) immunoglobulin single variable domains with the same or different antigen specificity can be linked to form e.g. a bivalent, trivalent or multivalent construct. By combining immunoglobulin single variable domains of two or more specificities, bispecific, trispecific, etc. constructs can be formed. For example, an immunoglobulin single variable domain according to the invention may comprise two or three immunoglobulin single variable domains directed against the same target, or one or two immunoglobulin single variable domains directed against target A, and one immunoglobulin single variable domain against target B. Such constructs and modifications thereof, which the skilled person can readily envisage, are all encompassed by the term polypeptide of the invention as used herein.

Moreover, also prepared in the method of the present invention are fused immunoglobulin sequences, comprising tags or other functional moieties, e.g. toxins, labels, radiochemicals, etc.

In another aspect, the polypeptide of the invention that comprises or essentially consists of one or more immunoglobulin single variable domains (or suitable fragments thereof), may further comprise one or more other groups, residues, moieties or binding units. Such further groups, residues, moieties, binding units or amino acid sequences may or may not provide further functionality to the immunoglobulin single variable domain (and/or to the polypeptide in which it is present) and may or may not modify the properties of the immunoglobulin single variable domain.

For example, such further groups, residues, moieties or binding units may be one or more additional amino acids, such that the compound, construct or polypeptide is a (fusion) protein or (fusion) polypeptide. In a preferred but non-limiting aspect, said one or more other groups, residues, moieties or binding units are immunoglobulins. Even more preferably, said one or more other groups, residues, moieties or binding units are chosen from the group consisting of domain antibodies, amino acids that are suitable for use as a domain antibody, single domain antibodies, amino acids that are suitable for use as a single domain antibody, "dAb"'s, amino acids that are suitable for use as a dAb, or Nanobodies.

Alternatively, such groups, residues, moieties or binding units may for example be chemical groups, residues, moieties, which may or may not by themselves be biologically and/or pharmacologically active. For example, and without limitation, such groups may be linked to the one or more immunoglobulin single variable domain so as to provide a "derivative" of the immunoglobulin single variable domain.

In a preferred but non-limiting aspect, said further residues may be effective in preventing or reducing binding of so-called "pre-existing antibodies" to the polypeptides of the invention. For this purpose, the polypeptides and constructs of the invention may contain a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I), for which reference is made to the following co-pending US provisional applications, all entitled "Improved immunoglobulin variable domains": U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014 (all assigned to Ablynx N.V.) as well as the International application WO 2015/173325 which was based on these provisional applications and which was published on Nov. 19, 2015.

Accordingly, in the method of the present invention, the polypeptide may further comprise a C-terminal extension (X)n, in which n is 1 to 5, such as 1, 2, 3, 4 or 5, and in which X is a naturally occurring amino acid, preferably no cysteine.

In a preferred aspect, the polypeptide of the invention, expressed in the method of the invention, comprises or essentially consists of SEQ ID NO: 55. In a particular aspect, such polypeptide consists of SEQ ID NO: 55.

In the polypeptides described above, the one or more immunoglobulin single variable domains and the one or more groups, residues, moieties or binding units may be linked directly to each other and/or via one or more suitable linkers or spacers. For example, when the one or more groups, residues, moieties or binding units are amino acids, the linkers may also be an amino acid, so that the resulting polypeptide is a fusion protein or fusion polypeptide.

In one specific aspect of the invention, a polypeptide of the invention is prepared that has an increased half-life, compared to the corresponding immunoglobulin single variable domain. Polypeptides of the invention that comprise such half-life extending moieties for example include, without limitation, polypeptides in which the immunoglobulin single variable domain is suitably linked to one or more serum proteins or fragments thereof (such as (human) serum albumin or suitable fragments thereof) or to one or more binding units that can bind to serum proteins (such as, for example, domain antibodies, amino acids that are suitable for use as a domain antibody, single domain antibodies, amino acids that are suitable for use as a single domain antibody, "dAb"'s, amino acids that are suitable for use as a dAb, or Nanobodies that can bind to serum proteins such as serum albumin (such as human serum albumin), serum immunoglobulins (such as IgG), or transferrin); polypeptides in which the immunoglobulin single variable domain is linked to an Fc portion (such as a human Fc) or a suitable part or fragment thereof; or polypeptides in which the one or more immunoglobulin single variable domain(s) are suitably linked to one or more small proteins or peptides that can bind to serum proteins (such as, without limitation, the proteins and peptides described in WO 91/01743, WO 01/45746 or WO 02/076489).

Generally, the polypeptides of the invention with increased half-life preferably have a half-life that is at least 1.5 times, preferably at least 2 times, such as at least 5 times, for example at least 10 times or more than 20 times, greater than the half-life of the corresponding immunoglobulin single variable domain or polypeptide of the invention per se.

In a preferred, but non-limiting aspect, such polypeptides of the invention have a serum half-life that is increased with more than 1 hour, preferably more than 2 hours, more preferably more than 6 hours, such as more than 12 hours, or even more than 24, 48 or 72 hours, compared to the corresponding immunoglobulin single variable domain or polypeptide of the invention per se.

In another preferred, but non-limiting aspect, such polypeptides of the invention exhibit a serum half-life in human of at least about 12 hours, preferably at least 24 hours, more preferably at least 48 hours, even more preferably at least 72 hours or more. For example, polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

The method of the present invention is especially suited for immunoglobulin single variable domains and/or polypeptides of the invention that are not easily expressible in *Pichia*, such as *P. pastoris*, or in very low yields, when expressed under expression conditions applicable for use with these hosts; and for which thus, upon expression of these immunoglobulin single variable domains or polypeptides of the invention in *Pichia*, such as *P. pastoris*, not sufficient amounts can be obtained. Accordingly, the method of the invention is especially suited for immunoglobulin single variable domains and/or polypeptides of the invention for which, upon expression in a *Pichia* host (such as *P. pastoris*) under standard *Pichia* expression conditions (as defined herein), a low yield is obtained. A "low yield" as used in the present invention means that the yield of the immunoglobulin single variable domain and/or polypeptide of the invention obtained is 0.5 g/L or lower, such as 0.4 g/L or lower, 0.3 g/L or lower, 0.2 g/L or lower, 0.1 g/L or lower, 0.05 g/L or lower, 0.01 g/L or lower, or even less [expressed as g (gram) immunoglobulin single variable domain or polypeptide of the invention per L (litre) medium].

The method of the invention is also especially suited for immunoglobulin single variable domains and polypeptides of the invention for which, upon expression in a *Pichia* host (such as *P. pastoris*) under standard *Pichia* expression conditions (as defined herein), the yield obtained shows an inverse correlation (as defined herein) with the copy number of the nucleic acid encoding said immunoglobulin single variable domain and/or polypeptide. A yield showing "an inverse correlation" means that the yield of said immunoglobulin single variable domain and/or polypeptide obtained is higher when said immunoglobulin single variable domain and/or polypeptide is expressed (under standard *Pichia* expression conditions as defined herein) in a *Pichia* host that has one copy of the nucleic acid encoding said immunoglobulin single variable domain and/or polypeptide than the yield of said immunoglobulin single variable domain and/or polypeptide obtained when said immunoglobulin single variable domain and/or polypeptide is expressed (under standard *Pichia* expression conditions as defined herein) in a *Pichia* host that has more than one copy of the nucleic acid encoding said immunoglobulin single variable domain and/or polypeptide.

Preferred polypeptides for use in the method of the invention include SEQ ID NO's: 49 to 54. This sequence also forms a separate aspect of the invention. Accordingly, the present invention also relates to a polypeptide with SEQ ID NO: 49, 50, 51, 52, 53, 54, 55 or 56.

Other specifically preferred polypeptides for use in the method of the invention comprise or essentially consist of an immunoglobulin single variable domain that essentially consists of 4 framework regions (FR1 to FR4, respectively) and 3 complementarity determining regions (CDR1 to CDR3, respectively), in which CDR1 is SEQ ID NO: 58, CDR2 is SEQ ID NO: 60 and CDR3 is SEQ ID NO: 62, such as e.g. immunoglobulin single variable domains with the amino acid sequence of SEQ ID NO's: 55 or 56.

Auxiliary Protein

The term "auxiliary protein" as used herein refers to proteins that assist other molecular structures and/or proteins in performing their biological function, but do not themselves occur in the structure of these other molecular structures and/or proteins when these other molecular structures and/or proteins are performing their normal biological functions. Auxiliary proteins may e.g. modify the biophysical, pharmacological and/or expression properties of the other molecular structure and/or protein. Without being limiting, auxiliary proteins may stabilize the other molecular structure and/or protein (e.g. through complex formation), they may modulate the activity of the other molecular structure and/or protein, they may increase the (surface) expression of the other molecular structure and/or protein, and/or they could assist in folding and/or assembly.

The auxiliary protein of which the expression is enhanced in the method of the invention, is a functional HAC1 protein. The HAC1 protein may originate from any species, but is preferably from yeast origin, most preferably a yeast from the Saccharomycetes, such as a yeast from the genus *Saccharomyces*, *Komagataella* or *Pichia* (*Hansenula*), such as *Saccharomyces cerevisiae* or *Pichia pastoris*. In a specific aspect, the functional HAC1 protein is "HAC1spliced" or "HAC1spliced protein" (both terms are used interchangeably herein). HAC1spliced is the HAC1 protein obtained following the splicing event on the HAC1 mRNA (removal of the intron) as described in Guerfal et al. 2010 (Microbial Cell Factories 9: 49). In a more specific aspect, the HAC1spliced protein is from *Pichia* origin. In a preferred aspect, the HAC1spliced protein has the sequence as described in Guerfal et al. 2010 (Microbial Cell Factories 9: 49; SEQ ID NO: 14).

In the method of the present invention, in addition to HAC1 protein, optionally expression of one or more additional auxiliary proteins selected from protein disulfide isomerase (PDI1; EC 5.3.4.1), Kar2p and Conserved ribosomal protein P0 (RPP0) is enhanced. These auxiliary proteins may originate from any species as long as the enhancement of their expression in a *Pichia* host provides for increased yield of the immunoglobulin single variable and/or polypeptide of the invention. In a preferred aspect, the auxiliary protein originates from a fungus, such as a yeast; preferably a yeast from the Saccharomycetes, such as a yeast from the genus *Saccharomyces*, *Komagataella* or *Pichia* (*Hansenula*), such as *Saccharomyces cerevisiae* or *Pichia pastoris*.

In a preferred aspect, the auxiliary protein is selected from the following:

*P. pastoris* HAC1spliced

```
                                          (SEQ ID NO: 14)
MPVDSSHKTASPLPPRKRAKTEEEKEQRRVERILRNRRAAHASREKKRRH

VEFLENHVVDLESALQESAKATNKLKEIQDIIVSRLEALGGTVSDLDLTV

PEVDFPKSSDLEPMSDLSTSSKSEKASTSTRRSLTEDLDEDDVAEYDDEE

EDEELPRKMKVLNDKNKSTSIKQEKLNELPSPLSSDFSDVDEEKSTLTHL

KLQQQQQQPVDNYVSTPLSLPEDSVDFINPGNLKIESDENFLLSSNTLQI

KHENDTDYITTAPSGSINDFFNSYDISESNRLHHPAAPFTANAFDLNDFV

FFQE;
``` and optionally one or more of:

*P. pastoris* protein disulfide isomerase (PDI1):

```
                                          (SEQ ID NO: 5)
MQFNWNIKTVASILSALTLAQASDQEAIAPEDSHVVKLTEATFESFITS

NPHVLAEFFAPWCGHCKKLGPELVSAAEILKDNEQVKIAQIDCTEEKEL

CQGYEIKGYPTLKVFHGEVEVPSDYQGQRQSQSIVSYMLKQSLPPVSEI

NATKDLDDTIAEAKEPVIVQVLPEDASNLESNTTFYGVAGTLREKFTFV

STKSTDYAKKYTSDSTPAYLLVRPGEEPSVYSGEELDETHLVHWIDIES

KPLFGDIDGSTFKSYAEANIPLAYYFYENEEQRAAAADIIKPFAKEQRG

KINFVGLDAVKFGKHAKNLNMDEEKLPLFVIHDLVSNKKFGVPQDQELT

NKDVTELIEKFIAGEAEPIVKSEPIPEIQEEKVFKLVGKAHDEVVFDES

KDVLVKYYAPWCGHCKRMAPAYEELATLYANDEDASSKVVIAKLDHTLN

DVDNVDIQGYPTLILYPAGDKSNPQLYDGSRDLESLAEFVKERGTHKVD

ALALRPVEEEKEAEEEAESEADAHDEL;
```

*P. pastoris* Kar2p:

```
                                          (SEQ ID NO: 4)
MLSLKPSWLTLAALMYAMLLVVVPFAKPVRADDVESYGTVIGIDLGTTY

SCVGVMKSGRVEILANDQGNRITPSYVSFTEDERLVGDAAKNLAASNPK

NTIFDIKRLIGMKYDAPEVQRDLKRLPYTVKSKNGQPVVSVEYKGEEKS

FTPEEISAMVLGKMKLIAEDYLGKKVTHAVVTVPAYFNDAQRQATKDAG

LIAGLTVLRIVNEPTAAALAYGLDKTGEERQIIVYDLGGGTFDVSLLSI

EGGAFEVLATAGDTHLGGEDFDYRVVRHFVKIFKKKHNIDISNNDKALG

KLKREVEKAKRTLSSQMTTRIEIDSFVDGIDFSEQLSRAKFEEINIELF

KKTLKPVEQVLKDAGVKKSEIDDIVLVGGSTRIPKVQQLLEDYFDGKKA

SKGINPDEAVAYGAAVQAGVLSGEEGVDDIVLLDVNPLTLGIETTGGVM

TTLINRNTAIPTKKSQIFSTAADNQPTVLIQVYEGERALAKDNNLLGKF

ELTGIPPAPRGTPQVEVTFVLDANGILKVSATDKGTGKSESITINNDRG

RLSKEEVDRMVEEAEKYAAEDAALREKIEARNALENYAHSLRNQVTDDS

ETGLGSKLDEDDKETLTDAIKDTLEFLEDNFDTATKEELDEQREKLSKI

AYPITSKLYGAPEGGTPPGGQGFDDDDGDFDYDYDYDHDEL;
``` and

*P. pastoris* 60S acidic ribosomal protein P0 (RPP0):

```
                                          (SEQ ID NO: 6)
MGGINEKKAEYFNKLRELLESYKSIFIVGVDNVSSQQMHEVRQTLRGKA

VILMGKNTMVRKALRDFVEELPVFEKLLPFVRGNIGFVFTNEDLKTIRD

VIIENRVAAPARPGAIAPLDVFIPAGNTGMEPGKTSFFQALGVPTKISR

GTIEITSDVKVVEKDSRVGPSEAQLLNMLNISPFTYGLTVVQVFDDGQV

FPANILDITDDELLSHFTSAISTIAQISLAAGYPTLPSVGHSVVNHYKN

VLAVSIATDYSFEGSEAIKDRLANPEAYAAAAPAAGEASAGAEETAAAA

EEEDEESEDDDMGFGLFD.
```

Method of the Invention

The invention relates to a method for expressing and/or producing immunoglobulin single variable domains and/or polypeptides comprising the same in a *Pichia* host. In the method of the invention the expression of HAC1spliced protein in the *Pichia* host is enhanced. The method of the invention comprises the following steps:

a) expressing, in a *Pichia* host, a nucleic acid encoding an immunoglobulin single variable domain and/or a polypeptide of the invention; and
b) enhancing, in said *Pichia* host, the expression of a nucleic acid(s) encoding HAC1spliced protein;

optionally followed by:

c) isolating and/or purifying the immunoglobulin single variable domain and/or polypeptide of the invention thus obtained.

As such, the method of the present invention comprises the steps of:

a) cultivating a *Pichia* host under conditions that are such that said *Pichia* host will multiply;
b) maintaining the *Pichia* host under conditions that are such that said *Pichia* host expresses and/or produces the immunoglobulin single variable domain and/or polypeptide of the invention; and
c) enhancing, in said *Pichia* host, the expression of a nucleic acid encoding HAC1spliced protein;

optionally followed by:

d) isolating and/or purifying from the medium the immunoglobulin single variable domain and/or polypeptide of the invention thus obtained.

To produce/obtain expression of the immunoglobulin single variable domains and/or polypeptide of the invention, the transformed *Pichia* host may generally be kept, maintained and/or cultured under conditions that are such that the (desired) immunoglobulin single variable domain and/or polypeptide of the invention is expressed/produced. Suitable conditions will be clear to the skilled person and will usually depend upon the *Pichia* host strain used, as well as on the regulatory elements that control the expression of the (relevant) nucleotide sequence of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequence(s) of the invention are under the control of an inducible promoter); all of which may be selected by the skilled person. Again, under such conditions, the immunoglobulin single variable domain and/or polypeptide of the invention may be expressed in a constitutive manner, in a transient manner, or only when suitably induced.

Culturing conditions for the recombinant production of heterologous proteins in *Pichia* are e.g. described by Higgins and Cregg 1998 (Eds, Methods in Molecular Biology, *Pichia* protocols, Volume 103, 2$^{nd}$ Ed., Humana Press) and by Invitrogen™ (Invitrogen™ *Pichia* Expression Kit; For Expression of Recombinant Proteins in *Pichia pastoris*; Catalog no. K1710-01). Production of immunoglobulin single variable domains in *P. pastoris* has been extensively described in WO 94/25591, WO 2010/125187, WO 2012/056000 and WO 2012/152823. The contents of these references are explicitly referred to in the connection with general culturing techniques and methods, including suitable media and conditions. The contents of these documents are incorporated by reference. The present invention also relates to specific conditions described in the art, for example the general culturing methods described in WO 94/25591, Gasser et al. 2006 (Biotechnol. Bioeng. 94: 535); Gasser et al. 2007 (Appl. Environ. Microbiol. 73: 6499), or Damasceno et al. 2007 (Microbiol. Biotechnol. 74: 381).

*Pichia*, in particular *P. pastoris*, is typically cultured at 30° C. in fed-batch fermentations using glycerol as carbon source. Such a medium generally comprises a buffering agent, glycerol, trace elements and ammonium hydroxide. Examples of buffering agents include (without being limiting) $H_3PO_4$, $CaSO_4 \cdot 2H_2O$, $K_2SO_4$, $MgSO_4 \cdot 7H_2O$, and KOH. A common growth medium (e.g. basal salt medium) consists of (per L) 26.7 mL 85% $H_3PO_4$, 0.93 g $CaSO_4 \cdot 2H_2O$, 18.2 g $K_2SO_4$, 14.9 g $MgSO_4 \cdot 7H_2O$, 4.13 g KOH, 40 g glycerol, 2 mL trace elements [composed of 6 g/L cupric sulfate·$5H_2O$; 0.8 g/L potassium iodide; 3 g/L manganese sulfate.H2O; 0.2 g/L sodium molybdate·$2H_2O$; 0.2 g/L boric acid; 0.5 g/L copper sulfate; 20 g/L zinc chloride; 65 g/L ferrous sulfate·$7H_2O$; 0.2 g/L biotin and 5 mL concentrated sulfuric acid]. Ammonium hydroxide ($NH_4OH$) is used for pH control (e.g. pH 5) and as a nitrogen source. During the fed-batch phase, glycerol (e.g. 50% v/v) is fed at a feed rate of e.g. 15 mL/L/h for several hours. The AOX1 promoter is used to drive expression of the gene of interest encoding the desired immunoglobulin single variable domain and/or polypeptide of the invention. Expression of the immunoglobulin single variable domain and/or polypeptide of the invention is carried out at 30° C. with a methanol feed rate of 4-10 mL/L/h (such as e.g. 4 mL/L/h). These conditions are also referred to herein as "standard *Pichia* expression conditions".

Expression of an auxiliary protein can be enhanced in the *Pichia* host by commonly known means, including e.g. the use of suitable control sequences, e.g. a strong promoter, and/or increasing the gene dose, e.g. by increasing the copy number of the respective gene. The copy number can be increased e.g. by introducing genetic constructs (plasmids or vectors) suitable for expression of the auxiliary protein. The additional presence of a plasmid or vector will increase the overall copy number. Moreover, genetic constructs that can multiply independently of the *Pichia* host genome and are present in multiple copies in the *Pichia* host can be used. For example, multi copy plasmids or vectors may be present in copy numbers between 5 and 50 in the *Pichia* host cell.

In addition to plasmid or vector transformation of the *Pichia* host, chromosomal transformation of the *Pichia* host is also encompassed by the present invention. A strong (inducible) promoter (instead of the native promoter of a native auxiliary protein) may be introduced on the chromosome of the host; or another copy of an auxiliary protein gene sequence under control of another (strong) promoter may be introduced into the chromosome. The skilled person will know a multitude of possibilities of enhancing the expression of the auxiliary protein, all of which are encompassed by the present invention.

The auxiliary protein(s) and the immunoglobulin single variable domain and/or polypeptide of the invention can be expressed from the same or different nucleic acids. Co-expression of the two or more proteins can be accomplished by expression of the two or more proteins on the same genetic construct (plasmid or vector or integrated into the chromosome of the host); or by expression of the two or more proteins on different genetic constructs (plasmids or vectors or integrated into the chromosome of the host).

When expressed on the same genetic construct, the nucleic acids encoding said two or more proteins are preferably located next to each other. The transcription of the nucleic acid encoding said two or more proteins may be controlled by one promoter (located in front of both genes); or each nucleic acid encoding one of the two or more proteins may be controlled by a separate promoter, which may be the same or different promoters.

When expressed from different genetic constructs, the transcription of the nucleic acid encoding the polypeptide of the invention and the transcription of the nucleic acid encoding one or more auxiliary protein(s) may be controlled by two separate promoters which may be the same or different.

The promoter can be a constitutive promoter or an inducible promoter. In a preferred aspect, the promoter is an inducible promoter.

The number of auxiliary proteins of which expression is enhanced in the method of the present invention may be one (HAC1spliced protein), or may be more than one such as e.g. two, three, four, five or more. In a preferred aspect, the number of auxiliary proteins of which expression is enhanced in the method of the present invention is one (HAC1spliced protein).

In another preferred aspect, the number of auxiliary proteins of which expression is enhanced in the method of the present invention is two, three, four or even more. In this preferred aspect the expression of HAC1spliced protein is enhanced and additionally the expression of one or more additional auxiliary proteins is enhanced. The additional auxiliary protein can be any auxiliary protein available and/or known in the art. Preferably the additional auxiliary protein is selected from any of PDI1, Kar2p and RPPO.

Accordingly, also encompassed in the method of the present invention is the expression and/or production of immunoglobulin single variable domains and/or polypeptides comprising the same in a *Pichia* host wherein the expression of HAC1spliced protein and one or more additional auxiliary proteins selected from PDI1, Kar2p and RPP0 is enhanced. Accordingly, the present invention also relates to a method comprising the following steps:
a) expressing, in a *Pichia* host, a nucleotide sequence encoding an immunoglobulin single variable domain and/or a polypeptide of the invention;
b) enhancing, in said *Pichia* host, the expression of a nucleic acid encoding HAC1spliced protein and the expression of one, two, three (or more) nucleic acids encoding an auxiliary protein selected from PDI1, Kar2p and RPP0; optionally followed by:
c) isolating and/or purifying the immunoglobulin single variable domain and/or polypeptide of the invention thus obtained.

In a specific aspect, the method of the present invention comprises the steps of:
a) cultivating a *Pichia* host under conditions that are such that said *Pichia* host will multiply;
b) maintaining the *Pichia* host under conditions that are such that said *Pichia* host expresses and/or produces the immunoglobulin single variable domain and/or polypeptide of the invention; and
c) enhancing, in said *Pichia* host, the expression of a nucleic acid encoding HAC1spliced protein and the expression of one, two, three (or more) nucleic acids encoding an auxiliary protein selected from PDI1, Kar2p and RPP0; optionally followed by:
d) isolating and/or purifying from the medium the immunoglobulin single variable domain and/or polypeptide of the invention thus obtained.

Accordingly, in this particular aspect of the method of the present invention, expression of following combinations of auxiliary protein(s) can be enhanced:
PDI1 and HAC1spliced;
Kar2p and HAC1spliced;
RPP0 and HAC1spliced;
PDI1, Kar2p and HAC1spliced;
PDI1, RPP0 and HAC1spliced;
Kar2p, RPP0 and HAC1spliced; and
PDI1, Kar2p, RPP0 and HAC1spliced.

When the number of auxiliary proteins is two or more, the auxiliary proteins can be expressed by the action of the same genetic construct, such as expression of the two or more auxiliary proteins on one plasmid or vector; or by expression of the two or more auxiliary proteins on different plasmids or vectors. In addition to plasmid or vector transformation of the *Pichia* host, chromosomal transformation of the *Pichia* host also is encompassed by the present invention. A strong (inducible) promoter (instead of the native promoter of a native auxiliary protein) may be introduced on the chromosome of the host; another copy of an auxiliary protein gene sequence under control of another (strong) promoter may be introduced into the chromosome. When expressed on the same genetic construct, the two or more auxiliary proteins may be controlled by the same promoter or by a different promoter. When expressed from different genetic constructs, the two or more auxiliary proteins may be controlled by two separate promoters which may be the same or different. The promoter may be a constitutive or an inducible promoter.

By use of the above methods, the present inventors were able to increase the unexpectedly low yield sometimes observed with immunoglobulin single variable domains and/or polypeptides comprising the same. Low yields were particularly observed for immunoglobulin single variable domains (and/or polypeptides comprising the same) that comprise two disulfide bridges, immunoglobulin single variable domains (and/or polypeptides comprising the same) that are VHH1 type immunoglobulin single variable domains, and/or immunoglobulin single variable domains (and/or polypeptides comprising the same) for which, upon expression in a *Pichia* host under standard *Pichia* expression conditions, the yield obtained shows an inverse correlation with the copy number of the nucleic acid encoding said immunoglobulin single variable domain (and/or polypeptide comprising the same).

Accordingly, the present invention also provides a method for increasing the (expression and/or production) yield of immunoglobulin single variable domains and/or polypeptides comprising the same, comprising the following steps:
a) expressing, in a *Pichia* host, a nucleic acid encoding an immunoglobulin single variable domain and/or a polypeptide of the invention; and
b) enhancing, in said *Pichia* host, the expression of a nucleic acid encoding HAC1spliced protein; optionally followed by:
c) isolating and/or purifying the immunoglobulin single variable domain and/or polypeptide of the invention thus obtained.

As such, the method for increasing the (expression and/or production) yield of immunoglobulin single variable domains and/or polypeptides comprises the steps of:
a) cultivating a *Pichia* host under conditions that are such that said *Pichia* host will multiply;
b) maintaining the *Pichia* host under conditions that are such that said *Pichia* host expresses and/or produces the immunoglobulin single variable domain and/or polypeptide of the invention; and
c) enhancing, in said *Pichia* host, the expression of a nucleic acid encoding HAC1spliced protein; optionally followed by:
d) isolating and/or purifying from the medium the immunoglobulin single variable domain and/or polypeptide of the invention thus obtained.

In a preferred aspect, the method of the invention provides a yield of immunoglobulin single variable domain and/or polypeptide of the invention which is 2 or more (preferably 3 or 4 or more, more preferably 5, 7.5, 10, 15, 20, 25, 30, 40, 50 or even more) times the yield of the same immunoglobulin single variable domains and/or polypeptide of the invention obtained in a method wherein the expression of HAC1spliced protein is not enhanced.

Accordingly, in a preferred aspect, the present invention also provides a method for increasing the (expression and/or production) yield of immunoglobulin single variable domains and/or polypeptides comprising the same, comprising the following steps:
a) expressing, in a *Pichia* host, a nucleic acid encoding an immunoglobulin single variable domain and/or a polypeptide of the invention; and
b) enhancing, in said *Pichia* host, the expression of a nucleic acid encoding HAC1spliced protein;
optionally followed by:
c) isolating and/or purifying the immunoglobulin single variable domain and/or polypeptide of the invention thus obtained,
wherein said method provides a yield of immunoglobulin single variable domain and/or polypeptide of the invention which is 2 or more (preferably 3 or 4 or more, more preferably 5, 7.5, 10, 15, 20, 25, 30, 40, 50 or even more) times the yield of the same immunoglobulin single variable domains and/or polypeptide of the invention obtained in a method wherein the expression of HAC1spliced protein is not enhanced.

As such, the method for increasing the (expression and/or production) yield of immunoglobulin single variable domains and/or polypeptides comprises the steps of:
a) cultivating a *Pichia* host under conditions that are such that said *Pichia* host will multiply;
b) maintaining the *Pichia* host under conditions that are such that said *Pichia* host expresses and/or produces the immunoglobulin single variable domain and/or polypeptide of the invention; and
c) enhancing, in said *Pichia* host, the expression of a nucleic acid encoding HAC1spliced protein;
optionally followed by:
d) isolating and/or purifying from the medium the immunoglobulin single variable domain and/or polypeptide of the invention thus obtained,
wherein said method provides a yield of immunoglobulin single variable domain and/or polypeptide of the invention which is 2 or more (preferably 3 or 4 or more, more preferably 5, 7.5, 10, 15, 20, 25, 30, 40, 50 or even more) times the yield of the same immunoglobulin single variable domains and/or polypeptide of the invention obtained in a method wherein the expression of HAC1spliced protein is not enhanced.

In another preferred aspect, the method of the invention provides a yield of immunoglobulin single variable domain and/or polypeptide of the invention which is 1 g/L or more, more preferably of 1.5 g/L or more, 2 g/L or more, or even 2.5 g/L or more.

Accordingly, in another preferred aspect, the present invention also provides a method for increasing the (expression and/or production) yield of immunoglobulin single variable domains and/or polypeptides comprising the same, comprising the following steps:
a) expressing, in a *Pichia* host, a nucleic acid encoding an immunoglobulin single variable domain and/or a polypeptide of the invention; and
b) enhancing, in said *Pichia* host, the expression of a nucleic acid encoding HAC1spliced protein;
optionally followed by:
c) isolating and/or purifying the immunoglobulin single variable domain and/or polypeptide of the invention thus obtained,
wherein said method provides a yield of immunoglobulin single variable domain and/or polypeptide of the invention which is 1 g/L or more, more preferably of 1.5 g/L or more, 2 g/L or more, or even 2.5 g/L or more.

As such, the method for increasing the (expression and/or production) yield of immunoglobulin single variable domains and/or polypeptides comprises the steps of:
a) cultivating a *Pichia* host under conditions that are such that said *Pichia* host will multiply;
b) maintaining the *Pichia* host under conditions that are such that said *Pichia* host expresses and/or produces the immunoglobulin single variable domain and/or polypeptide of the invention; and
c) enhancing, in said *Pichia* host, the expression of a nucleic acid encoding HAC1spliced protein;
optionally followed by:
d) isolating and/or purifying from the medium the immunoglobulin single variable domain and/or polypeptide of the invention thus obtained,
wherein said method provides a yield of immunoglobulin single variable domain and/or polypeptide of the invention which is 1 g/L or more, more preferably of 1.5 g/L or more, 2 g/L or more, or even 2.5 g/L or more.

The immunoglobulin single variable domains and/or the polypeptides of the invention are produced extracellular, and are isolated from the medium in which the *Pichia* host cell is cultivated.

Normally, but not necessarily, the immunoglobulin single variable domains and/or polypeptides of the invention will have at least a transport signal which directs the immunoglobulin single variable domains and/or polypeptides of the invention to the periplasm. In the present invention, the *Pichia* host can be removed from the culture medium by routine means. For example, the *Pichia* host can be removed by centrifugation or filtration. The solution obtained by removal of the *Pichia* host from the culture medium is also referred to as culture supernatant, or clarified culture supernatant.

It will also be clear to the skilled person that the immunoglobulin single variable domains and/or polypeptides of the invention may (first) be generated in an immature form (as mentioned above), which may then be subjected to post-translational modification, depending on the *Pichia* host used. Also, the immunoglobulin single variable domains and/or polypeptides of the invention may be glycosylated, again depending on the *Pichia* host cell used.

The immunoglobulin single variable domains and/or the polypeptides of the invention can subsequently be isolated from the *Pichia* host and/or from the medium in which said *Pichia* host was cultivated by standard methods. Standard methods include, but are not limited to chromatographic methods, including size exclusion chromatography, hydrophobic chromatography, ion exchange chromatography, and affinity chromatography. These methods can be performed alone or in combination with other purification methods, e.g. differential precipitation techniques, gel electrophoresis, affinity techniques (e.g. using a specific, cleavable amino acid sequence fused with the immunoglobulin single variable domains and/or polypeptides of the invention) and/or preparative immunological techniques (i.e. using antibodies against the immunoglobulin single variable domains and/or polypeptides of the invention to be isolated). The skilled person can devise suitable combinations of purification methods for immunoglobulin single variable domains on the basis of common general knowledge. For specific examples the art cited herein is referred to.

Immunoglobulin single variable domains and/or polypeptides comprising the same can be purified from culture supernatant by a combination of affinity chromatography on Protein A, ion exchange chromatography and size exclusion chromatography. Reference to any "step of purification", includes, but is not limited to these particular methods. More specifically, immunoglobulin single variable domains and/or polypeptides comprising the same can be purified from culture supernatant using a process wherein the clarified supernatant (obtained by centrifugation) is captured on a Protein A resin; followed by a SOURCE 15S (GE Healthcare) cation exchange chromatography step and a Superdex 75 (GE Healthcare) SEC step.

After removal of the *Pichia* host, the immunoglobulin single variable domain and/or polypeptide of the invention may be present in a wide range of suitable buffers. Examples include, but are not limited to PBS, Tris-HCl, histidine or phosphate buffer. The immunoglobulin single variable domains and/or polypeptides of the invention may also be present in physiological saline.

Generally, for pharmaceutical use, the immunoglobulin single variable domains and/or polypeptides of the invention may be formulated as a pharmaceutical preparation or compositions comprising at least one immunoglobulin single variable domain and/or polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person.

Nucleic Acid and Genetic Construct of the Invention

The present invention also relates to nucleic acids encoding an immunoglobulin single variable domain and/or a polypeptide of the invention and HAC1spliced. These nucleic acids are also referred to herein as "nucleic acid(s) of the invention".

The nucleic acid of the invention may be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as suitable promoter(s), enhancer(s), terminator(s), etc.) and the further elements of genetic constructs referred to herein. Such genetic constructs comprising at least one nucleic acid of the invention will also be referred to herein as "genetic construct(s) of the invention". As such, a genetic construct of the invention at least encodes an immunoglobulin single variable domain and/or polypeptide of the invention and HAC1spliced.

The number of auxiliary proteins encoded by the nucleic acid(s) and genetic construct(s) of the invention may be one (i.e. HAC1spliced protein) or may be more than one, such as two, three, four, five, or more. In a preferred aspect, the number of auxiliary proteins encoded by the nucleic acid and genetic construct of the invention is one (i.e. HAC1spliced protein). In another preferred aspect, the number of auxiliary proteins encoded by the nucleic acid(s) and genetic construct(s) of the invention is two, or more.

Accordingly, the present invention also encompasses nucleic acids or genetic constructs encoding an immunoglobulin single variable domain and/or a polypeptide of the invention and two or more auxiliary proteins (including HAC1spliced protein).

As discussed above, the immunoglobulin single variable domain and/or a polypeptide of the invention and the auxiliary protein(s) can be co-expressed from one single nucleic acid and/or genetic construct; or from different (separate) nucleic acids and/or genetic constructs (possibly including expression from the chromosome of the host). All these nucleic acids and/or genetic constructs encoding the immunoglobulin single variable domain and/or a polypeptide of the invention and/or encoding the auxiliary protein(s) (as one construct or as separate constructs) are encompassed within the terms "nucleic acid(s) of the invention" and "genetic construct(s) of the invention".

A nucleic acid of the invention can be in the form of single or double stranded DNA or RNA, and is preferably in the form of double stranded DNA. For example, the nucleic acid of the invention may be genomic DNA, cDNA or synthetic DNA (such as DNA with a codon usage that has been specifically adapted for expression in the *Pichia* host cell).

According to one embodiment of the invention, the nucleic acid of the invention is in essentially isolated from, as defined herein. The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the immunoglobulin single variable domain and/or polypeptide of the invention to be expressed and the auxiliary protein(s) used for co-expression. Also, as will be clear to the skilled person, to prepare a nucleic acid of the invention, also several nucleotide sequences, such as at least one nucleotide sequence encoding an immunoglobulin single variable domain and/or polypeptide of the invention and at least one nucleotide sequence encoding the auxiliary protein can be linked together in a suitable manner.

Techniques for generating the nucleic acids of the invention will be clear to the skilled person and may for instance include, but are not limited to, automated DNA synthesis, site-directed mutagenesis, combining two or more naturally occurring and/or synthetic sequences (or two or more parts thereof), introduction of mutations that lead to the expression of a truncated expression product, introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned herein, as well as the Examples below.

The genetic constructs of the invention may be DNA or RNA, and are preferably double-stranded DNA. The genetic constructs of the invention may also be in a form suitable for transformation of the *Pichia* host, in a form suitable for integration into the genomic DNA of the *Pichia* host cell or in a form suitable for independent replication, maintenance and/or inheritance in the *Pichia* host. For instance, the genetic constructs of the invention may be in the form of a vector, such as for example a plasmid, YAC, a viral vector or transposon. In particular, the vector may be an expression vector, i.e. a vector that can provide for expression in the *Pichia* host.

In a preferred but non-limiting embodiment, a genetic construct of the invention comprises:
a) at least one nucleic acid of the invention; operably connected to
b) one or more regulatory elements, such as a promoter and optionally a suitable terminator;
and optionally also
c) one or more further elements of genetic constructs known per se;
in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used, the *Pichia* host strain, the manner in which the nucleotide sequences of the invention of interest are to be expressed (e.g. via constitutive, transient or inducible expression), and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required. In one aspect of the invention, the nucleotide sequence encoding the immunoglobulin single variable and/or polypeptide of the invention is operably linked to the nucleotide sequence encoding the auxiliary protein(s). They may be under control of the same promoter, or they may each be under control of a separate (same or different) promoter.

Methods of designing, creating or obtaining nucleic acid sequences for expression, of constructing appropriate vectors, inserting nucleic acid sequences into vectors, choosing appropriate *Pichia* host strains, introducing vectors into the *Pichia* host strain, causing or allowing expression of polypeptides or proteins, isolating nucleic acids from *Pichia* host strains or identifying nucleic acid sequences and corresponding protein sequences are standard methods (Sambrook et al. 1989) which are well known to anyone of ordinary skill in the art. The skilled person can also devise suitable genetic constructs for expression of immunoglobulin single variable domains and/or polypeptides of the invention in the *Pichia* host on the basis of common general knowledge. The present invention also refers to genetic constructs described in the art, for example the plasmids, promoters and leader sequences described in WO 94/25591, Cereghino and Cregg 2000 (Curr. Opinion Biotechnol. 10: 422), Gasser et al. 2006 (Biotechnol. Bioeng. 94: 535), Gasser et al. 2007 (Appl. Environ. Microbiol. 73: 6499) or Damasceno et al. 2007 (Microbiol. Biotechnol. 74: 381).

Preferably, the regulatory and further elements of the genetic constructs of the invention are such that they are capable of providing their intended biological function in the *Pichia* host.

For instance, a promoter, enhancer or terminator should be "operable" in the *Pichia* host by which is meant that (for example) said promoter should be capable of initiating or otherwise controlling/regulating the transcription and/or the expression of a nucleotide sequence—e.g. a coding sequence—to which it is operably linked (as defined herein).

Some preferred, but non-limiting examples of suitable promoters, terminator and further elements include those that can be used for the expression in the *Pichia* host; and in particular those mentioned herein and/or those used in the Examples below.

Some particularly preferred promoters include, but are not limited to, promoters known per se for the expression in the *Pichia* host; and in particular those mentioned herein and/or those used in the Examples. The specific sequence of the promoter determines the strength of the promoter (a "strong promoter" leads to a high rate of transcription initiation). When the expression of a nucleic acid encoding an auxiliary protein is said to be controlled by a "strong promoter", it is meant that the expression of the nucleic acid encoding said auxiliary protein is controlled by a promoter which leads to higher rate of transcription initiation than the native promoter which controls transcription initiation of the native auxiliary protein. In addition to sequences that "promote" transcription, a promoter may include additional sequences known as operators that control the strength of the promoter. For example, a promoter may include a binding site for a protein that attracts or obstructs the RNA binding to the promoter. The presence or absence of this protein will affect the strength of the promoter. Such a promoter is known as a regulated promoter.

The *P. pastoris* alcohol oxidase I (AOX1) promoter is one of the strongest, most regulated promoters known. On the contrary, the *P. pastoris* second alcohol oxidase (AOX2) is controlled by a much weaker promoter. The *P. pastoris* glyceraldehyde-3-phosphate dehydrogenase (GAP) promoter provides a constitutively high level of expression on glucose, glycerol, and methanol media (Waterham et al. 1997, Gene 186: 37). The *P. pastoris* formaldehyde dehydrogenase (FLD1) promoter can be induced either by methanol or methylamine and its expression levels are comparable to those obtained with the AOX1 promoter in methanol (Shen et al. 1998, Gene 216: 93). The peroxin 8 (PEXB) promoter gives low expression on glucose and is induced modestly (about 10-fold) when cells are shifted to methanol (Johnson et al. 1999, Genetics 151: 1379).

Strong promoters in *H. polymorpha* include elements derived from the methanol oxidase (MOX), formate dehydrogenase (FMD), and dihydroxyacetone synthase (DHAS) gene (Song et al. 2006, Biotechnol. Lett. 25: 1999). The glyceraldehyde-3-phosphate dehydrogenase (GAP1) promoter (Sohn et al. 1999, Appl. Microbiol. Biotechnol. 51: 800) and PMA1 promoter (Cox et al. 2000, Yeast 16: 1191) in *H. polymorpha* are constitutive elements. The PMA1 promoter competes with the MOX promoter in terms of high expression levels.

The *P. methanolica* alcohol oxidase (AUG1) promoters, P(MOD1) and P(MOD2), are strong and tightly regulated by methanol (P(MOD1) and P(MOD2)) and glycerol (only P(MOD1)) (Nakagawa et al. 2006, Yeast 23: 15).

Strong promoters from *C. boidinii* include the alcohol oxidase (AOD1) promoter and the dihydroxy acetone synthase (DAS1) promoter (Yurimoto et al. 2000, Biochim. Biophys. Acta 1493: 56). Both DAS1 and formate dehydrogenase (FMD) promoters are available in *C. boidinii* (Sakai et al. 1995, Appl. Microbiol. Biotechnol. 42: 860; 1996, Biochim. Biophys. Acta 1308: 81) and *H. polymorpha* (Hollenberg and Gellissen 1997, Curr. Opin. Biotechnol. 8: 554).

A selection marker should be such that it allows—i.e. under appropriate selection conditions—*Pichia* host cells that have been (successfully) transformed with the nucleic acids of the invention to be distinguished from *Pichia* host cells that have not been (successfully) transformed. Some preferred, but non-limiting examples of such markers are genes that provide resistance against antibiotics (such as e.g. Zeocin, blasticidin, geneticin (G418), phleomycin, kanamycin or ampicillin), genes that provide for temperature resistance, or genes that allow the *Pichia* host to be maintained in the absence of certain factors, compounds and/or (food) components in the medium that are essential for survival of the non-transformed cells.

A leader sequence should be such that—in the *Pichia* host—it allows for the desired post-translational modifications and/or for secretion of the expression product from said cell. As such, the leader sequence may be any pro-, pre-, or prepro-sequence operable in the *Pichia* host. However, normally, but not necessarily, the immunoglobulin single variable domains and/or polypeptides of the invention will have at least a transport signal which directs the immunoglobulin single variable domain and/or protein of the invention to the periplasm. For example, leader sequences known per se for the expression and production of antibodies and antibody fragments (including but not limited to single domain antibodies and ScFv fragments) may be used in an essentially analogous manner.

Some preferred, but non-limiting secretory sequences include the *S. cerevisiae* derived α-mating factor signal sequence, the *P. pastoris* derived acid phosphatase (PHO1) signal sequence, *P. pastoris* derived phosphatase (pho1) leader sequence, the secretion signal of yeast invertase (Suc), the Human Serum Albumin signal peptide, the *S. occidentalis* derived GAM1 signal sequence, and *Carcinus maenas* derived hyperglycemic hormone (CHH) sequences, etc.

The skilled person may also envisage the use of predicted signal peptides derived from genome sequencing experiments. These predicted signal peptide sequences may originate from any species, but are preferably from yeast origin, most preferably from a yeast from the Saccharomycetes, such as a yeast from the genus *Saccharomyces, Komagataella* or *Pichia (Hanensula)*, such as *Saccharomyces cerevisiae* or *Pichia pastoris*. Some preferred, but non-limiting predicted signal peptides derived from *P. pastoris* are described in De Schutter et al. 2009 (Nature Biotech 27(6): 561-566). Further reference is made to WO 2012/152823 for the use of such predicted signal peptides for the production of immunoglobulin single variable domains.

Known or predicted secretory sequences may also be modified to improve the properties of produced immunoglobulin single variable domains and/or polypeptides of the invention. Such modifications may for example improve the purity of immunoglobulin single variable domains and/or polypeptides of the invention by improving processing efficiency. Modification of the α-mating factor signal sequence for improved processing efficiency is described for example in WO 2012/152823.

An expression marker or reporter gene should be such that—in the *Pichia* host—it allows for detection of the expression of (a gene or nucleotide sequence present on) the genetic construct. Such reporter genes may also be expressed as a protein fusion with the immunoglobulin single variable domain and/or polypeptide of the invention. Some preferred, but non-limiting examples include fluorescent proteins such as GFP and luciferase (LUC).

The genetic constructs of the invention may generally be provided by suitably linking the nucleic acids and/or nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleic acid or nucleotide sequence of the invention in a suitable (expression) vector known per se. Some preferred, but non-limiting examples of suitable expression vectors are those used in the Examples below, as well as those mentioned herein.

Some preferred, but non-limiting vectors for use in the genetic constructs of the invention include vectors for expression in yeast or other fungal cells such as pYES2 (Invitrogen), pUR3515 and pUR3501 (Sierkstra et al. 1991, Curr. Genet. 19: 81) and *Pichia* expression vectors, such as e.g. (without being limiting) the pPICZ vectors, pPIC3.5, pPIC3.5K, pPIC6a, pPIC9, pPIC9K, pHIL-D2, pHIL-S1 for *P. pastoris* expression, pMET, pMETalpha for *P. methanolica* expression provided by Invitrogen. For a non-exhaustive list of *Pichia* expression vectors reference is also made to Daly and Hearn 2004 (J. Mol. Recognition 18: 119), *Pichia* Protocols 2007 (Ed. Cregg, $2^{nd}$ Ed., Humana Press, NJ) and Gelissen 2000 (Appl. Microbiol. Biotechnol. 54: 741).

Also encompassed in the present invention are methods for the preparation of the nucleic acid and genetic construct of the invention, comprising the step of cloning the auxiliary protein gene(s) and/or the nucleotide sequence encoding the immunoglobulin single variable domain and/or a polypeptide of the invention in a suitable vector.

The nucleic acids of the invention and/or the genetic constructs of the invention may be used to transform a *Pichia* host, i.e. for expression and/or production of the immunoglobulin single variable domain and/or of a polypeptide of the invention. Suitable techniques for transforming a *Pichia* host will be clear to the skilled person. Reference is again made to the handbooks and patent applications mentioned above. For more detail on transformation procedures reference is made to Invitrogen's EasySelect™ *Pichia* Expression manual, to Wu and Letchworth 2004 (BioTechniques 36: 152), to *Pichia* Protocols 2007 (Ed. Cregg, $2^{nd}$ Ed., Humana Press, NJ) and to Faber 1994 (Curr. Genet. 25: 305). After transformation, a step for detecting and selecting those *Pichia* host cells that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

Accordingly, the invention further relates to the preparation of a *Pichia* host cell comprising the genetic constructs or nucleic acids of the invention. The skilled person can introduce the nucleic acids or genetic constructs of the invention into the *Pichia* host by routine measures, e.g. by transformation. The skilled person can then select suitable *Pichia* host cells comprising the nucleic acids or genetic construct, e.g. by monitoring the expression of the auxiliary protein on the nucleic acid and/or protein level. A strain with a satisfactory level of expression will be selected. A high expression of auxiliary protein is desirable, however, it should not be so high as to result in competition with expression of the immunoglobulin single variable domain and/or polypeptide of the invention. This can be determined by routine methods.

The transformed *Pichia* host cell (which may be in the form of a stable cell line) forms a further aspect of the present invention.

*Pichia* Host

Accordingly, the present invention also relates to a *Pichia* host comprising such genetic constructs or nucleic acids as described above. The terms "*Pichia* host" and "*Pichia* host cells" are used interchangeably and refer to the *Pichia* (*Hansenula* and *Hyphopichia* are obsolete synonyms) genus of yeasts in the family Saccharomycetaceae with spherical, elliptical or oblong acuminate cells. *Pichia* is a teleomorph, and forms during sexual reproduction hat-shaped, hemispherical or round ascospores. The anamorphs of some *Pichia* species are *Candida* species. The asexual reproduction is by multilateral budding.

The present invention relates to *Pichia* hosts without limitation, provided that they are suitable for the production of an immunoglobulin single variable domain and/or polypeptide comprising the same. For the purpose of the present invention, the term "*Pichia* host" also includes *Hansenula* and *Candida* species.

The *Pichia* host of the present invention will be capable of producing the immunoglobulin single variable domain and/or the polypeptide of the invention and the HAC1spliced protein, and optionally one or more additional auxiliary protein(s) such as e.g. protein disulfide isomerase (PDI1), Kar2p or Conserved ribosomal protein P0 (RPP0). It will typically be genetically modified such that it comprises one or more nucleic acids encoding the immunoglobulin single variable domain and/or polypeptide of the invention and that expression of HAC1spliced protein is enhanced. Non-limiting examples of genetic modifications comprise the transformation e.g. with a plasmid or vector, or the transduction with a viral vector. Some hosts can be genetically modified by fusion techniques. Genetic modifications include the introduction of separate nucleic acid molecules into a host, e.g. plasmids or vectors, as well as direct modifications of the genetic material of the host, e.g. by integration into a chromosome of the host, e.g. by homologous recombination. Oftentimes a combination of both will occur, e.g. a host is transformed with a plasmid, which, upon homologous recombination will (at least partly) integrate into the host chromosome. The skilled person knows suitable methods of genetic modification of the host to enable the host to produce immunoglobulin single variable domains and/or polypeptides of the invention.

Suitable *Pichia* hosts will be clear to the skilled person, and may for example be a yeast, including but not limited to *Pichia*, *Hansenula*, or *Candida*, such as methylotrophic yeasts including *Pichia pastoris, Pichia methanolica, Hansenula* polymorpha (*Pichia angusta*) and *Candida boidinii*. For a non-exhaustive list of *Pichia* strains reference is e.g. made to Gelissen 2000 (Appl. Microbiol. Biotechno. 54: 741). Without being limiting, *P. pastoris* strains are listed in Daly and Hearn 2004 (J. Mol. Recognition, 18: 119) and *Pichia* Protocols 2007 (Ed. Cregg, $2^{nd}$ Ed., Humana Press, NJ). Examples of *P. pastoris* strains include (without being limiting) X33, GS115, KM71, KM71H, SMD1163, SMD1165, SMD1168, SMD1168H, NRRL-Y 11430, GS200 provided by Invitrogen, described by Cereghino and Cregg 2004 (FEMS Microbiol. Rev. 24: 45), by Macauley-Patrick et al. 2005 (Yeast 22: 249) and/or Damasceno et al. 2007 (Appl. Microbiol. Biotechno. 74: 381).

Examples of *Hansenula* polymorpha strains include (without being limiting) A16 (Veale et al. 1992, Yeast 8: 361), GF16 (Faber 1994, Proc. Natl. Acad. Sci. USA 91: 12985), CBS4732 (CCY38-22-2; ATCC34438, NRRL-Y-5445), DL-1 (NRRL-Y-7560; ATCC26012), and strain NCYC495 (CBS1976; ATAA14754, NRLL-Y-1798).

Examples of *P. methanolica* strains include (without being limiting) PMAD11 and PMAD16 provided by Invitrogen. Strains of *P. methanoloica* (IAM12901 and IAM12481) and *C. boidinii* (IAM12875) are described by Nakagawa et al. 1996 (J. Fermentation Bioeng. 81: 498).

Reference is also made to the general background art cited hereinabove, as well as to for example WO 94/29457, Frenken et al. 1998 (Res. Immunol. 149: 589), van der Linden 2000 (J. Biotechnol. 80: 261), Joosten et al. 2003 (Microb. Cell Fact. 2: 1), and the further references cited herein.

For production on industrial scale, preferred heterologous hosts for the (industrial) production of immunoglobulin single variable domain-containing protein therapeutics include strains of *Pichia pastoris* that are suitable for large scale expression/production/fermentation, and in particular for large scale pharmaceutical expression/production/fermentation. Suitable examples of such strains will be clear to the skilled person. Such strains and production/expression systems are also made available by companies such as Avecia Biologics (Billingham, North East England, UK), BIOMEVA GmbH (Heidelberg, Germany), PharmedArtis GmbH (Aachen, Germany), Richter-Helm (Hamburg, Germany), and CMC Biologics (Copenhagen, Denmark).

The invention also includes further generations, progeny and/or offspring of the *Pichia* host cell of the invention, which may for instance be obtained by cell division.

Pharmaceutical Preparation

The present invention also relates to immunoglobulin single variable domains and/or polypeptides of the invention obtainable by the methods of the invention as described herein.

Accordingly, the present invention also relates to pharmaceutical preparations and other compositions comprising an immunoglobulin single variable domain and/or a polypeptide of the invention obtainable by the methods of the present invention. The present invention also relates to the medical use of the immunoglobulin single variable domain and/or polypeptide of the invention obtainable by the method of the present invention.

The skilled person can readily formulate pharmaceutically suitable formulations on the basis of common general knowledge. Moreover, the references specifically dealing with immunoglobulin single variable domains and/or Nanobodies, which are cited herein, are explicitly referred to. Without limitation, formulations for standard routes of application can be prepared, including formulations for nasal, oral, intravenous, subcutaneous, intramuscular, intraperitoneal, intravaginal, rectal application, topical application or application by inhalation.

Based on the present invention, the skilled person can also readily devise suitable methods of treatment characterized by the use of a therapeutically effective amount of the immunoglobulin single variable domain and/or polypeptide of the invention obtainable by the method of the invention.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

The experimental section describes the surprising observation of low yields upon expression of monovalent and multivalent immunoglobulin single variable domains in *Pichia pastoris*. We also observed that yield is further reduced when more than 1 copy of the expression cassette is present in the genome of *P. pastoris*. Also described is a method for increasing the expression yield of said immunoglobulin single variable domains by enhancing the expression of HAC1spliced.

Example 1: Identification of Auxiliary Proteins that Increase the Expression of Nanobodies in *Pichia* Pastoris 1.1 Construction of Expression Vectors Nanobody A, previously described in WO 2013/045707 as SEQ ID NO: 7, is a bivalent Nanobody consisting of two sequence optimized variable domains of a heavy-chain llama antibody. The N-terminal subunit in Nanobody A is a VHH1 type immunoglobulin single variable domain and is specific for binding c-Met, while the C-terminal subunit binds to human serum albumin (HSA). The subunits are fused head-to-tail with a 9G/S linker. The sequence of Nanobody A (SEQ ID NO: 49) is depicted in Table A-1. Nanobody A was previously shown to give very low yields (0.2 g/L or lower) upon fermentation in *P. pastoris*.

DNA fragments containing the coding information of Nanobody A were cloned into the multiple cloning site of a *Pichia* expression vector (derivative of pPIC6a, Invitrogen) that contains a Blasticidin™ resistance gene marker, such that the Nanobody sequence was downstream of and in frame with the aMF signal peptide sequence. To generate *Pichia* clones with more than 1 copy number of the expression cassette in the genome, a unique BglII site in the *Pichia* expression vector was used to introduce a second expression cassette of Nanobody A.

Coding sequences of the auxiliary proteins depicted in Table A-2 were cloned (using the restriction enzymes BstBI and NotI) into a *Pichia* expression vector (derivative of the pPICZa, Invitrogen) containing the Zeocin™ resistance gene marker. Auxiliary proteins containing a BstBI site in their coding sequence were cloned using the restriction enzymes AfeI and NotI. The Nanobody and auxiliary protein in the pPIC6a and the pPICZa vectors were both under the control of the AOX1 methanol inducible promoter.

Figure 1:
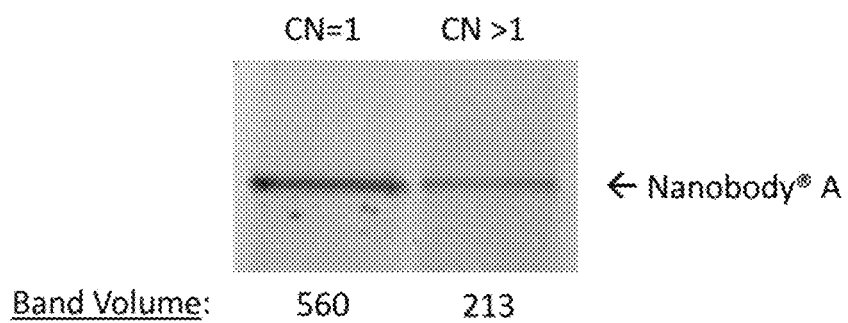
FIG. 1: Nanobody A was expressed in two different *Pichia* clones generated as described in Example 1.2. One *Pichia* clone contained 1 copy of the Nanobody A expression cassette in the genome. The second clone contained more than one copy of the Nanobody A expression cassette inserted in the genome. Equal volumes of supernatant were compared from the different clones on SDS-PAGE gel. Densitometry analysis for relative quantification of the bands corresponding to intact Nanobody product was performed. Quantification of band volumes was done using Imagequant software (GE Healthcare). An inverse correlation between copy number and yield was observed.

1.2 Transformation of the Nanobody Coding Sequences and Expression and Secretion of the Nanobody in *Pichia* Pastoris Transformation and expression studies of wild type *Pichia* X33 were performed by standard techniques and in accordance with the 'User manual for pPicZalphaA, B and C' (version D, 110801, Manual part no. 25-0148; Invitrogen) and Methods in Molecular Biology 2007 (Humana Press Inc.). Firstly, the *P. pastoris* strain was transformed with the appropriate expression vector with single or double expression cassette of Nanobody A. Transformants were grown on selective medium containing Blasticidin™. A number of individual colonies were characterized by qPCR to select clones having 1 copy of the expression vector integrated into the genome and clones having more than one copy of the expression cassette integrated into the genome. Expression and secretion into the medium of the Nanobody was verified (FIG. 1).

1.3 Transformation of the Auxiliary Protein Coding Sequences and Expression and Secretion of the Nanobody in *Pichia* Pastoris Once a suitable Nanobody expressing colony was identified, its inoculum was propagated and prepared as competent cells. These cells were then transformed with a library of expression vectors containing the 22 auxiliary proteins depicted in Table A-2. Transformants were grown on selective medium containing a different selection marker (Zeocin™) and this way, co-transformants containing both the Nanobody of interest and one or more of the auxiliary proteins of Table A-2 were obtained. Shake-flask expression was performed in 5 mL cultures in BMCM medium and induced by the addition of methanol as has been described in *Pichia* protocols (see e.g. Methods in molecular biology 2007, Humana Press Inc.).

Figure 2:
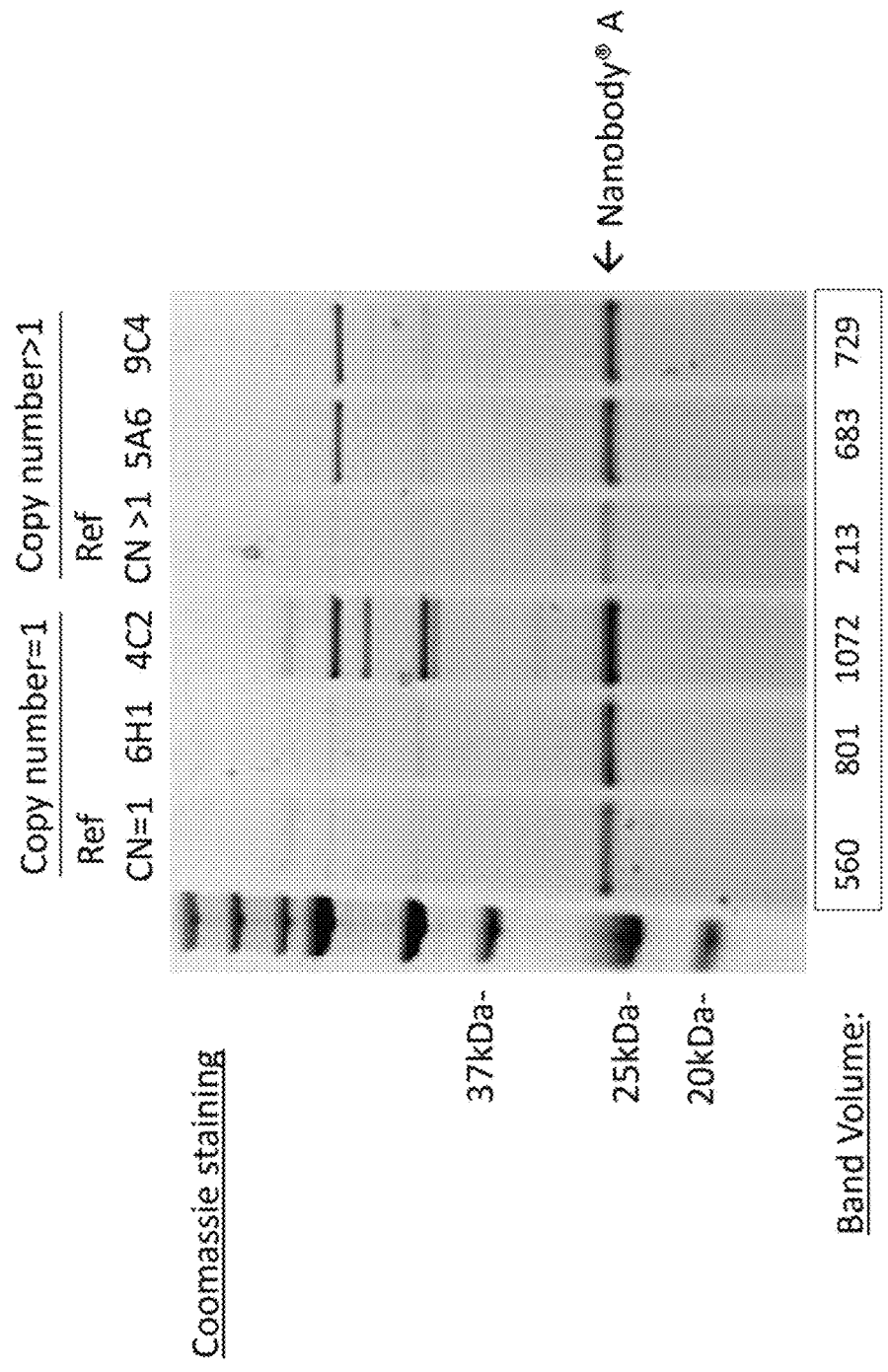
FIG. 2: Clones transformed with Nanobody A and the auxiliary protein library were tested for improved expression levels of Nanobody A. Equal volumes of supernatant were compared from the different clones on SDS-PAGE gel. Densitometry analysis for relative quantification of the bands corresponding to intact Nanobody product was performed. Quantification of band volumes was done using Imagequant software (GE Healthcare).

In each setup 1128 clones were screened for improved expression and compared to their corresponding reference clone which only contained 1 copy or more than one copy of the Nanobody expression cassette integrated into the genome but without the expression vector coding for one or more auxiliary proteins. For each setup we found 2 clones with yields significantly higher than their reference clones. Clones 6H1 and 4C2 had one copy of the Nanobody coding sequence integrated in the genome (copy number=1) and clones 5A6 and 9C4 had more than one copy of the Nanobody coding sequence integrated in the genome (copy number >1) (FIG. 2).

1.4 Identification of Auxiliary Proteins that have Positive Effect on the Expression Yield Identification of the auxiliary proteins that exert a positive effect on the expression yield of the Nanobody in *P. pastoris* was done by means of genomic DNA PCR using sequence-specific PCR primers. The list of primers used is shown in Table A-3.

The identified auxiliary proteins are shown in Table 1.

TABLE 1

The auxiliary proteins present in 4 clones (6H1, 4C2, 5A6, 9C4) that showed increased expression levels of Nanobody A were identified with specific PCR primers. The boxes marked with an "X" indicate the presence of a specific auxiliary protein in the corresponding clone. Auxiliary proteins that were present in both clones 4C2 and 6H1 or in both clones 5A6 and 9C4 are indicated with arrows.

|  | Copy number = 1 | | Copy number > 1 | |
|---|---|---|---|---|
|  | 4C2 | 6H1 | 5A6 | 9C4 |
| Fkpa |  | X |  | X |
| Kar2p | X |  | X | X |
| PDI1 | X | X |  |  |
| RPPO |  |  | X | X |
| BMH2 |  |  |  | X |
| Cct2 |  |  | X |  |
| Gim4 |  | X |  |  |

TABLE 1-continued

The auxiliary proteins present in 4 clones (6H1, 4C2, 5A6, 9C4) that showed increased expression levels of Nanobody A were identified with specific PCR primers. The boxes marked with an "X" indicate the presence of a specific auxiliary protein in the corresponding clone. Auxiliary proteins that were present in both clones 4C2 and 6H1 or in both clones 5A6 and 9C4 are indicated with arrows.

|              | Copy number = 1 | | Copy number > 1 | |
|---|---|---|---|---|
|              | 4C2 | 6H1 | 5A6 | 9C4 |
| Mdj1         |     |     | X   |     |
| → HAC1spliced | X  |     | X   | X   |
| Gas1         | X   |     |     | X   |
| Pma1         |     |     | X   |     |
| SSe1         |     |     |     | X   |
| Uso1         | X   |     |     |     |
| Ydj1         |     | X   |     |     |

1.5 Determination of the Expression Yield of the Different Clones

Expression yields of the Nanobody/auxiliary protein(s) co-transformants were compared to expression yields of controls (Nanobody transformants without enhancement of the expression of one or more auxiliary protein(s)) in expression experiments by quantification of the yields of expressed and secreted Nanobody in the medium. Standard fed batch fermentations conditions were used. Glycerol fed batches were performed and induction was initiated by the addition of methanol. The productions were performed at 2 L scale at pH6, 30° C. in complex medium with a methanol feed rate of 4 ml/L*h.

Samples were subjected to SDS-PAGE analysis. Relative quantifications of the proteins were done by means of Coomassie stained SDS-PAGE densitometry scan measurements (Table 2).

TABLE 2

Expression yields of Nanobody A with and without enhanced expression of auxiliary protein(s). Yield was estimated using SDS-PAGE/Coomassie staining and quantification of bandvolume was done using Imagequant software (GE Healthcare).

| Fermenter | Clone | Yield determined on gel (g/L) | Improvement over reference clone |
|---|---|---|---|
| R5/130529 | Reference clone (Copy number = 1) | 0.2 | — |
| R6/130529 | 4C2 | 1.5 | 7.5 times |
| R7/130529 | 6H1 | 0.9 | 4.5 times |
| R8/130529 | Reference clone (Copy number > 1) | 0.1 | — |
| R9/130529 | 5A6 | 2.2 | 22 times |
| R10/130529 | 9C4 | 2.7 | 27 times |

Clone 4C2 and 6H1 showed a remarkable increase in expression compared to their reference clone (1 copy number of the expression cassette integrated into the genome). This increase in expression was likely the result of the co-expression of PDI1 present in both clones. Similarly clones 5A6 and 9C4 showed a vast increase in yield compared to their reference clone. The auxiliary proteins that were both expressed in clones 5A6 and 9C4 are Kar2p, RPP0 and HAC1spliced. Most likely those auxiliary proteins are involved in improved expression of Nanobody A. Interestingly, the expression level of clone 4C2 is remarkably higher than clone 6H1 which is likely the result of the co-expression of Kar2p and HAC1spliced which are also present in the highest expressing clones 5A6 and 9C4. The clones that had the highest yield all co-expressed HAC1spliced (Tables 1 and 2).

Example 2: Evaluation of Nanobody a Yields when the Expression of Individual Auxiliary Proteins is Enhanced The individual auxiliary proteins PDI1, Kar2p, RPP0 and HAC1spliced were transformed into the Reference clone with more than 1 copy of the Nanobody expression cassette in the genome as described in Example 1.3. Transformants were grown on selective medium containing Zeocin™. Co-transformants containing both Nanobody A and a specific auxiliary protein were obtained. Shake-flask expression was performed in 5 mL cultures in BMCM medium and induced by the addition of methanol as has been described in *Pichia* protocols (see e.g. Methods in molecular biology 2007, Humana Press Inc.). Relative quantifications of the proteins were done by means of Coomassie stained SDS-PAGE densitometry scan measurements (FIG. 3). All clones co-expressing one of the auxiliary proteins showed a significant increase in yield of Nanobody A. Again, we observed that the clone containing HAC1spliced showed the largest improvement in yield.

Example 3: Evaluation of Nanobody B Yields when Expression of the Individually Auxiliary Proteins is Enhanced 3.1 Construction of Expression Vectors Nanobody B is a trivalent Nanobody consisting of three sequence optimized variable domains of a heavy-chain llama antibody. The subunits in Nanobody B are not of the VHH1 type immunoglobulin single variable domain and do not bind to human serum albumin (HSA). The subunits are fused head-to-tail with 35 G/S linkers. Nanobody B was previously shown to give very low yields (0.29 g/L or lower) upon fermentation in *P. pastoris*.

DNA fragments containing the coding information of Nanobody B were cloned into the multiple cloning site of a *Pichia* expression vector (derivative of the pPpT4_Alpha_S; Naatsaari et al. 2012, PLoS One 7: e39720) that contains a Zeocin™ resistance gene marker, such that the Nanobody sequence was downstream of and in frame with the aMF signal peptide sequence. Coding sequences of the auxiliary proteins HAC1spliced, Kar2p, PDI1 and RPP0 were cloned into *Pichia* expression vectors containing the Blasticidin™ resistance gene marker. The Nanobody and auxiliary protein were both under the control of the AOX1 methanol inducible promoter.

3.2 Transformations

The individual auxiliary proteins PDI1, Kar2p, RPP0 and HAC1spliced were transformed into the *Pichia pastoris* strain NRRL Y-11430 (ATCC number 76 273). Transformants were grown on selective medium containing Blasticidin™. Single clones were isolated and subsequently transformed with Nanobody B.

3.3 Determination of the Expression Yields of the Individual Clones

Expression analysis was done as described in Example 1.5. Relative quantifications of the proteins were done by means of Coomassie stained SDS-PAGE densitometry scan measurements (Table 3). Only the clone co-expressing HAC1spliced auxiliary protein showed a large increase in yield of Nanobody B, which again shows that enhanced expression of the auxiliary protein HAC1spliced most efficiently improves the yield.

TABLE 3

Expression yields of Nanobody B with and without enhanced expression of auxiliary protein. Yield was estimated using SDS-PAGE/Coomassie staining and quantification of bandvolume was done using Imagequant software (GE Healthcare).

|  | Strain | Yield determined on gel (g/L) | Improvement over reference clone |
|---|---|---|---|
| Nanobody B | Reference | 0.29 | — |
|  | HAC1spliced | 3.0 | 10.3 times |
|  | Kar2p | 0.8 | 2.8 times |
|  | PDI1 | 0.16 | — |
|  | RPP0 | 0.22 | — |

Example 4: Evaluation of the Yields of the Good Expressing Nanobody C when Expression of the Individual Auxiliary Proteins is Enhanced Nanobody C is a bivalent Nanobody consisting of two sequence optimized variable domains of a heavy-chain llama antibody. The subunits in Nanobody C are not of the VHH1 type immunoglobulin single variable domain. The C-terminal subunit binds to human serum albumin (HSA). The subunits are fused head-to-tail with a 35 G/S linker. The individual auxiliary proteins PDI1, Kar2p, RPP0 and HAC1spliced were cloned as described in Example 3 and transformed into the *Pichia pastoris* strain NRRL Y-11430. Transformants were grown on selective medium containing Blasticidin™. Single clones were isolated and subsequently transformed with Nanobody C. Expression analysis was done as described in Example 1.5. Relative quantifications of the proteins were done by means of Coomassie stained SDS-PAGE densitometry scan measurements (Table 4).

Only the clone co-expressing HAC1spliced auxiliary protein showed a significant increase in yield of Nanobody C. This again shows that enhanced expression of the auxiliary protein HAC1spliced is most effective to improve Nanobody yield. This illustrates that enhanced expression of the auxiliary protein HAC1spliced can also further increase the yield of good expressing Nanobodies.

TABLE 4

Expression yields of Nanobody C with and without enhanced expression of auxiliary protein. Yield was estimated using SDS-PAGE/Coomassie staining and quantification of bandvolume was done using Imagequant software (GE Healthcare).

|  | Strain | Yield determined on gel (g/L) | Improvement over reference clone |
|---|---|---|---|
| Nanobody C | Reference | 1.4 | — |
|  | HAC1spliced | 4.8 | 3.4 times |
|  | Kar2p | 0.9 | — |
|  | PDI1 | 1.7 | 1.2 times |
|  | RPP0 | 2 | 1.4 times |

Example 5: Evaluation of the Expression Yields of Different Nanobodies (Nanobody D, Nanobody E, Nanobody F, Nanobody G, and Nanobody H) when Expression of the Auxiliary Protein HAC1spliced is Enhanced Nanobody D is a bivalent Nanobody consisting of two sequence optimized variable domains of a heavy-chain llama antibody. The N-terminal subunit in Nanobody D is a VHH1 type immunoglobulin single variable domain and is specific for binding c-Met, while the C-terminal subunit binds to human serum albumin (HSA). The subunits are fused head-to-tail with a 9G/S linker and contain a C-terminal Flag3-His6 epitope tag. The sequence of Nanobody D (SEQ ID NO: 50) is depicted in Table A-1. Nanobody E is a trivalent Nanobody consisting of three sequence optimized variable domains of a heavy-chain llama antibody. The C-terminal subunit in Nanobody E is a VHH1 type immunoglobulin single variable domain, while the central subunit binds to human serum albumin (HSA). The subunits are fused head-to-tail with G/S linkers and contain a C-terminal Flag3-His6 epitope tag. The sequence of Nanobody E (SEQ ID NO: 51) is depicted in Table A-1. Nanobody F is a trivalent Nanobody consisting of three sequence optimised variable domains of a heavy-chain llama antibody. The C-terminal subunit in Nanobody F is a VHH1 type immunoglobulin single variable domain. The subunits in Nanobody F do not bind to human serum albumin (HSA). The subunits are fused head-to-tail with 35 G/S linkers and contain a C-terminal Flag3-His6 epitope tag. The sequence of Nanobody F (SEQ ID NO: 52) is depicted in Table A-1. Nanobodies G and H are tetravalent Nanobodies consisting of four sequenced optimised variable domains of a heavy-chain llama antibody. The C-terminal subunit in Nanobodies G and H is a VHH1 type immunoglobulin single variable domain, while one of the central subunits binds to human serum albumin (HSA). The subunits are fused head-to-tail with 35G/S linkers. Sequences of Nanobodies G and H (SEQ ID NO: 53 and SEQ ID NO: 54, respectively) are depicted in Table A-1. Nanobody I is a monovalent Nanobody that specifically binds TNF. Nanobody I essentially consists of one sequence optimized variable domain, further comprising one alanine residue as C-terminal extension. Nanobody I is not a VHH1 type immunoglobulin single variable domain. The sequence of Nanobody I (SEQ ID NO: 55) is depicted in Table A-1.

The individual auxiliary protein HAC1spliced was cloned as described in 3.1 and transformed into the *Pichia pastoris* strain NRRL Y-11430. Transformants were grown on selective medium containing Blasticidin™. Single clones were isolated and subsequently transformed with Nanobody D, E, F, G or H. Expression analysis was done as described in Example 1.5. Relative quantifications of the proteins were done by means of Coomassie stained SDS-PAGE densitometry scan measurements (Table 5). Enhancing the expression of HAC1spliced auxiliary protein improved the yield of all Nanobodies. This again demonstrates that enhancement of the expression of the auxiliary protein HAC1spliced effectively improves yield of Nanobodies.

TABLE 5

Expression yields of Nanobody D, E, F, G or H. with and without enhanced expression of HAC1spliced auxiliary protein. Yield was estimated using SDS-PAGE/Coomassie staining and quantification of bandvolume was done using Imagequant software (GE Healthcare).

| Strain | | Yield determined on gel (g/L) | Improvement over reference clone |
|---|---|---|---|
| Nanobody D | Reference | 0.4 | 4.3 times |
| | HAC1spliced | 1.7 | |
| Nanobody E | Reference | 0.8 | 2.0 times |
| | HAC1spliced | 1.6 | |
| Nanobody F | Reference | 0.9 | 2.2 times |
| | HAC1spliced | 2.0 | |
| Nanobody G | Reference | 0.19 | 6.3 times |
| | HAC1spliced | 1.2 | |
| Nanobody H | Reference | 0.25 | 6.0 times |
| | HAC1spliced | 1.5 | |
| Nanobody I | Reference | 2.5 | 3.2 times |
| | HAC1spliced | 8.0 | |

Tables

TABLE A-1

Immunoglobulin single variable domain sequences

| SEQ ID NO | Reference | Amino acid sequence |
|---|---|---|
| 46 | VHH1 consensus sequence | QVQLVESGGGLVQPGGSLRLSCAASGFTLDYYAIGWFRQAPGKEREGVSCISSSDGSTYYADSVKGRFTISRDNAKNTVYLQMNSLKPEDTAVYYCAA |
| 47 | VHH2 consensus sequence | QVQLVESGGGLVQAGGSLRLSCAASGSIFSINAMGWYRQAPGKQRELVAAITSGGSTNYADSVKGRFTISRDNAKNTVYLQMNSLKPEDTAVYYCNA |
| 48 | VH H3 consensus sequence | QVQLVESGGGLVQAGGSLRLSCAASGRTFSSYAMGWFRQAPGKEREFVAAISWSGGSTYYADSVKGRFTISRDNAKNTVYLQMNSLKPEDTAVYYCAA |
| 49 | Nanobody A | EVQLVESGGGLVQPGGSLRLSCAASGFILDYYAIGWFRQAPGKEREGVLCIDASDDITYYADSVKGRFTISRDNAKNTVYLQMNSLKPEDTGVYYCATPIGLSSSCLLEYDYDYWGQGTLVTVSSGGGGSGGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 50 | Nanobody D | EVQLVESGGGLVQPGGSLRLSCAASGFLLNYFEIVWFRQAPGKEREGIICISNSDDKTYYVDSVKGRFTFSRDVAKNTVYLQMNSLKREDTADYYCATNLYGTCHTTLKADDMAYWGKGTLVTVSSGGGGSGGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAADYKDHDGDYKDHDIDYKDDDDKGAAHHHHHH |
| 51 | Nanobody E | EVQLLESGGGLVQPGGSLRLSCAASGFTLDDYAIAWFRQAPGKGREGVSGIDSGDGSAYYADSVKGRFTISSDNSKNTVYLQMNSLRPEDTAVYYCARVRTGWGLNAPDYAMDYWGQGTLVTVSSGGGGSGGGGSGGGGSGGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGGSEVQLLESGGGLVQPGGSLRLSCAASGFTLDYLAIGWFRQAPGKGREGVSCVSSSGQYTYYADSVKGRFTISRDNSESTVYLQMNSLRPEDTAVYYCATDPECYRVRGYYNAEYDYWGQGTLVTVSS |
| 52 | Nanobody F | EVQLVESGGGLVGTGGSLRLSCAASGNIADLGVMGWYRQAPAKKGELVATMPRTGSKWYQDSVKGRFTIHRDNSKSTVDLEMGSLKPEDTAVYYCVASRMFQTILKPNYWGQGTLVTVSSGGGGSGGGGSGGGGSGGGGSGGGGSGGGGSEVQLVESGGGLVQPGESLRLSCVASGFTFSSTDMSWLRQATGKGPEWLSSINGGSSTRYAESVKGRFTVSRDNTKNTLYLQMDSLQPEDTAKYYCARGWTPTGRAGPGTLVTVSSGGGGSGGGGSGGGGSGGGGSGGGGSGGGGSEVQLVESGGGLVQAGGSLRLSCAASGFTLDDYDMSWFRQAPGKEREMISCISSSDGRPYYEDSVKGRFTVTSDNAKNTVYLQMNSLKPEDTAVYYCAAGAKIFAVPGSLCSVRNAHWGQGTLVTVSSGAADYKDHDGDYKDHDIDYKDDDDKGAAHHHHHH |
| 53 | Nanobody G | DVQLVESGGGLVQPGGSLRLSCAASGLTFSTNPMYWYRQAPGKQRELVASISSRGITNYADSVKGRFTISRDNSKNTVYLQMNSLRPEDTAVYYCRLASLSSGTVYWGQGTLVTVSSGGGGSGGGGSGGGGSGGGGSGGGGSGGGGSGGGGSEVQLVESGGGLVQPGGSLRLSCAASGSTRSVNPMAWFRQAPGKQREWVATISRSGYATYADSVKGRFTISRDNSKNTVYLQMNSLRPEDTAVYYCVTGTYWGQGTLVTVSSGGGGSGGGGSGGGGSGGGGSGGGGSGGGGSGGGGSEVQLVESGGGLVQPGGSLRLSCAASGFTFRSFGMSWVRQAPGKGPEWVSSIS |

TABLE A-1-continued

Immunoglobulin single variable domain sequences

| SEQ ID NO | Reference | Amino acid sequence |
|---|---|---|
| | | GSGSDTLYADSVKGRFTISRDNSKNTLYLQMNSLRPEDTAVYYCTIGGSL SRSSQGTLVTVSSGGGGSGGGGSGGGGSGGGGSGGGGSGGGGSGGGGSEV QLVESGGGLVQPGGSLRLSCAASGSTLDYYAIGWFRQAPGKEREGVSCTS NSGSTYYADSVKGRFTASRDNSKNTVYLQMNSLRPEDTAVYYCVATIGCA TLGGTLDVQRYYYRGQGTLVTVSSA |
| 54 | Nanobody H | DVQLVESGGGLVQPGGSLRLSCAASGLTFSTNPMYWYRQAPGKQRELVAS ISSRGITNYADSVKGRFTISRDNSKNTVYLQMNSLRPEDTAVYYCRLASL SSGTVYWGQGTLVTVSSGGGGSGGGGSGGGGSGGGGSGGGGSGGGGSGGG GSEVQLVESGGGLVQPGGSLRLSCAASGRIFSINRMGWYRQAPGKQRELV AGVTINAITNYADSVKGRFTISRDNSKNTVYLQMNSLRPEDTAVYYCHAW ARSSGSAPYSQNWGQGTLVTVSSGGGGSGGGGSGGGGSGGGGSGGGGSGG GGSGGGGSEVQLVESGGGLVQPGGSLRLSCAASGFTFRSFGMSWVRQAPG KGPEWVSSISGSGSDTLYADSVKGRFTISRDNSKNTLYLQMNSLRPEDTA VYYCTIGGSLSRSSQGTLVTVSSGGGGSGGGGSGGGGSGGGGSGGGGSGG GGSGGGGSEVQLVESGGGLVQPGGSLRLSCAASGSTLDYYAIGWFRQAPG KEREGVSCTSNSGSTYYADSVKGRFTASRDNSKNTVYLQMNSLRPEDTAV YYCVATIGCATLGGTLDVQRYYYRGQGTLVTVSSA |
| 55 | Nanobody I | DVQLVESGGGVVQPGGSLRLSCTASGFTFSTADMGWFRQAPGKGREFVAR ISGIDGTTYYDEPVKGRFTISRDNSKNTVYLQMNSLRPEDTALYYCRSPR YADQWSAYDYWGQGTLVTVSSA |
| 56 | Nanobody J | DVQLVESGGGVVQPGGSLRLSCTASGFTFSTADMGWFRQAPGKGREFVAR ISGIDGTTYYDEPVKGRFTISRDNSKNTVYLQMNSLRPEDTALYYCRSPR YADQWSAYDYWGQGTLVTVSS |

TABLE A-2

Auxiliary proteins that were screened for improving the expression of Nanobody A

| Auxiliary protein | SEQ ID NO: | Protein ID/ Reference | Sequence |
|---|---|---|---|
| Fkpa | 1 | BAI37926 | MKSLFKVTLLATTMAVALHAPITFAAEAAKPATTADSKAAFKN DDQKSAYALGASLGRYMENSLKEQEKLGIKLDKDQLIAGVQDA FADKSKLSDQEIEQTLQAFEARVKSSAQAKMEKDAADNEAKGK EYREKFAKEKGVKTSSTGLVYQVVEAGKGEAPKDSDTVVVNYK GTLIDGKEFDNSYTRGEPLSFRLDGVIPGWTEGLKNIKKGGKI KLVIPPELAYGKAGVPGIPPNSTLVFDVELLDVKPAPKADAKP EADAKAADSAKK |
| SKP | 2 | BAI34178.1 | MKKWLLAAGLGLALATSAQAADKIAIVNMGSLFQQVAQKTGVS NTLENEFKGRASELQRMETDLQAKMKKLQSMKAGSDRTKLEKD VMAQRQTFAQKAQAFEQDRARRSNEERGKLVTRIQTAVKSVAN SQDIDLVVDANAVAYNSSDVKDITADVLKQVK |
| EroO | 3 | CAY67364.1 | MRIVRSVAIAIACHCITALANPQIPFDGNYTEIIVPDTEVNIG QIVDINHEIKPKLVELVNTDFFKYYKLNLWKPCPFWNGDEGFC KYKDCSVDFITDWSQVPDIWQPDQLGKLGDNTVHKDKGQDENE LSSNDYCALDKDDDEDLVYVNLIDNPERFTGYGGQQSESIWTA VYDENCFQPNEGSQLGQVEDLCLEKQIFYRLVSGLHSSISTHL TNEYLNLKNGAYEPNLKQFMIKVGYFTERIQNLHLNYVLVLKS LIKLQEYNVIDNLPLDDSLKAGLSGLISQGAQGINQSSDDYLF NEKVLFQNDQNDDLKNEFRDKFRNVTRLMDCVHCERCKLWGKL QTTGYGTALKILFDLKNPNDSINLKRVELVALVNTFHRLSKSV ESIENFEKLYKIQPPTQDRASASSESLGLFDNEDEQNLLNSFS VDQAVISSKEAPEEIKSKPVGKAAYKQNSCPSLGSKSIKEAFH EELHAFIDAIGFILNSYRTLPKLLYTLFLVKSSELWDIFIGTQ RHRDTTYRVDL |
| Kar2p | 4 | AAX77226.1 | MLSLKPSWLTLAALMYAMLLVVVPFAKPVRADDVESYGTVIGI DLGTTYSCVGVMKSGRVEILANDQGNRITPSYVSFTEDERLVG DAAKNLAASNPKNTIFDIKRLIGMKYDAPEVQRDLKRLPYTVK SKNGQPVVSVEYKGEEKSFTPEEISAMVLGKMKLIAEDYLGKK VTHAVVTVPAYFNDAQRQATKDAGLIAGLTVLRIVNEPTAAAL AYGLDKTGEERQIIVYDLGGGTFDVSLLSIEGGAFEVLATAGD THLGGEDFDYRVVRHFVKIFKKKHNIDISNNDKALGKLKREVE KAKRTLSSQMTTRIEIDSFVDGIDFSEQLSRAKFEEINIELFK KTLKPVEQVLKDAGVKKSEIDDIVLVGGSTRIPKVQQLLEDYF DGKKASKGINPDEAVAYGAAVQAGVLSGEEGVDDIVLLDVNPL |

TABLE A-2-continued

Auxiliary proteins that were screened for improving the expression of Nanobody A

| Auxiliary protein | SEQ ID NO: | Protein ID/ Reference | Sequence |
|---|---|---|---|
| | | | TLGIETTGGVMTTLINRNTAIPTKKSQIFSTAADNQPTVLIQV YEGERALAKDNNLLGKFELTGIPPAPRGTPQVEVTFVLDANGI LKVSATDKGTGKSESITINNDRGRLSKEEVDRMVEEAEKYAAE DAALREKIEARNALENYAHSLRNQVTDDSETGLGSKLDEDDKE TLTDAIKDTLEFLEDNFDTATKEELDEQREKLSKIAYPITSKL YGAPEGGTPPGGQGFDDDDGDFDYDYDYDHDEL |
| PDI1 | 5 | ACF17572.1 | MQFNWNIKTVASILSALTLAQASDQEAIAPEDSHVVKLTEATF ESFITSNPHVLAEFFAPWCGHCKKLGPELVSAAEILKDNEQVK IAQIDCTEEKELCQGYEIKGYPTLKVFHGEVEVPSDYQGQRQS QSIVSYMLKQSLPPVSEINATKDLDDTIAEAKEPVIVQVLPED ASNLESNTTFYGVAGTLREKFTFVSTKSTDYAKKYTSDSTPAY LLVRPGEEPSVYSGEELDETHLVHWIDIESKPLFGDIDGSTFK SYAEANIPLAYYFYENEEQRAAAADIIKPFAKEQRGKINFVGL DAVKFGKHAKNLNMDEEKLPLFVIHDLVSNKKFGVPQDQELTN KDVTELIEKFIAGEAEPIVKSEPIPEIQEEKVFKLVGKAHDEV VFDESKDVLVKYYAPWCGHCKRMAPAYEELATLYANDEDASSK VVIAKLDHTLNDVDNVDIQGYPTLILYPAGDKSNPQLYDGSRD LESLAEFVKERGTHKVDALALRPVEEEKEAEEEAESEADAHDE L |
| RPP0 | 6 | CAY67120.1 | MGGINEKKAEYFNKLRELLESYKSIFIVGVDNVSSQQMHEVRQ TLRGKAVILMGKNTMVRKALRDFVEELPVFEKLLPFVRGNIGF VFTNEDLKTIRDVIIENRVAAPARPGAIAPLDVFIPAGNTGME PGKTSFFQALGVPTKISRGTIEITSDVKVVEKDSRVGPSEAQL LNMLNISPFTYGLTVVQVFDDGQVFPANILDITDDELLSHFTS AISTIAQISLAAGYPTLPSVGHSVVNHYKNVLAVSIATDYSFE GSEAIKDRLANPEAYAAAAPAAGEASAGAEETAAAAEEEDEES EDDDMGFGLFD |
| BFR2 | 7 | CAY70333 | MARKTLAETLAELSQPASGDFDIEDQEGGAVLDYGDNSSFGSE SEEDKSNHYVKVGKSRIRENAVKLGGQYEGKKSSRADVFGDED DEEEDDEDVEHSETEDALSVSGSESESDEKNSDQSQGDSESEE ESNSGEDLDYKRSKLQQLISSERKTIVNQLSTSNKQDALKGFA VLNQQKQYDQLVDLRIKLQKGLVASNGLPINKEYYEQNKAPKS SKHLDKLQDKLYNLLDVTLELRGKLLNKSKIVSQEFPPIPSKK RSLQHYLEESSKLDNIVNEYRRNVLVKWSQKVQNASGATALSS SKFKAINQDSSTQVDNYLADMDRLIKRTRLNRRSVVPLGYTET EEVVDDDELIDNDKDNNETKYFSNIDRSLKENKYIYDDDDFYR VLLNDLVDKKVSDTQKLTSTSTVITFSKSKLHKSYERKATKGR KLRYTVQDPLLNFEASNPHAYKWNDYQIDEFFASLFGQKVNMN EDEHNEEVQGESEGEDILKDDIKLFG |
| BMH2 | 8 | CAY68707.1 | MSREDSVYLAKLAEQAERYEEMVENMKTVASSGLELSVEERNL LSVAYKNVIGARRASWRIVSSIEQKEEAKGNQSQVSLIREYRS KIETELANICEDILSVLSEHLIPSARTGESKVFYFKMKGDYHR YLAEFAVGDKRKEAANLSLEAYKSASDVAVTELPPTHPIRLGL ALNFSVFYYEILNSPDRACHLAKQAFDDAIAELETLSEESYKD STLIMQLLRDNLTLWTSDMSETGQEESSNSQDKTEAAPKDEE |
| Cct2 | 9 | CAY71348.1 | MSVNILGDQVSEERAENARLSAFVGAIAVGDLVKTTLGPKGMD KLLTSASSGQSIVTNDGATILKSIPLDNPAAKVLVNLSKVQDD EVGDGTTSVTVLASELLREAEKLVDRKIHPQTIIEGFRIASKA ALEALDKVAVDNSHDDAAFRKDLINIAKTTLSSKILAQDRDKF AEIAVSAILRLRGSTSLERIQLIKIIGGQLSDSYLDDGFILNK KFGLDQPKKIKDASILIANTSMDTDKVKIFGAKFKVDSTSKLA QLEKAEKDKMKAKVEKIKNFNINCFVNRQLIYDWPEQLLADSN INTIEHADFDGVERLALVTGGEVVSTFDYPGKVKLGKCDLIEE VIIGEEVMTRFSGVSEGAACTIILRGATEQVLDEAERSLHDAL SVLSQTTKETRTVLGGGCSEMIMSNAVDTQAQNQEGKKQLAVE AFARALRQLPTILADNAGYDSSELVARLRSAIYSGLTTSGLNL SNGTVGDMRQLGVMESYKLKRAVVNSASEAAEVLLRVDNIIRA KPRTADRNR |
| Erj5 | 10 | CAY67194.1 | MKLHLVILCLITAVYCFSAVDREIFQLNHELRQEYGDNFNFYE WLKLPKGPSSTFEDIDNAYKKLSRKLHPDKIRQKKLSQEQFEQ LKKKATERYQQLSAVGSILRSESKERYDYFVKHGFPVYKGNDY TYAKFRPSVLLTIPILFALATLTHFVFIRLSAVQSRKRLSSLI EENKQLAWPQGVQDVTQKVDVKVYNEHLRKWFLVCFDGSVHYV ENDKTFHVDPEEVELPSWQDTLPGKLIVKLIPQLARKPRSPKE IKKENLDDKTRKTKKPTGDSKTLPNGKTIYKATKSGGRRRK |

TABLE A-2-continued

Auxiliary proteins that were screened for improving the expression of Nanobody A

| Auxiliary protein | SEQ ID NO: | Protein ID/ Reference | Sequence |
|---|---|---|---|
| Gim4 | 11 | XP002491325 | MSEGKPNPNQELFQKQYDEFQETLEALNNKIGQLQGDIEEHNI VLKTITTAPKDRKCFHMIGGVLIEKTAGEVEPTLKTNVTKMND AVENLKNEIQNTHKQFEDWKKKTGVKIVSANE |
| KIN2 | 12 | CAY70388.1 | MDREQGILPQDPFSNSVHVPKLRASSGGQPQKPVIQNSAPATA RMLRNASSSTSAALLKELNTHEHSQRQHTPQKQPSLDAPAALV PVESATKQFHRTSIGDWEFSNTIGAGSMGKVKVAKHRVTHEVC AIKIVIRSAKIWQRNHQNDPEPETEEKRKKLRDEYKKELERDE RTVREAALGKIMYHPNICRLFECYTMSNHYYMLFEIVQGVQLL DYIVSHGKLKETRVRQFARSIASALDYCHSNNIVHRDLKIENI MINNKGEIKLIDFGLSNMYDRRNLLKTFCGSLYFAAPELLSCR PYIGPEIDVWSFGVVLFVLVSGKVPFDDDSVPKLHAKIKRGKV EYPEFISPLCHSLLSQMLVVNPDHRVTLKAAMEHPWMTLGFAG PPSNYLPQRSPIVLPLDLSVVREIANLGLGNEEQIARDITNLI SSREYEACVERWKLDQQKANIKGYSARDDSAIIAFHPLLSTYY LVDEMRKRKLAKGALKGQTSVLDTVKVSPDIPKTPAIPQKLET TDVEQPLLATVPPAYTSPHGQPAELEAMIEPAQPLSSAHPFEM DMTQQQHASRKTHIKHAPERQDRGGYNVHKNNSGGLNSLFRRL SGKRPHKNEAEWEPSSPPPQVHPFSVNDADRTSVRGVSPITQP AAVKNVTSNNSKNYLDPVDDSKLVRRVGSLRITNKEKQQVTSD FPRLPNFTIPEQPPKNAPIPIHAQPTTTGTTFQSNDHEIKKKL QASTSPNEQRGPPTLAPSQQRRLHPTARAKSLGHSRKQSLNFK FGGPANNQLPALPTKENYDVFEDAQITDNNLLNPEGKYSANTN VHIKPMTESQILFEAEHAPPGTMPSVEYPRTLFLKGFFSVQTT SSKPLPVIRYNIIAALCKLNIQFTEVNGGFVCVYRKTENLQIG DIRSPVIESRVTDDTDSDVANSSKLSSSSTANTRVNVIEDDSS SPSSARLKHRRKFSLGNGILNHIRKPTLDGTEFDDYDATVNTP VTPAPANVHSRSSSYHTESDNESMESLHDIRGGSDMILKNVPE RNARQIDTVKEEETDDDDLGSINEGSTHRTPLKFEIHIVKVPL VGLYGVRFKKILGNAWIYKRLASKLLQELNL |
| Mdj1 | 13 | CAY69583.1 | MSQRFLQGMNRRLPHLVWLRTKQPLLSCAFQRHPLSKYQARGF HGSAARLISDPYKTLNVDRNASTSDIKKAYYKLAKQYHPDINK EKGAEKKFHDIQAAYEILSDTEKKQQFDQFGTVFDSDGNPMGG SGGRGGPGNPFAGGNPFGAGNPFGNAAGGFSFNLEDLFGDAFN GANRQGGRRAGGAAYMEQYQGNDVEILKTISFKESIFGTNASV NYNVLDGCNTCEGTGLKKGRKKSTCSTCNGSGASVHYLQGFQM SSTCNACGGTGVTISKDDQCGHCHGNGVGQSSKTTEVKLPCGI RDGTRLRVSGAGDAPNVTKGPNVRTVKGDLIIRVRVKPDPRYS RDGNDIVYNCEIPMTTAALGGQVEIPTLDDTKLRLKVPIGTQH GRTVSIPGQGVPIHGSLSNRGALKVQFNVKVLRPDNATQTALL EALADTFNDTTAKKVNPSWKPFENSAPPAEGEDSDHPSRLKKI ESFLSDAFKRITNKKDDCK |
| HAC1spliced | 14 | Guerfal et al. 2010, Microbial Cell Factories 9: 49, FIG. 2 (PpHac1) | MPVDSSHKTASPLPPRKRAKTEEEKEQRRVERILRNRRAAHAS REKKRRHVEFLENHVVDLESALQESAKATNKLKEIQDIIVSRL EALGGTVSDLDLTVPEVDFPPKSSDLEPMSDLSTSSKSEKASTS TRRSLTEDLDEDDVAEYDDEEEEELPRKMKVLNDKNKSTSIK QEKLNELPSPLSSDFSDVDEEKSTLTHLKLQQQQQQPVDNYVS TPLSLPEDSVDFINPGNLKIESDENFLLSSNTLQIKHENDTDY ITTAPSGSINDFFNSYDISESNRLHHPAAPFTANAFDLNDFVF FQE |
| Def1 | 15 | CAY67433.1 | MSERSSKKGPKGGAKRSSQGSSQGLESTKLATLTELFPDWTAQ DLEPVLEEYPDEDLNVIIENIISGKINKWTDPSAKKEKKKREE SFNASEELSTPSYHQTPNSAKKEYPKKEVKAKSKKSQPRSTTS TTTASTKAQLTPSSNPSTKSSWAAALHQKQEDKPSSTVTPTTE TETPNGENASQSPVAETKSEQEESFAPAAVVETSAKPKSWAAM VAQSAKPKKKILKRPEQAAKPSSNEELSQQNGEIQDEQQSLQT QAETQAEQPIQSIELQQTNEQISQQEQKPVQEPKPLERKQQQQ QQQQPVVLPSAVNLDSIGGISFGSLSLNEKEASSAQQAQQASQ PTSQVQAQTNQQYQRYENQYYNNNRQFYQDGKQVNYDSFVRQ QQQQQQHQQQQYWAHPQAQAQGVASAGGSDLNSASPAASNALP QGGPQGTPSASNANPVNAYNNPQFYTPYVYYPYGQYYQNPQLY SGYMGYGAGQPQTQPHQPQVPPTASPSQQTQQVQPTSGQVPNQ QLAGFQGYQQPYQQAYLNKNGYPLYQQYPQQQQQQVGGQGQSQ PQGKEVEEPKPQQQGQQAGQHQGQQAQLPQQYPGHPGQYFGQQ ALGAQQTPYTEYPVYPNSNDYNNTAKGWI |
| Gas1 | 16 | XP002489568.1 | MFKSLCMLIGSCLLSVLAADFPTIEVTGNKFFYSNNGSQFYI KGVAYQKDTSGLSSDATFVDPLADKSTCERDIPYLEELGTNVI RVYAVDADADHDDCMQMLQDAGIYVIADLSQPNNSIITTDPEW TVDLYDGYTAVLDNLQKYDNILGFFAGNEVITNKSNTDTAPFV |

TABLE A-2-continued

Auxiliary proteins that were screened for improving the expression of Nanobody A

| Auxiliary protein | SEQ ID NO: | Protein ID/ Reference | Sequence |
|---|---|---|---|
| | | | KAAIRDMKTYMEDKGYRSIPVGYSANDDELTRVASADYFACGD SDVKADFYGINMYEWCGKATFSNSGYKDRTAEFKNLSIPVFFS EYGCNEVQPRLFTEVQSLYGDDMTDVWSGGIVYMYFEETNNYG LVTIKSDGDVSTLEDFNNLKTELASISPSIATQSEVSATATEI DCPATGSNWKASTDLPPVPEQAACQCMADALSCVVSEDVDTDD YSDLFSYVCENVSSCDGVSADSESGEYGSYSFCSSKEKLSFLL NLYYSENGAKSSACDFSGSATLVSGTTASECSSILSAAGTAGT GSITGITGSVEAATQSGSNSGSSKSSSASQSSSSNAGVGGGAS GSSWAMTGLVSISVALGMIMSF |
| LHS1 | 17 | CCA36228.1 | MRTQKIVTVLCLLLNTVLGALLGIDYGQEFTKAVLVAPGVPFE VILTPDSKRKDNSMMAIKENSKGEIERYYGSSASSVCIRNPET CLNHLKSLIGVSIDDVSTIDYKKYHSGAEMVPSKNNRNTVAFK LGSSVYPVEEILAMSLDDIKSRAEDHLKHAVPGSYSVISDAVI TVPTFFTQSQRLALKDAAEISGLKVVGLVDDGISVAVNYASSR QFNGDKQYHMIYDMGAGSLQATLVSISSSDDGGIVIDVEAIAY DKSLGGQLFTQSVYDILLQKFLSEHPSFSESDFNKNSKSMSKL WQAAEKAKTILSANTDTRVSVESLYNDIDFRATIARDEFEDYN AEHVHRITAPIIEALSHPLNGNLTSPFPLTSLSSVILTGGSTR VPMVKKHLESLLGSELIAKNVNADESAVFGSTLRGVTLSQMFK AKQMTVNERSVYDYCLKVGSSEINVFPVGTPLATKKVVELENV DSENQLTIGLYENGQLFASHEVTDLKKSIKSLTQEGKECSNIN YEATVELSESRLLSLTRLQAKCADEAEYLPPVDTESEDTKSEN STTSETIEKPNKKLFYPVTIPTQLKSVHVKPMGSSTKVSSSLK IKELNKKDAVKRSIEELKNQLESKLYRVRSYLEDEEVVEKGPA SQVEALSTLVAENLEWLDYDSDDASAKDIREKLNSVSDSVAFI KSYIDLNDVTFDNNLFTTIYNTTLNSMQNVQELMLNMSEDALS LMQQYEKEGLDFAKESQKIKIKSPPLSDKELDNLFNTVTEKLE HVRMLTEKDTISDLPREELFKLYQELQNYSSRFEAIMASLEDV HSQRINRLTDKLRKHIERVSNEALKAALKEAKRQQEEEKSHEQ NEGEEQSSASTSHTNEDIEEPSESPKVQTSHDEL |
| Pma1 | 18 | XP002489633.1 | MSAEEPTKEKIPINHSDDEDEDIDQLIEDLQSVHGFDDEEEEE HHEGATAKPVPEELLQTDPAYGLTTDEVHKRRKRFGENKMAEE KENLLVKFCMFFVGPIQFVMEAAAILAAGLEDWVDFGVILALL FLNASVGFIQEYQAGSIVDELKKTLANSATVIRDGQVVDILAD EVVPGDILKLEDGVVIPADGRLVSEECFLQVDQSAITGESLAV DKKTGDSTYSSSTVKRGEAYMVVTATGDSTFVGRAAALVNKAS AGQGHFTEVLNGIGTILLVLVIATLLVVWVACFYRTSPIVRIL RFTLAITIVGVPVGLPAVVTTTMAVGASYLAKKQAIVQKLSAI ESLAGVEILCSDKTGTLTKNKLSLHEPYTVEGVEADDLMLTAC LAASRKKKGLDAIDKAFLKSLISYPRAKAALTKYKVIEFQPFD PVSKKKVTAYVESPEGERIICVKGAPLFVLKTVEEDHPIPEDVH DNYENKVAEFASRGFRSLGVARKRGQGHWEILGIMPCMDPPRD DTAQTVNEATHLGLRVKMLTGDAVGIAKETCRQLGLGTNIYNA ERLGLGGAGDMPGSEIADFVENADGFAEVFPQHKYNVVEILQQ RGYLVAMTGDGVNDAPSLKKADTGIAVEGASDAARSAADIVFL APGLSAIIDALKTSRQIFHRMYSYVVYRIALSLHLELFLGLWI AIMNRSLNIDLVVFIAIFADVATLAIAYDNAPYSPKPTKWNLP RLWGMSIILGIILAIGTWITLTTMLLPRGGIIQNFGSVDGVLF LEISLTENWLIFITRAAGPFWSSCPSWELAGAVIIVDIIATMF TLFGWWSQNWTDIVTVVRVWIFSFGVFCVMGGAYYLMSESEGF DRLMNGKPRKEPPPQRSMEDFIVAMQRVSTQHEKSG |
| SSE1 | 19 | CAY67046.1 | MSVPFGVDLGNNNTVIGVARNRGIDILVNEVSNRQTPSIVGFG AKSRAIGESGKTQQNSNLKNTVEHLVRILGLPADSPDYEIEKK FFTSPLIEKDNEILSEVNFQGKKTTFTPIQLVAMYLNKIKNTA IKETKGKFTDICLAVPVWFTEKQRSAASDACKVAGLNPVRIVN DITAAVGYGVFKTDLPEDEPKKVAIVDIGHSTYSVLIAAFKK GELKVLGSASDKHFGGRDFDYAITKHFAEEFKSKYKIDITQNP KAWSRVYTAAERLKKVLSANTTAPFNVESVMNDVDVSSSLTRE ELEKLVQPLLDRAHIPVERALAMAGLKAEDVDTVEVVGGCTRV PTLKATLSEVFGKPLSFTLNQDEAIARGAAFICAMHSPTLRVR PFKFEDVNPYSVSYYWDKDPAAEDDDHLEVFPVGGSFPSTKVI TLYRSQDFNIEARYTDKNALPAGTQEFIGRWSIKGVVVNEGED TIQTKIKLRNDPSGFHIVESAYTVEKKTIQEPIEDPEADEDAE PQYRTVEKLVKKNDLEITGQTLHLPDELLNSYLETEAALEVQD KLVADTEERKNALEEYIYELRGKLEDQYKEFASEQEKTKLTAK LEKAEEWLYDEGYDSTKAKYIAKYEELASIGNVIRGRYLAKEE EKKQAIREKEESKKASAIAEKMAAERASREAAGSTNEQAQKNE ENTKDADGDVSMNQDELD |
| Sti1 | 20 | XP002491431.1 | MSSEEFKAQGNQAFQAKDYEKAVSFFTQAIEASPTPNHILFSN RSAAYASLGQYQDALDDANKCVEINGSWAKGYNRVGAAHYGRG |

TABLE A-2-continued

Auxiliary proteins that were screened for improving the expression of Nanobody A

| Auxiliary protein | SEQ ID NO: | Protein ID/ Reference | Sequence |
|---|---|---|---|
| | | | EWDEAHKAYSKALELDPANKMAKEGLNETEIARDAGNDVKNIF SDAGMVEKLKKNPKTAELMKDPELVAKVQKLQTDPKSMSQELF SDPRLMTVMGAMLGVDLGVQPSQQSAPQEDTPVPDAYPEPSSK PETNTTSAKNAAAPEPEKEATPEPVDNSKEEADNLKQQANQLY KKRQFDEAIELYNKAWETFQDITYLNNRAAAEFEKGDYDATIE TCENAVEKGRELRADYKLVAKSFARLGSAYLKKDDLPNAIKFF EKSLTEHRSPDVLSKLRAAEADLKKKEAEEYIDPEKAEEARLQ GKDFFTKGDWPAAVKAYTEMINRAPKDARGYSNRAAALAKLMS FPDAVKDCDKAIELDPSFVRAYIRKATALIAMKDFNKAMTTLE EARTVDADTNEGKAANEINGLYYKASSQRFAAIDGETPEQTFE RASKDPEVSAILQDPVMNSILQQARENPAALQEHMKNPEVAKK INILIAAGVIRTR |
| Uso1 | 21 | XP002493742.1 | MTTPIAQIQLEQEASKNPPKQHTRLSDLVEKTKGTKSWVSPFR TDAKAASPKRESYPPQIVADVKPEDVDNAEEETILDHDDANAT VDPIESESVLDASDISIKGSTAEDNQEEQPEPATDVLPQDAEE EVADKDTQSGDIPQDEGSQAEQEEEQAPEAQEEQVSESQEAKE DDKVDNVEAKKDVADKKVTKQTQQAIKDTEEGAKAVKEAQAKL KEAELKLLKEPVVITPDLLQPPAEDDAEKTLKDKPLLLNRYKQ NKEIAESSLQKKDVENPDQVVDLGGGLLLTQAQIYSIAQARVK PLLGKIDKQVDLNLKADELKKRQTEQQYHEQKDLQQSKNLEKY QTQLTRENNIIVARFDTDIAALSSTILSNATLLEEFATQTRKE IDDLGTKALAEEEKLAEEHETNKTKLEENAKQYKEDLETKLLN ATTGQEDEKTKIEELKVKVEEEKAIADDLEEKAFDKNEALNAK RAELEELVAEEAKLQATVDESEQFQKECDAKAAALSVDHTKST KKLEKLQSHVSALGSAIEKHASKIGFLTGAAVASREVKRKHNE SLKSEWLAEKARIRSEVAKANERKTLEAELERERLAKEKEIER QQKEEQYAQEKLDRAEEEKRLKEDVAELQRVKQLKKEKSKLSK KLASTGSFFAGGVATGAAIGAATGAAAGSAAGAAASGAGAAAS GASKVVSSSTNTASKGASDAAQVGNGAKKTADIKRNESFASNS PEIKIDDETLNKDAKPLFTEVVEDVPTTTSKADEDIKKKNRLS FLGSIKRKASLGSKKEPEKKEPATGVVPASSSIAKDNDDGEYE EVSTLETISDAEYEAHKDDPNYFIVDPK |
| Ydj1 | 22 | XP002492146.1 | MVRETKLYDILGVSPDATDAQLKKAYRVGALKNHPDKNPSPEA AETFKGMSHAYEVLSDPQKREIYDQYGEEGLNGGGAGPGGMGE DIFSQFFGGMFPGGGQPTGPQRGKDIKHSISCTLEELYKGRTA KLALNKTVLCKECDGKGGKNVKKCSACNGQGLRFVTRQIGPMI QRAQVRCDVCNGEGDIISGADRCKACSGKKITNERKILEVNIE RGMRHGQKVVFSGESDQAPDVIPGDVIFVVDEKPHKDFSRKGD DLYYEAKIDLLTALAGGELAIKHISGEYLKITIIPGEVISPGS VKVIVGKGMPVRKSSSYGNLYVKFEIDFPPKNFTTAENLQLLE QVLPARTPVSIPADAEVDEVVLADVDPTQQQRQGGRGGQSYDS DDEEQGGQGVQCASQ |

TABLE A-3

Primers used in genomic DNA PCR for identification of the auxiliary proteins that exert a positive effect on the expression yield of Nanobody A in *P. pastoris*

| General forward primer | SEQ ID NO | Sequence |
|---|---|---|
| FW-AOX promoter | 23 | GACTGGTTCCAATTGACAAGC |

| Specific reverse primers | | Sequence |
|---|---|---|
| RV-FkpA | 24 | GTCGTGGGCGCGCCT TTTTTTGGCGCTATCTGCGG |
| RV-SKP | 25 | GTCGTGGGCGCGCCT TTTGACTTGCTTCAGCACGT |
| RV-Ero | 26 | AGCTGGCGGCCGC TTACAAGTCTACTCTATATGTGGTA |
| RV-Kar2p | 27 | AGCTGGCGGCCGC CTACAACTCATCATGATCATAGTCA |
| RV-PDI1 | 28 | AGCTGGCGGCCGC TTAAAGCTCGTCGTGAGCGTCTGCC |
| RV-RPP0 | 29 | AGCTGGCGGCCGC TTAATCAAACAAACCGAATCCCATG |

TABLE A-3-continued

Primers used in genomic DNA PCR for identification of the auxiliary proteins that exert a positive effect on the expression yield of Nanobody A in *P. pastoris*

| | | |
|---|---|---|
| RV-BFR2 | 30 | AGCTGGCGGCCGC TTATCCAAACAGTTTGATATCATCC |
| RV-BMH2 | 31 | AGCTGGCGGCCGC TCACTCTTCATCTTTGGGAGCAGCT |
| RV-Cct2 | 32 | AGCTGGCGGCCGC TCAACGATTACGGTCGGCAGTGCGT |
| RV-Erj5 | 33 | AGCTGGCGGCCGC TTATTTCCTTCTACGTCCACCGGAT |
| RV-Gim4 | 34 | AGCTGGCGGCCGC CTACTCATTAGCACTCACAATCTTG |
| RV-KIN2 | 35 | AGCTGGCGGCCGC CTATAAATTCAATTCTTGTAGCAGC |
| RV-Mdj1 | 36 | AGCTGGCGGCCGC CTATTTACAGTCGTCCTTCTTATTG |
| RV-HAC1spliced | 37 | ATGCATTAGCGGTAAATGGTGCTGCTGGATGATGCAACCGATTCG |
| RV-Def1 | 38 | AGCTGGCGGCCGC TTAAATCCACCCTTTAGCATTG |
| RV-Gas1 | 39 | AGCTGGCGGCCGC TTAGAATGACATAATCATTCCA |
| RV-LHS1 | 40 | AGCTGGCGGCCGC CTACAACTCATCATGGGATGT |
| RV-Pma1 | 41 | AGCTGGCGGCCGC TTAACCAGACTTCTCGTGCTGA |
| RV-SSE1 | 42 | AGCTGGCGGCCGC TTAATCTAGCTCATCTTGGTTC |
| RV-Sti1 | 43 | AGCTGGCGGCCGC TTAACGAGTACGAATGACACC |
| RV-Uso1 | 44 | AGCTGGCGGCCGC TTATTTGGGATCGACGATGAAA |
| RV-Ydj1 | 45 | AGCTGGCGGCCGC TTACTGAGAAGCACATTGGACAC |

TABLE A-4

CDRs and framework sequences of TNF binding Nanobody I. CDR1, CDR2 and CDR3 were determined according to Kontermann, 2010

| | SEQ ID NO | |
|---|---|---|
| FR1 | 57 | DVQLVESGGGVVQPGGSLRLSCTAS |
| CDR1 | 58 | GFTFSTADMG |
| FR2 | 59 | WFRQAPGKGREFVA |
| CDR2 | 60 | RISGIDGTTY |
| FR3 | 61 | YDEPVKGRFTISRDNSKNTVYLQMNSLRPEDTALYYCRS |
| CDR3 | 62 | PRYADQWSAYDY |
| FR4 | 63 | WGQGTLVTVSS |

The invention claimed is:

1. A composition comprising:
   (i) a first nucleic acid encoding a polypeptide comprising or essentially consisting of at least one immunoglobulin single variable domain having 4 framework regions (FR1 to FR4, respectively) and 3 complementarity determining regions (CDR1 to CDR3, respectively); and
   (ii) a second nucleic acid encoding a HAC1spliced protein having the amino acid sequence of SEQ ID NO: 14.

2. A genetic construct that comprises:
   (i) a nucleic acid encoding a polypeptide comprising or essentially consisting of at least one immunoglobulin single variable domain having 4 framework regions (FR1 to FR4, respectively) and 3 complementarity determining regions (CDR1 to CDR3, respectively): and
   (ii) a nucleic acid encoding a HAC1spliced protein having the amino acid sequence of SEQ ID NO: 14.

3. The genetic construct according to claim 2, wherein the nucleic acid encoding the HAC1spliced protein is located downstream of the nucleic acid encoding the polypeptide comprising or essentially consisting of at least one immunoglobulin single variable domain.

4. The genetic construct according to claim 2, further comprising at least one promoter, wherein expression of the nucleic acid encoding the polypeptide comprising or essentially consisting of at least one immunoglobulin single variable domain and expression of the nucleic acid encoding the HAC1spliced protein is controlled by the same promoter.

5. The genetic construct according to claim 2, further comprising at least two promoters, wherein expression of the nucleic acid encoding the polypeptide comprising or essentially consisting of at least one immunoglobulin single variable domain and expression of the nucleic acid encoding the HAC1spliced protein is controlled by a different promoter.

6. A Pichia host that comprises a genetic construct according to claim 2.

7. The genetic construct according to claim 2, further comprising a nucleic acid encoding an additional protein.

8. The genetic construct according to claim 7, wherein the additional protein is a PDI1 protein, a Kar2p protein, or a RPP0 protein.

9. The genetic construct according to claim 7, wherein:
   the additional protein is a PDI1 protein having the amino acid sequence of SEQ ID NO: 5;
   the additional protein is a Kar2p protein having the amino acid sequence of SEQ ID NO: 4; or
   the additional protein is a RPP0 protein having the amino acid sequence of SEQ ID NO: 6.

10. The genetic construct according to claim 2, further comprising:
   a nucleic acid encoding a PDI1 protein having the amino acid sequence of SEQ ID NO: 5 and a nucleic acid encoding a RPP0 protein having the amino acid sequence of SEQ ID NO: 6;
   a nucleic acid encoding a Kar2p protein having the amino acid sequence of SEQ ID NO: 4 and a nucleic acid encoding a RPP0 protein having the amino acid sequence of SEQ ID NO: 6; or a nucleic acid encoding a PDI1 protein having the amino acid sequence of SEQ ID NO: 5 and a nucleic acid encoding a Kar2p protein having the amino acid sequence of SEQ ID NO: 4.

11. The genetic construct according to claim 7, further comprising a promoter that controls expression of the additional protein.

12. The genetic construct according to claim 2, wherein the polypeptide is a monovalent polypeptide.

13. The genetic construct according to claim 2, wherein the immunoglobulin single variable domain essentially consists of 4 framework regions (FR1 to FR4, respectively) and 3 complementarity determining regions (CDR1 to CDR3, respectively), in which CDR1 is SEQ ID NO: 58, CDR2 is SEQ ID NO: 60 and CDR3 is SEQ ID NO: 62.

14. The genetic construct according to claim 2, wherein the polypeptide further comprises one or more other residues or binding units, optionally linked via one or more peptidic linkers.

15. The genetic construct according to claim 14, wherein the polypeptide is a multivalent construct.

16. The genetic construct according to claim 14, wherein said one or more other binding units provide the polypeptide with increased half-life, compared to the polypeptide without said one or more other binding units.

17. The genetic construct according to claim 16, wherein said one or more other binding units that provide the polypeptide with increased half-life are chosen from the group consisting of binding units that can bind to serum albumin or a serum immunoglobulin.

18. The genetic construct according to claim 16, wherein the one or more binding units that provide the polypeptide with increased half-life are chosen from the group consisting of binding units that can bind to human serum albumin or IgG.

* * * * *